(12) United States Patent  (10) Patent No.: US 7,489,759 B2
Beyrard  (45) Date of Patent: Feb. 10, 2009

(54) METHOD AND APPARATUS FOR X-RAY OR INFRARED IMAGING

(76) Inventor: Norbert Beyrard, 170, avenue des Thermes, Divonne-les-Bains (FR) F-01220

( * ) Notice: Subject to any disclaimer, the term of this patent is extended or adjusted under 35 U.S.C. 154(b) by 175 days.

(21) Appl. No.: 11/462,832

(22) Filed: Aug. 7, 2006

(65) Prior Publication Data

US 2007/0036264 A1   Feb. 15, 2007

Related U.S. Application Data

(60) Provisional application No. 60/745,440, filed on Apr. 24, 2006, provisional application No. 60/707,138, filed on Aug. 10, 2005.

(30) Foreign Application Priority Data

Jul. 10, 2006  (EP)  ................ PCT/EP2006/006802

(51) Int. Cl.
 *G01N 23/00* (2006.01)
(52) U.S. Cl. .......................... 378/25; 378/62
(58) Field of Classification Search .................. 378/62, 378/63, 4, 21–27, 8
 See application file for complete search history.

(56) References Cited

U.S. PATENT DOCUMENTS 3,924,131 A   12/1975  Hounsfield 4,412,289 A   10/1983  Yamaguchi
5,414,623 A   5/1995   Lu
6,173,034 B1 *  1/2001  Chao ............................ 378/37

OTHER PUBLICATIONS 10 pages entitled Albebraic Reconstruction Techniques Can Be Made Computationally Efficient . . . etc. by Gabor T. Herman et al dated Sep. 1, 1993—pp. 600-609.
16 pages entitled "A Tutorial on Art" by Richard Gordon—dated Jun. 3, 1974, pp. 78-93.

* cited by examiner

*Primary Examiner*—Hoon Song
(74) *Attorney, Agent, or Firm*—Sturm & Fix LLP

(57) ABSTRACT

Method and apparatus for X-ray imaging of a body, employing a support to receive a body to be examined, a source emitting a beam of X-rays, a detector irradiated by the beam, a converter for converting the detected intensities into data, a means for turning the mounted mobile support by an angle of rotation about an axis of rotation with respect to the source and the detector and a suitably programmed computer to average the data acquired for a pair of orthogonal angles of rotation to obtain n column and m line mean values for n and m elementary segments of a band of the detector, to construct an initial image (n, m) with the n column and m line mean values, to adjust the coefficient of attenuation in each n×m elementary zone by a method of least squares taking into account the n column and m line mean values regarded as constraints, to repeat the previous stages for data acquired with different pairs of preferably orthogonal angles of rotation, and to average term by term the adjusted images so as to arrive at a synthesis image expressing coefficients of attenuation of the examined body.

21 Claims, 37 Drawing Sheets

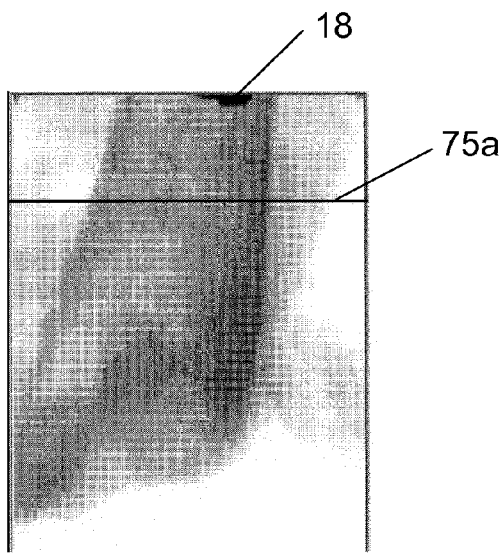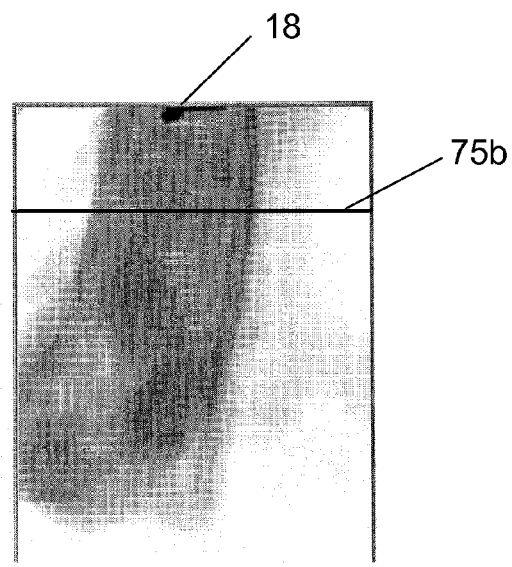
Fig. 3a (0°)  Fig. 3b (90°)
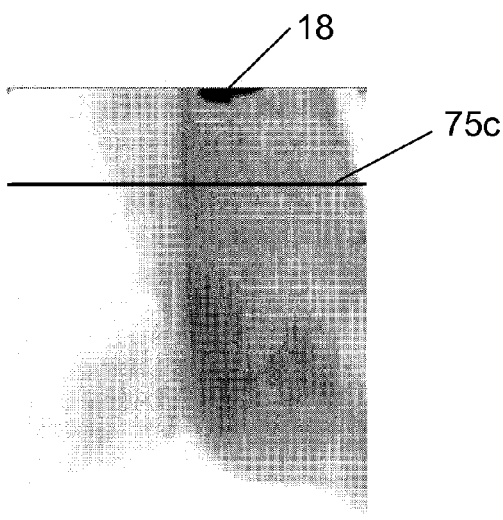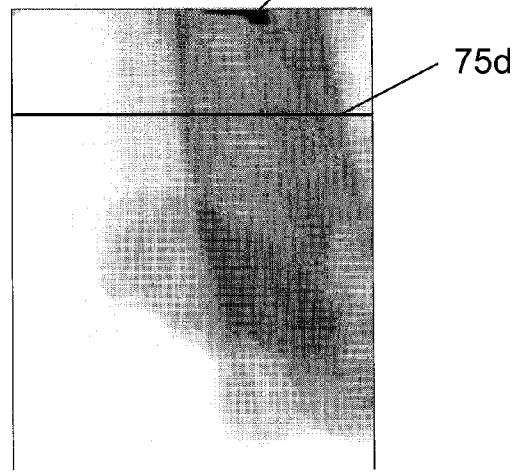
Fig. 3c (180°)  Fig. 3d (270°)

| | coupe 0° | | | coupe 90° | | | | coupe 180° | | | | coupe 270° | | | val corr | 0° | | 90° | | 180° | | 270° | |
|---|---|---|---|---|---|---|---|---|---|---|---|---|---|---|---|---|---|---|---|---|---|---|---|
| positio | moyen | ecart t | medial val co | positi | moyen | ecart t | medi | val c | posi | moyen | ecart t | medial | val cor | posit | moyen | ecart t | medial | val corr | | | | | | | | |
| 1 | 255 | 0,2 | 255 | 0 | 1 | 255 | 0,3 | 255 | 0 | 1 | 255 | 0 | 255 | 0 | 1 | 233,6 | 8,5 | 233 | 21,4 | 5,35 | 1,0465535 | 0 | 1,15 | 0 | 1,9 | 0 | 0,6 | 13,03 |
| 2 | 255 | 0,2 | 255 | 0 | 2 | 255 | 0,1 | 255 | 0 | 2 | 223,2 | 11 | 221 | 27 | 2 | 228 | 7,1 | 229 | 27 | 14,7 | 1,0465535 | 0 | 1,15 | 0 | 1,9 | 59,69 | 0,6 | 16,45 |
| 3 | 254,9 | 1,4 | 255 | 0,1 | 3 | 254,9 | 1 | 255 | 0,1 | 3 | 233 | 7,7 | 233 | 22 | 3 | 220,8 | 9,5 | 221 | 34,2 | 14,1 | 1,0465535 | 0,105 | 1,15 | 0,115 | 1,9 | 41,3 | 0,6 | 20,83 |
| 4 | 254 | 3,7 | 255 | 1 | 4 | 254,6 | 2,4 | 255 | 0,4 | 4 | 243,6 | 5,8 | 244 | 11,4 | 4 | 202,5 | 9,6 | 203 | 52,5 | 16,325 | 1,0465535 | 1,047 | 1,15 | 0,46 | 1,9 | 21,4 | 0,6 | 31,98 |
| 5 | 252 | 6,4 | 255 | 3 | 5 | 254,5 | 2,7 | 255 | 0,5 | 5 | 242,4 | 5,8 | 243 | 12,6 | 5 | 201,6 | 9 | 201 | 53,4 | 17,375 | 1,0465535 | 3,14 | 1,15 | 0,575 | 1,9 | 23,65 | 0,6 | 32,53 |
| 6 | 247,7 | 9,2 | 253 | 7,3 | 6 | 254,4 | 2,9 | 255 | 0,6 | 6 | 241,2 | 6 | 241 | 13,8 | 6 | 193,5 | 10,4 | 193 | 61,5 | 20,8 | 1,0465535 | 7,64 | 1,15 | 0,69 | 1,9 | 25,9 | 0,6 | 37,46 |
| 7 | 240,1 | 11,3 | 239 | 14,9 | 7 | 254,2 | 3,5 | 255 | 0,8 | 7 | 240,9 | 5,8 | 241 | 14,1 | 7 | 179,7 | 9,8 | 180 | 75,3 | 26,275 | 1,0465535 | 15,59 | 1,15 | 0,92 | 1,9 | 26,47 | 0,6 | 45,87 |
| 8 | 232,4 | 11,5 | 231 | 22,6 | 8 | 253,9 | 3,9 | 255 | 1,1 | 8 | 237,3 | 6,3 | 237 | 17,7 | 8 | 170,4 | 8,6 | 170 | 84,6 | 31,5 | 1,0465535 | 23,65 | 1,15 | 1,265 | 1,9 | 33,23 | 0,6 | 51,53 |
| 9 | 203,3 | 24,7 | 206 | 51,7 | 9 | 253,7 | 4,3 | 255 | 1,3 | 9 | 229,9 | 7,6 | 230 | 25,1 | 9 | 164,6 | 9,4 | 165 | 90,4 | 42,125 | 1,0465535 | 54,11 | 1,15 | 1,495 | 1,9 | 47,12 | 0,6 | 55,06 |
| 10 | 167,9 | 15,4 | 168 | 87,1 | 10 | 253,2 | 5,1 | 255 | 1,8 | 10 | 217,2 | 8 | 217 | 37,8 | 10 | 162,8 | 8,6 | 163 | 92,2 | 54,725 | 1,0465535 | 91,15 | 1,15 | 2,069 | 1,9 | 70,96 | 0,6 | 56,16 |
| 11 | 176,3 | 15,2 | 177 | 78,7 | 11 | 247,5 | 9,9 | 200 | 7,5 | 11 | 201,5 | 8,6 | 202 | 53,5 | 11 | 163,7 | 8,6 | 164 | 91,3 | 57,75 | 1,0465535 | 82,36 | 1,15 | 8,623 | 1,9 | 100,4 | 0,6 | 55,61 |
| 12 | 182,2 | 14,9 | 183 | 72,8 | 12 | 201,4 | 23 | 183 | 54 | 12 | 197,3 | 8,2 | 198 | 57,7 | 12 | 165,8 | 9 | 166 | 89,2 | 68,325 | 1,0465535 | 76,19 | 1,15 | 61,62 | 1,9 | 108,3 | 0,6 | 54,33 |
| 13 | 182 | 15,4 | 183 | 73 | 13 | 181,9 | 14,9 | 195 | 73 | 13 | 199,5 | 8,3 | 200 | 55,5 | 13 | 173,1 | 8,2 | 173 | 81,9 | 70,875 | 1,0465535 | 76,4 | 1,15 | 84,04 | 1,9 | 104,2 | 0,6 | 49,89 |
| 14 | 187,8 | 14,7 | 188 | 67,2 | 14 | 193,5 | 15,2 | 196 | 62 | 14 | 198,1 | 8,6 | 199 | 56,9 | 14 | 177 | 8,9 | 177 | 78 | 65,9 | 1,0465535 | 70,33 | 1,15 | 70,71 | 1,9 | 106,8 | 0,6 | 47,51 |
| 15 | 195,1 | 13,8 | 196 | 59,9 | 15 | 195,8 | 13,5 | 193 | 59 | 15 | 186,7 | 9 | 187 | 68,3 | 15 | 175,1 | 8,9 | 175 | 79,9 | 66,825 | 1,0465535 | 62,59 | 1,15 | 68,06 | 1,9 | 128,2 | 0,6 | 48,67 |
| 16 | 204,4 | 14,4 | 206 | 50,6 | 16 | 193,7 | 13,9 | 193 | 61 | 16 | 199,9 | 18 | 194 | 55,1 | 16 | 171,6 | 9,4 | 171 | 83,4 | 62,6 | 1,0465535 | 52,96 | 1,15 | 70,48 | 1,9 | 103,4 | 0,6 | 50,8 |
| 17 | 221,2 | 13,9 | 221 | 33,8 | 17 | 199,4 | 13,9 | 193 | 56 | 17 | 244,5 | 6,1 | 245 | 10,5 | 17 | 163 | 8,9 | 163 | 91,7 | 47,9 | 1,0465535 | 35,37 | 1,15 | 63,92 | 1,9 | 19,71 | 0,6 | 55,85 |
| 18 | 224,9 | 12,9 | 225 | 30,1 | 18 | 200,4 | 13,3 | 201 | 55 | 18 | 249,9 | 5,2 | 251 | 5,1 | 18 | 157,1 | 9 | 158 | 97,9 | 46,925 | 1,0465535 | 31,5 | 1,15 | 62,77 | 1,9 | 9,573 | 0,6 | 59,63 |
| 19 | 226 | 13,2 | 226 | 29 | 19 | 192,3 | 15,8 | 192 | 63 | 19 | 254 | 2,2 | 255 | 1 | 19 | 156,2 | 9,4 | 156 | 98,8 | 47,875 | 1,0465535 | 30,35 | 1,15 | 72,09 | 1,9 | 1,877 | 0,6 | 60,18 |
| 20 | 219,9 | 12,6 | 219 | 35,1 | 20 | 182,4 | 14,6 | 183 | 73 | 20 | 254,9 | 0,7 | 255 | 0,1 | 20 | 168,3 | 9,8 | 168 | 86,7 | 48,625 | 1,0465535 | 36,73 | 1,15 | 83,47 | 1,9 | 0,188 | 0,6 | 52,81 |
| 21 | 220,6 | 11,9 | 220 | 34,4 | 21 | 177,8 | 14,2 | 178 | 77 | 21 | 255 | 0,2 | 255 | 0 | 21 | 190,7 | 9,9 | 191 | 64,3 | 43,975 | 1,0465535 | 36 | 1,15 | 88,76 | 1,9 | 0 | 0,6 | 39,17 |
| 22 | 217,1 | 12 | 217 | 37,9 | 22 | 182,9 | 15,1 | 184 | 72 | 22 | 255 | 0,1 | 255 | 0 | 22 | 208,6 | 10,7 | 209 | 46,4 | 39,1 | 1,0465535 | 39,66 | 1,15 | 82,89 | 1,9 | 0 | 0,6 | 28,26 |
| 23 | 212,7 | 11,8 | 213 | 42,3 | 23 | 193,8 | 13 | 193 | 61 | 23 | 255 | 0 | 255 | 0 | 23 | 225,6 | 7,6 | 228 | 29,4 | 33,225 | 1,0465535 | 44,27 | 1,15 | 70,36 | 1,9 | 0 | 0,6 | 17,91 |
| 24 | 204,6 | 12,5 | 206 | 50,4 | 24 | 196,1 | 12,7 | 196 | 59 | 24 | 255 | 0 | 255 | 0 | 24 | 231,8 | 7,5 | 232 | 23,2 | 33,125 | 1,0465535 | 52,75 | 1,15 | 67,72 | 1,9 | 0 | 0,6 | 14,13 |
| 25 | 200,9 | 13,4 | 201 | 54,1 | 25 | 205,2 | 17,5 | 205 | 50 | 25 | 255 | 0 | 255 | 0 | 25 | 233,7 | 7,5 | 234 | 21,3 | 31,3 | 1,0465535 | 56,62 | 1,15 | 57,25 | 1,9 | 0 | 0,6 | 12,97 |
| 26 | 228,7 | 17,4 | 228 | 26,3 | 26 | 248,2 | 10,6 | 255 | 25 | 26 | 255 | 0 | 255 | 0 | 26 | 237,1 | 6,9 | 237 | 17,9 | 12,75 | 1,0465535 | 27,52 | 1,15 | 7,818 | 1,9 | 0 | 0,6 | 10,9 |
| 27 | 250,3 | 7,8 | 255 | 4,7 | 27 | 253,5 | 4,6 | 255 | 1,5 | 27 | 255 | 0 | 255 | 0 | 27 | 244,2 | 6,6 | 244 | 10,8 | 4,25 | 1,0465535 | 4,919 | 1,15 | 1,725 | 1,9 | 0 | 0,6 | 6,578 |
| 28 | 251,4 | 6,9 | 255 | 3,6 | 28 | 254,2 | 3,4 | 255 | 0,8 | 28 | 255 | 0 | 255 | 0 | 28 | 249,7 | 4,9 | 251 | 5,3 | 2,425 | 1,0465535 | 3,768 | 1,15 | 0,92 | 1,9 | 0 | 0,6 | 3,228 |
| 29 | 250,4 | 7,6 | 255 | 4,6 | 29 | 254,5 | 2,6 | 255 | 0,5 | 29 | 255 | 0 | 255 | 0 | 29 | 252,2 | 3,6 | 254 | 2,8 | 1,975 | 1,0465535 | 4,814 | 1,15 | 0,575 | 1,9 | 0 | 0,6 | 1,705 |
| 30 | 249,2 | 8,5 | 255 | 5,8 | 30 | 254,5 | 2,7 | 255 | 0,5 | 30 | 255 | 0 | 255 | 0 | 30 | 253,8 | 1,8 | 255 | 1,2 | 1,875 | 1,0465535 | 6,07 | 1,15 | 0,575 | 1,9 | 0 | 0,6 | 0,731 |
| 31 | 250,5 | 7,9 | 255 | 4,5 | 31 | 254,5 | 2,5 | 255 | 0,5 | 31 | 255 | 0 | 255 | 0 | 31 | 253,8 | 1,7 | 255 | 1,2 | 1,55 | 1,0465535 | 4,709 | 1,15 | 0,575 | 1,9 | 0 | 0,6 | 0,575 |
| | | | | 987 | | | | | 898 | | | | | 550 | | | | | 1695 | 1032,425 | | 1032 | | 1033 | | 1032 | | 1032 |

| 90 | | | | | | | | |
|---|---|---|---|---|---|---|---|---|
| 1,57 | | | | | | | | |
| -0 | | | | | | | | |
| 1 | | | | | | | | |
| | -3,67E-06 | -1 | 0 | | | | | |
| | 1 | -3,673E-06 | 0 | | | | | |
| | 0 | 0 | 1 | | | | | |
| | | | | | | | | |
| | -3,67E-06 | 1 | 0 | | | | 1,00001 | 1 | 1 |
| | -1 | -3,673E-06 | 0 | x | -2 | 2 | 2 | 2 |
| | 0 | 0 | 1 | y | 1 | 0 | 0 | 0 |
| | | | | z | 0 | | | |

Fig. 14b

| 180 | | | | | | | | |
|---|---|---|---|---|---|---|---|---|
| 3,14 | | | | | | | | |
| -1 | | | | | | | | |
| -0 | | | | | | | | |
| | -1 | 7,346E-06 | 0 | | | | | |
| | -7,35E-06 | -1 | 0 | | | | | |
| | 0 | 0 | 1 | | | | | |
| | | | | | | | | |
| | -1 | -7,346E-06 | 0 | | | 1,99999 | 2 | 2 |
| | 7,346E-06 | -1 | 0 | x | -2 | -1 | -1 | -1 |
| | 0 | 0 | 1 | y | 1 | 0 | 0 | 0 |
| | | | | z | 0 | | | |

Fig. 14c

| 270 | | | | | | | | |
|---|---|---|---|---|---|---|---|---|
| 4,71 | | | | | | | | |
| 0 | | | | | | | | |
| -1 | | | | | | | | |
| | 1,102E-05 | 1 | 0 | | | | | |
| | -1 | 1,102E-05 | 0 | | | | | |
| | 0 | 0 | 1 | | | | | |
| | | | | | | | | |
| | 1,102E-05 | -1 | 0 | | | -1 | -1 | -1 |
| | 1 | 1,102E-05 | 0 | x | -2 | -2 | -2 | -2 |
| | 0 | 0 | 1 | y | 1 | 0 | 0 | 0 |
| | | | | z | 0 | | | |

Fig. 14d

| 360 | | | | | | | | |
|---|---|---|---|---|---|---|---|---|
| 6,28 | | | | | | | | |
| 1 | | | | | | | | |
| 0 | | | | | | | | |
| | 1 | -1,469E-05 | 0 | | | | | |
| | 1,469E-05 | 1 | 0 | | | | | |
| | 0 | 0 | 1 | | | | | |
| | | | | | | | | |
| | 1 | 1,469E-05 | 0 | | | -2 | -2 | -2 |
| | -1,47E-05 | 1 | 0 | x | -2 | 1,00003 | 1 | 1 |
| | 0 | 0 | 1 | y | 1 | 0 | 0 | 0 |
| | | | | z | 0 | | | |

|      | -2,00 | -1,00 | 0,00  | 1,00 | 2,00 | cont ho |
|------|-------|-------|-------|------|------|---------|
| 0,00 | -2,00 | -1,00 | 0,00  | 1,00 | 2,00 |         |
| -2,00| 12,11 | 7,24  | 10,25 | 5,89 | 4,69 | 54,92   |
| -1,00| 9,38  | 4,52  | 7,52  | 3,17 | 4,69 | 27,69   |
| 0,00 | 14,94 | 10,08 | 13,09 | 8,73 | 4,69 | 83,31   |
| 1,00 | 11,99 | 7,13  | 10,13 | 5,78 | 4,69 | 53,80   |
| 2,00 | 12,34 | 7,48  | 10,48 | 6,13 | 4,69 | 57,25   |
| conv | 66,13 | 17,52 | 47,55 | 4,01 | 46,91|         |

Fig. 15

| x   | -2,00 | -1,00 | 0,00  | 1,00  | 2,00 | -2,00 | -1,00 | 0,00 | 1,00 | 2,00 | -2,00 | -1,00 | 0,00  | 1,00 | 2,00 | -2,00 | -1,00 | 0,00  | 1,00 | 2,00 | -2,00 | -1,00 | 0,00  | 1,00 | 2,00 |
|-----|-------|-------|-------|-------|------|-------|-------|------|------|------|-------|-------|-------|------|------|-------|-------|-------|------|------|-------|-------|-------|------|------|
| y   | -2,00 | -2,00 | -2,00 | -2,00 | -2,00| -1,00 | -1,00 | -1,00| -1,00| -1,00| 0,00  | 0,00  | 0,00  | 0,00 | 0,00 | 1,00  | 1,00  | 1,00  | 1,00 | 1,00 | 2,00  | 2,00  | 2,00  | 2,00 | 2,00 |
| z   | 0,00  | 0,00  | 0,00  | 0,00  | 0,00 | 0,00  | 0,00  | 0,00 | 0,00 | 0,00 | 0,00  | 0,00  | 0,00  | 0,00 | 0,00 | 0,00  | 0,00  | 0,00  | 0,00 | 0,00 | 0,00  | 0,00  | 0,00  | 0,00 | 0,00 |
| val | 12,11 | 7,24  | 10,25 | 5,89  | 4,69 | 9,38  | 4,52  | 7,52 | 3,17 | 4,69 | 14,94 | 10,08 | 13,09 | 8,73 | 4,69 | 11,99 | 7,13  | 10,13 | 5,78 | 4,69 | 12,34 | 7,48  | 10,48 | 6,13 | 4,69 |

Fig. 16

| val | 12,11 | 7,24  | 10,25 | 5,89  | 4,69 | 9,38  | 4,52  | 7,52 | 3,17 | 4,69 | 14,94 | 10,08 | 13,09 | 8,73 | 4,69 | 11,99 | 7,13  | 10,13 | 5,78 | 4,69 | 12,34 | 7,48  | 10,48 | 6,13 | 4,69 |
|-----|-------|-------|-------|-------|------|-------|-------|------|------|------|-------|-------|-------|------|------|-------|-------|-------|------|------|-------|-------|-------|------|------|
| x'  | -2,73 | -1,87 | -1,00 | -0,13 | 0,73 | -2,23 | -1,37 | 0,50 | 0,37 | 1,23 | -1,73 | -0,87 | 0,00  | 0,87 | 1,73 | -1,23 | 0,37  | 0,50  | 1,37 | 2,23 | -0,73 | 0,13  | 1,00  | 1,87 | 2,73 |
| y'  | -0,73 | -1,23 | -1,73 | -2,23 | 2,73 | 0,13  | -0,37 | 0,87 | 1,37 | 1,87 | 1,00  | 0,50  | 0,00  | -0,50| 1,00 | 1,87  | 1,37  | 0,87  | 0,37 | 0,13 | 2,73  | 2,23  | 1,73  | 1,23 | 0,73 |
| z'  | 0,00  | 0,00  | 0,00  | 0,00  | 0,00 | 0,00  | 0,00  | 0,00 | 0,00 | 0,00 | 0,00  | 0,00  | 0,00  | 0,00 | 0,00 | 0,00  | 0,00  | 0,00  | 0,00 | 0,00 | 0,00  | 0,00  | 0,00  | 0,00 | 0,00 |

Fig. 17

| Arx' | -3,00 | -2,00 | -1,00 | 0,00  | 1,00 | -2,00 | -1,00 | 1,00 | 0,00 | 1,00 | -2,00 | -1,00 | 0,00  | 1,00 | 2,00 | -1,00 | 0,00  | 1,00  | 1,00 | 2,00 | -1,00 | 0,00  | 1,00  | 2,00 | 3,00 |
|------|-------|-------|-------|-------|------|-------|-------|------|------|------|-------|-------|-------|------|------|-------|-------|-------|------|------|-------|-------|-------|------|------|
| ary' | -1,00 | -1,00 | -2,00 | -2,00 | 3,00 | 0,00  | 0,00  | 1,00 | 1,00 | 2,00 | 1,00  | 1,00  | 0,00  | -1,00| 1,00 | 2,00  | 1,00  | 1,00  | 0,00 | 0,00 | 3,00  | 2,00  | 2,00  | 1,00 | 1,00 |
| val  | 12,11 | 7,24  | 10,25 | 5,89  | 4,69 | 9,38  | 4,52  | 7,52 | 3,17 | 4,69 | 14,94 | 10,08 | 13,09 | 8,73 | 4,69 | 11,99 | 7,13  | 10,13 | 5,78 | 4,69 | 12,34 | 7,48  | 10,48 | 6,13 | 4,69 |

METHOD AND APPARATUS FOR X-RAY OR INFRARED IMAGING

CROSS REFERENCE TO RELATED APPLICATIONS

This application claims priority from U.S. Provisional Patent Application Ser. Nos. 60/707,138 filed Aug. 10, 2005; 60/745,440 filed Apr. 24, 2006; and PCT Application No. PCT/EP2006/006802 filed Jul. 10, 2006, which are incorporated by reference herein in their entirety.

BACKGROUND OF THE INVENTION

1. Field of the Invention

The present invention relates to a method and an apparatus for X-ray or infrared imaging of a body, comprising in particular a support for receiving a body to be examined, a source emitting a beam of X-rays or light rays in a propagation direction in order to irradiate or illuminate the body to be examined, a detector irradiated or illuminated by the beam in order to detect an intensity attenuated according to the passage of the X-rays or light rays through the body to be examined, an analogue-digital converter to convert the detected intensities into data, enabling an attenuation of the X-rays or light rays by the body to be examined to be determined.

2. Description of the Related Art

Such an apparatus is known for example from U.S. Pat. Nos. 3,924,131 or 3,919,552. It will be recalled that scanography (or tomodensitometry) was discovered in 1968 by G. N. Hounsfield, an engineer working in the EMI company. The 1972 patent is entitled: "A method and apparatus for examination of a body by radiation such as X or gamma radiation". In 1979 the inventor was awarded the Nobel prize for his invention.

The principle of the invention is as follows:

A beam of X-rays scans a defined plane, passes linearly through an organ, and strikes a plate or a radiographic detector. The passage through the organ produces an attenuation of the beam, the degree of attenuation being able to be measured by means of the detector. Crosswise scanning in the sectional plane produces a set of information that is processed by suitable software on an associated computer.

In fact, in a heterogeneous medium the attenuation along each scanning axis may be expressed by an exponential law, taking into account the photoelectric absorption and diffusion due to the Compton effect.

Let I0 be the reference value

Ix be the value at a point X, then one may write the following relationship:

$$\int A(x)dx = F$$

$$I = I_0 e^{-F}$$

$$\ln = I_0 E$$

$$\mathrm{Ln}\frac{Io}{Ik} = \int_0^t A(x)\,dx$$

From which one obtains by discretisation:

$$\mathrm{Ln}\frac{Io}{In} = \int_0^t A(x)\,dx = A_1 X_1 + A_2 X_2 + \ldots + A_n X_n$$

The successive values $A_1, A_2 \ldots, A_n$ correspond to the values of each segment defined by $X_1, X_2 \ldots, X_n$.

The profiles of each scanning associated with a specific angle (or a specific position) may then be expressed by a series of equations.

A particular scale may be defined by the value relative to a reference value of the coefficient of attenuation, for example that of water or any other suitably chosen molecule.

The scale most often used is that relating to an abundant molecule in all living organisms, namely water.

If A (H2O) denotes the coefficient of attenuation of water, then a relative scale such as the following may be used:

$Bn = [An - A(\mathrm{H2O})] * 1000 / A(\mathrm{H2O})$

The value of the coefficient of water may be defined as equal to 1 or 0, thereby creating a notation system that is easy to use since water is an essential component of the human body.

Other systems may however be used, according to the way in which the information obtained is expressed (visually). Often a value of 1000 is chosen for bone and a value of −1000 is chosen for air.

The information processing of a sufficient number of cross scannings, defining in fact small elementary cells or zones, enables a set of linear equations to be solved provided that the number of scannings is equal to the number of cells.

The editing and use of the information are carried out by an associated computer.

The computer collects the set of data and then calculates the value of the coefficient of attenuation of each elementary zone.

The information obtained from these calculations is expressed by a map of the tomographic sectional plane.

The set of maps constitutes the three-dimensional scanner image of the analysis, which permits longitudinal or transverse sections.

The medical interpretation is thus based on a real internal image of the tissues.

Such images enable the condition of certain bones, as well as the condition of the brain, to be checked in order to detect a tumour or other anomaly.

The investigations are preceded or completed by other investigations, for example ultrasound echography or magnetic resonance imaging.

Scanning and the methods that it has introduced remain an essential tool of medical investigation.

At the start, a series of angular displacements of the order of 3° were carried out, repeated some hundred times.

The improvements that have been introduced since then enable a plurality of beams to be combined with detection strips of a sufficient length so as to multiply the number of measurements made at any one time thanks to multiple detectors.

In the fifth generation scanners detector strips are used perpendicular to the sectional plane in order to prevent any shift or displacement.

The image that is obtained is the result of a stepwise process:

obtaining values of the attenuations for each projection;

calculations of the values of a profile;

matrix representation of each sectional plane;

conversion of each representation by means of a specific map;

establishment of a spatial cartographic system.

Nowadays volumes of each elementary zone of the order of $mm^3$ are obtained.

However, this is far from the microscopic scale since the number of living cells is of the order of 1 billion per $mm^3$. Human cells have on average a size of 10 μm. The microorganisms that are found in the human body may have a size of the order of 1 $\mu m^3$.

The early detection of cancer presupposes a considerable gain in definition. However, the length of time the system is used for a specific patient cannot exceed a certain economic threshold. Above all however, increasing the number of profiles increases the overall radiation dose.

However, it is known that the development of a cancerous nodule accelerates when it causes an associated vascularisation, this phenomenon occurring when a critical size is reached, say for example 50 to 500 microns. In the conventional procedures the radiation dose and the calculation time are multiplied by 8000 in order to achieve the definition equal to 50 μm.

SUMMARY OF THE INVENTION

The object of the invention is to modify a known apparatus according to the prior art referred to above in order to reduce both the radiation dose and the calculation time of the computer in the processing of the data in order thereby to enable the definition of the investigation and of the resulting images to be improved.

To this end the object of the invention is a method for X ray or infrared imaging of a body, in which a body to be examined is received by a support, and the body to be examined is irradiated or illuminated by means of a source emitting a beam of X-rays or light rays in a propagation direction;

an intensity that is attenuated according to the passage of the X-rays or light rays through the body to be examined is detected by means of a detector irradiated or illuminated by the beam;

the detected intensities are converted into data enabling an attenuation of the X-rays or light rays by the body to be examined to be determined with the aid of an analogue/digital converter;

the mobile mounted support is turned by an angle of rotation about an axis of rotation with respect to the source and to the detector mounted on a stand, or the source and the detector mounted on a mobile stand are turned by an angle of rotation about an axis of rotation with respect to the support, and the following stages are carried out with the aid of a suitably programmed computer:

(1) averaging the data obtained from the conversion of the detected intensities in a band of the detector for a first angle of rotation, to obtain n mean values in n elementary segments of the band, and averaging the data obtained from the conversion of the detected intensities in the band of the detector for a second angle of rotation, to obtain m mean values in m elementary segments of the band, wherein the n and m elementary segments produce a grid of n×m elementary zones of a sectional plane of the object to be examined, perpendicular to the axis of rotation, and wherein the n and m mean values respectively are the terms of a column generating vector and a line generating vector;

(2) construction of an initial matrix (n,m) with the terms of the generating vectors, by assigning to each elementary zone a line term and a column term (Bij) representing a coefficient of attenuation defined by the half sum of the homologous term (i) of the column generating vector, divided by the number (m) of the terms of the line generating vector, and of the homologous term (j) of the line generating vector, divided by the number (n) of the terms of the column generating vector;

(3) adjustment of the coefficient of attenuation in each elementary zone by a method of least squares taking account of line boundary values defined by the sum of the (Bij) terms along a line of the initial matrix and column boundary values defined by the sum of the (Bij) terms along a column of the initial matrix, as well as the terms of the generating vectors regarded as line and column constraints, and by using the following formula:

$$Cij = Bij + \left(\frac{1}{n}\right) * \left(\rho j - \sum_{1}^{n} Bij\right) + \left(\frac{1}{m}\right) * \left(ci - \sum_{j=1}^{m} Bij\right) - \left(\frac{1}{nm}\right) * \left(\sum_{j=1}^{m} \rho j - \sum ijBij\right)$$

where, in this formula,

Cij is the sought value

Bij is the initially estimated value (n) is the number of lines of the initial matrix (m) is the number of columns of the initial matrix $$\sum_{i=1}^{n} Cij = pj$$

for all the values of i, the constraint of the column j $$\sum_{j=1}^{m} Cij = ci$$

for all the values of j, the constraint of the line i, to arrive at a properly adjusted matrix, for which the line and column boundary values calculated with the adjusted values (Cij) are equal, respectively, for each line and column, to the terms of the line and column generating vector, (4) repetition of the stages (1) to (3) for data acquired with different pairs of angles of rotation, and (5) treatment of the properly adjusted matrices obtained for the different pairs of angles, by a rotation operator so as to superimpose all of them on a same pair of angles (0°-90°), followed by term-by-term averaging of the properly adjusted and superimposed matrices in order to arrive at a synthesis matrix representing an image of the coefficients of attenuation of the body examined under a definition determined by the grid.

Preferably the X-ray or infrared imaging method according to the invention is implemented in the following way:

the stage (1) is carried out for four pairs of angles of rotation, preferably mutually orthogonal (0°-90°; 90°-180°; 180°-270°; 270°-360°) so as to form four column generating vectors each having as co-ordinates the n mean values obtained for the first angle of rotation (0°; 90°; 180°; 270°) and four line generating vectors each having as co-ordinates the m mean values obtained for the second angle of rotation (90°; 180°; 270°; 360°) of each of the four pairs of angles;

the four column generating vectors and the four line generating vectors are treated by a rotation operator so as to superimpose them on the same pair of angles of rotation (0°-90°), following which a reduced column generating vector and a reduced line generating vector are formed by term-by-term averaging of the homologous co-ordinates by the column vectors and line vectors superimposed on the same pair of angles of rotation (0°-90°);

stage (2) is carried out starting from the co-ordinates of the reduced column and line generating vectors;

stage (3) is carried out to obtain an adjusted matrix for which the line and column boundary values calculated for the adjusted values (Cij) are equal, respectively, for each line and column, to the terms of the reduced line and column generating vectors, and stages (4) and (5) are carried out for different groups of four pairs of angles of rotation, shifted by a multiple of a reference angle (10°) with respect to the angles of rotation of the pairs of the first group.

For a double detection, the method is implemented in the following way:

the body to be examined is irradiated or illuminated simultaneously by means of a first source and a second source emitting a first beam of X-rays or light rays and a second beam of X-rays or light rays in a first and a second propagation direction, which are preferably orthogonal;

a first detector is irradiated or illuminated by the first beam and by a second detector is irradiated or illuminated by the second beam;

by means of the suitably programmed computer, the stage (1) is carried out by averaging the data obtained from the conversion of the intensities detected in a first band of first detector, and by averaging the data obtained from the conversion of the intensities detected in a second band of the second detector, for the sectional plane of the object perpendicular to the axis of rotation and in which the first and second bands extend.

For reasons of simplicity the sections are generally produced so that the line numbers and column numbers are equal, i.e. n is equal to m.

For large area applications of the method the following procedure is adopted: an area of the body to be examined, parallel to the axis of rotation, is irradiated or illuminated in one or more control pulses of the source, and the following supplementary stages are carried out with the aid of the suitably programmed computer:

(6) recording the data obtained from the conversion of the detected intensities in the whole of the irradiated or illuminated area of the detector;

(7) selecting, from among the recorded data, those that are derived from the conversion of the detected intensities in the band of the irradiated or illuminated area of the detector for the first and second angle of rotation, or in the first and second band respectively of the first and second detector, and carrying out the stages (1) to (5) starting from these selected data.

Where the object to be examined has a millimeter or microscopic size, the method is carried out so that a large or total area of the object to be examined is irradiated or illuminated by the source in such a way that it projects a conical or pyramidal beam, and the computer is suitably programmed to perform the supplementary stage:

(8) the selected data are corrected by multiplying them by a correction factor depending on the one hand on the distance between the geometrical vertex of the conical beam or pyramidal beam and the detector in the axial direction of the beam, and on the other hand on the distance between the geometrical vertex and an elementary segment of the band of the irradiated or illuminated area of the detector, this correction corresponding to a virtual enlargement of the object to be examined along the axis of rotation; and the stages (1) to (5) are carried out using the selected and corrected data.

The invention also covers an apparatus specially designed for the implementation of the method according to the invention, in particular in the case where the body to be examined is the body of an individual, comprising, in a first embodiment:

a support to receive a body to be examined;

a source emitting a beam of X-rays or light rays in a propagation direction so as to irradiate or illuminate the body to be examined;

a detector irradiated or illuminated by the beam so as to detect an intensity that is attenuated according to the passage of the X-rays or light rays through the body to be examined;

and in which the support on the one hand and the source and the detector on the other hand are mobile, the support being mobile with respect to the other two about a vertical axis of rotation so that the individual is accommodated in a standing or sitting position by the support.

The support may comprise a base rotating about the vertical axis of rotation and is preferably provided with means for immobilising the individual or with a chair that is transparent to X-rays.

The source and the detector may be split into two sources and two detectors so as to form two X-ray beams or light beams preferably propagating in two orthogonal directions so as respectively to irradiate or illuminate the two detectors.

The support and, where appropriate, the rotating table are preferably arranged in a cabin that is impermeable to X-rays and the source or the detector respectively emits or receives the X-rays through a junction module that can be moved vertically with the aid of vertical displacement means so as to be displaced with respect to a window formed in a wall of the cabin, and that can be moved horizontally with the aid of horizontal displacement means so that it can be moved through the window and into the cabin.

The source and the detector can be moved vertically with respect to the junction module with the aid of vertical displacement means controlled in a synchronous manner.

Sliding panels are advantageously raised as a group in gantry supports of the cabin by lifting means so as to open an aperture forming the window through which the junction modules are moved horizontally so as to enter the cabin.

The source and the detector are mounted on a bracket so that they can rotate about the vertical axis of rotation.

In a second embodiment the apparatus specifically designed for the implementation of a method according to the invention comprises:

a support to receive a body to be examined;

a source emitting a beam of X-rays or light rays in a propagation direction so as respectively to irradiate or illuminate the body to be examined;

a detector irradiated or illuminated by the beam so as to detect an intensity attenuated according to the passage of the X-rays or light rays through the body to be examined;

the support on the one hand and the source and the detector on the other hand are mobile, the support being mobile with respect to the other two about a horizontal axis of rotation, and in which the source and the detector are split into two sources and two detectors so as to form two X-ray beams or light beams that preferably propagate in two orthogonal directions so as respectively to irradiate or illuminate the two detectors.

The invention also extends to an apparatus specifically designed for the implementation of the aforementioned method, in particular in the case where the body to be examined is of a millimeter or microscopic size, comprising:

a support for receiving the body to be examined;

a source emitting a beam of X-rays or light rays in a propagation direction so as to irradiate or illuminate the body to be examined;

a detector irradiated or illuminated by the beam so as to detect an intensity attenuated on account of the passage of the X-rays or light rays through the body to be examined;

the support on the one hand, and the source and the detector on the other hand are mobile, the support being mobile with respect to the source and the detector about an axis of rotation;

and in which a projection means is provided so that the source irradiates or illuminates the detector with a conical beam or pyramidal beam centred on the axial direction of the beam, and a ratio between, on the one hand, the distance between the vertex of the conical or pyramidal beam and the detector and, on the other hand, the distance between the vertex of the conical or pyramidal beam and the object to be examined controls a coefficient of geometrical enlargement of the object.

The invention also extends to a suitably programmed computer for carrying out a method or an apparatus according to the invention, and to a computer program for carrying out such a method or apparatus when it is loaded in a computer.

The first improvement of the method relates to the acquisition of the data relating to the point-to-point coefficients of attenuation. The inventor has chosen to use in preference the projection of the image on a detector.

This method is normally employed to obtain a radiograph of the object to be examined, resulting in the display of a radiograph-type image on a computer screen followed by the printout of the image.

The information may be acquired in two ways, namely by producing the radiograph image and then processing the latter, or by obtaining information at the outlet of the detector and processing it by converting the analogue information into digital information and then processing this information.

As we shall see hereinafter, a vast amount of information can be provided in this way, and a detector available on the market enables several million items of elementary information to be collected corresponding to pixels of size of the order of 25 microns. The multiplication of information obtained instantaneously by this technique leads to correspondingly large processing requirements, which in turn has led to a review of the processing procedure.

The second improvement accordingly relates to the processing of the information, by replacing the conventional processing involving linear algebra by another method, which may be summarised as follows:

a) for example, in a first image that is obtained, a band or section corresponding to a slice of thickness of for example 1 mm, but which may be as thin as 25 μm, is taken and this band is then divided into elementary segments of 1 mm in length that correspond to the same number of elementary layers parallel to the beam direction and perpendicular to the axis of rotation of the object to be examined. The mean value of the elementary intensities may be measured using appropriate software to read the image, from this the mean value of the coefficients of absorption by the body to be examined are deduced, and this for each elementary segment, and finally the coefficient of attenuation associated with each segment can be obtained. A first vector is thus derived from each band.

A second image is then taken at a different angle, displaced for example by 90° by rotating the object or the imaging apparatus. The band of the detector situated in the same sectional plane is then divided in the same way, from which a second vector is obtained. Two orthogonal vectors are thereby obtained.

b) These two orthogonal vectors (or in any case secant) can be used to form a first initial matrix in the following way: each vector is regarded as a first generating vector of the initial matrix. Each line or column of the matrix is divided by a number equal to the number of terms of the other vector, which gives two sets of elementary terms associated with the different lines or columns. Each term of the matrix may then be evaluated by taking the arithmetic (or geometric) mean of the term corresponding to the line and of the term corresponding to the column on which the term is situated. An initial matrix corresponding to a millimeter slicing is thus formed once the vectors have themselves been obtained.

c) This initial matrix is adjusted by regarding the terms of each vector as line or column constraints, using the adjustment method that is described below.

This adjusted result matrix may be displayed as an image on a screen, providing already a first image. In order to improve the results a series of pairs of images displaced by 90° may be taken, from which as many elementary matrices are obtained as there are pairs, the number of which may be equal to the number of elementary vectors. A matrix with terms equal to the mean value of the homologous terms of the individual matrices may then be calculated. A standard deviation for each term may finally be calculated, and if the set of results is satisfactory the image corresponding to the matrix of the mean values is formed.

The advantage of the apparatus according to the invention is two-fold:

the acquisition of the data is much quicker and less demanding than the system of point-by-point scannings. If the detector has a pixel definition of approximately 25 microns (for example the detector from the ATMEL company, whose size is 23×0.6 cm, has available on its surface 2 million zones of side length 25 microns), this enables several millions of points to be obtained even if one takes into account the free spaces, provided that for example, two images slightly displaced one to the other are obtained.

Due to the high resolution, a single flash lasting a few fractions of a second replaces several million scannings, as a result of which the analysis by physical scanning is replaced by a series of numerical information scannings. The number of radiation exposures involved is thus in particular reduced;

the processing of the data may be greatly simplified by thus calculating at the outset the adjustment that is used, and then repeating the process to obtain a number of adjusted matrices equal to p for p lots of shots. These shots taken at uniformly displaced angles during the course of a complete rotation are matched in pairs displaced by 90°. The synthesis image is obtained by superpositioning in the same plane after rotation, and by calculating the means of the homologous values obtained.

For a matrix of 1,440,000 terms the calculation time is 120 seconds for a PC available on the market. This calculation time is reduced to 8 seconds by employing the method involving grouping pairs of angles of rotation in fours. The improvements introduced by the calculation process that are described in detail in the present invention have led to the following experimental results: it is possible to achieve even better figures with the same PC, the calculation time for 1,440,000 terms being of the order of 1 second, i.e. a very significant improvement.

With more powerful PCs the expected results are as follows:
calculation time for 5,000,000 terms: 1 second;
calculation time for 1000 sections: 1000 seconds, i.e. about 15 minutes.

This is the reason why a multiprocessor available on the market can be used to scan the patients. This system will enable an entire individual to be scanned with a definition of 1 mm in 1 second, and a normal individual to be scanned with a definition of 100 µm over a height of about 10 cm, with the possibility, thanks to the zoom software facility, of being able to scan organs such as the prostate with a definition of 25 µm, in a time that is of the order of 1 minute.

Of course, by using supercomputers that are combined with existing scanners, the times could be improved still further at no extra cost, thanks to the improvement in the performances due to the calculation processes that are disclosed in this patent.

When, in the context of acquiring data, the method is employed with a source of X-rays emitting a continuous beam and a detector having a definition of for example 27 microns, the stage (1) of the computer program involved in the processing plan for the data enables the definition of the initial image being adjusted to be chosen in information terms, corresponding to the grid of n×m elementary zones of the body to be examined. In the previously cited example the adjusted image will, depending on the choice of the user, have a definition equal to 27 microns or a multiple of this number, i.e. 54, 108, 216 or 432. The gap between two images will then also be 27, 54, 108, 216 or 432 microns. Since the method leads to a point-by-point calculation of the coefficient of attenuation, it will furthermore be possible to use a zoom effect, namely to select a specific zone, for example the pelvis of an individual, to produce an average definition image for this zone, and then in the selected zone to define a smaller zone, for example the part of the pelvis corresponding to the prostate, for which a high definition calculation will be carried out.

However, the objection will be raised that an image obtained by a large beam may be of poorer quality, due to the fact that each ray of the slightly conical beam produces an image influenced by the images of the adjacent rays or by the echoes due to strong singularities (for example due to metallic inclusions).

Experience shows however that this influence is not significant. Furthermore, a mathematical treatment can facilitate the analysis, and in fact the values obtained on a line or a column of the result matrix may be treated as values that can be corrected by for example a polynomial adjustment, which has two consequences: the random errors are smoothed, and also the definition can be improved by interpolation between the measured points and use of the correction function, by taking account of two or more crossed interpolations.

The use of a synthesis image obtained from 36 base images eliminates to a very large extent the errors due to the geometry of the beam.

The present invention thus provides a very large saving in technical or information processing means in a field where the cost still remains too high to enable systematic investigations in research on diseases such as cancer to be carried out in many countries.

The following description thus relates to the adjustment calculation method per se according to the invention. This method plays an important rôle in the processing of the signals obtained from the measurement, by the radiographic detectors, of the intensity or of the residual value of the primary beam produced by the X-ray apparatus, after the beam has passed through the organism being investigated.

If it is desired to process a matrix having dimensions of n lines and m columns,
let $B_{ij}$ be the estimated value at the line i and at the column j,
let $C_{ij}$ be the most probable value of the corresponding term of the matrix,
let $\rho j$ be the sum of the terms of the column j,
let $cj$ be the sum of the terms of the line i.

The estimate of $B_{ij}$ is obtained by a method permitting such an estimation, in particular by linear or polynomial adjustment techniques, or in a easiest way, by an arithmetical or geometrical mean value.

In the present case the solution of the values of $C_{ij}$ will be sought, taking into account the constraints of lines and columns, that is to say the minimum of the following function is sought:

$\Sigma(C_{ij}-B_{ij})^2$ for all values of i and j subject to the constraints:

$\Sigma C_{ij}=\rho j$ for all the values of j $\Sigma C_{ij}=ci$ for all the values of i The search for a minimum of the functions subject to constraints will be carried out using the method of Lagrange multipliers, the Lagrangian being written:

$$L = -\sum ij(Cij - Bij)^2 + \sum_{j=1}^{m} \lambda j\left(\sum_{i=1}^{n}(Cij - \rho j)\right) + \sum_{i=1}^{n} \mu i\left(\sum_{j=1}^{m}(Cij - ci)\right)$$

This function is composed of two parts, namely a first part that does not have a left-hand character, and a second part that is a set of linear relations.

The Lagrangian can thus be derived for the variables $C_{ij}$ and $\lambda j$ and $\mu i$, Lagrange multipliers associated with the line and column constraints (we have in fact two sets of constraints, namely the line constraints and the column constraints).

Under these conditions we are able to obtain a set of linear relations relating to the $C_{ij}$ by differentiating the Lagrangian, and a set of relation values relating to the constraint values, which is written:

By specifying that dL/dCij denotes a partial derivative of the function L for the variable Cij.

$$\frac{dL}{dCij} = -2(Cij - Bij) + \lambda j + \mu i = 0 \quad 1$$

and the constraints $$\sum_{i=1}^{n}(Cij - \rho j), \text{ for all } j$$

$$\begin{cases} 2 \\ 1 \end{cases} \Rightarrow Cij = Bij + (\lambda j + \mu i)/2$$

$$\sum_{j=1}^{m} Cij = ci, \text{ for all } i$$

The set of n×m relations corresponding to the partial derivatives plus the n+m constraint relations is linear and allows only one solution corresponding to the nm+n+m variables.

If for example we wish to process a matrix where n, the number of lines, is equal to 25, and m, the number of columns, is equal to 30, then the solution by linear algebra consists in processing:

750 Cij variables 25 variables corresponding to the line multipliers, the µi 30 variables corresponding to the column multipliers, the λj.

A first objective is already achieved since only 55 profiles have to be obtained, instead of 750.

We have in total 750 relationships corresponding to the partial derivatives and 55 relationships corresponding to the constraints, for 805 variables. The solution of this problem by employing matrix calculus is the most obvious solution, but involves very tedious calculations, which are slightly more awkward than those involved in conventional methods. The aim of the inventor was first of all rapidly to improve the calculation processes, but over and above his essential objective, namely limiting the irradiation dose during an examination, he has continued to try and improve the calculation time.

The following is obtained by combining the relationships 1 and 2:

$$\sum_{i=1}^{n} Bij + \frac{n}{2} * \lambda j + \left(\sum_{i=1}^{n} \mu i/2\right) = \rho j$$

$$\sum_{i=1}^{m} Bij + \frac{m}{2} * \mu i + \left(\sum_{j=1}^{m} \lambda j/2\right) = ci$$

One may deduce from these relationships:

$$\lambda j = \left(\frac{1}{n}\right) * \left(2 * \left(\rho j - \sum_{i=1}^{n} Bij\right) - \sum_{i=1}^{n} \mu i\right)$$

$$\mu i = \left(\frac{1}{m}\right) * \left(2 * \left(ci - \sum_{j=1}^{m} Bij\right) - \sum_{j=1}^{m} \lambda j\right)$$

Under these conditions, by substituting for example the value of λj in µi, we obtain:

For all $$j\lambda j = \left(\frac{2}{n}\right) * \left(\left(\rho j - \sum_{i=1}^{n} Bij\right) - \sum_{i=1}^{n} \mu i\right)$$

For all i µi $$i\mu i =$$

$$\left(\frac{1}{n}\right)\left(\sum_{i=1}^{n} \mu i\right) + \left(\frac{2}{m}\right)\left(ci - \sum_{j=1}^{m} Bij - \left(\frac{1}{n}\right) * \sum_{j=1}^{m} \rho j + \sum ijBij * \left(\frac{1}{n}\right)\right)$$

If one defines that $\mu^- = (1/n)\Sigma(i=1 \text{ to } n)\,\mu i$ is the mean of the multipliers associated with the constraint of the lines, we arrive at the two following relationships:

for all $$j\lambda j = \left(\frac{2}{n}\right) * \left(\rho j - \sum_{i=1}^{n} Bi\right) - \mu^-$$

for all $$i\mu i = \mu^- + \left(\frac{2}{m}\right) * \left(ci - \sum_{j=1}^{m} Bij - \left(\frac{1}{n}\right) * \left(\sum_{j=1}^{m} \rho j - \sum ijBij\right)\right)$$

In fact:

$$\frac{1}{m}\sum_{1}^{m} * \sum_{1}^{n} \mu i \text{ is equal to } \mu^-$$

Under these conditions, and by substituting in the relationship:

$$Cij = Bij + \left(\frac{1}{2}\right) * (\lambda j + \mu i)$$

we arrive at the algebraic relationship.

This adjustment formula allows us to deduce the matrix of the Cij from the matrix of the Bij by term-by-term calculation $$Cij = Bij + \left(\frac{1}{n}\right) * \left(\rho j - \sum_{1}^{n} Bij\right) +$$

$$\left(\frac{1}{m}\right) * \left(ci - \sum_{j=1}^{m} Bij\right) - \left(\frac{1}{nm}\right) * \left(\sum_{j=1}^{m} \rho j - \sum ijBij\right)$$

The inventor has thus succeeded in a totally surprising manner in carrying out an algebraic-type calculation that does not require the use of matrix calculus.

The algebraic method allows the partial treatment of the reference matrix, which in many cases may be sufficient.

The numerical validation of this method of processing signals and establishing definition values of the sought-after image in a medical context is described hereinafter.

Example of Application of the Method to a Reduced Model

Let us consider a matrix of n lines and m columns in which n=3, m=4

| INITIAL MATRIX | | | | | | |
|---|---|---|---|---|---|---|
| | 1 | 2 | 3 | 4 | Σ lines | C |
| 1 | 22 | 24 | 18 | 16 | 80 | 78 |
| 2 | 24 | 22 | 18 | 20 | 84 | 85 |
| 3 | 26 | 20 | 22 | 24 | 92 | 93 |
| Σ columns | 72 | 66 | 58 | 60 | 256 | |
| P | 70 | 67 | 59 | 60 | | 256 |

In this matrix the estimated values are entered in the three lines and in the four columns, and the line constraints are entered in the column C.

The column constraints are entered in the last line P.

The application of the above formula is simplified since the total of the column (or line) constraints is equal to the sum of the terms and leads to:

| EQUILIBRIUM AFTER CALCULATIONS | | | | | | |
|---|---|---|---|---|---|---|
| | 1 | 2 | 3 | 4 | Σ 2 | C | Δ |
| 1 | 20.83333 | 23.83333 | 17.8333 | 15.5 | 78 | 78 | 0 |
| 2 | 23.5833 | 22.58333 | 18.5833 | 20.25 | 85 | 85 | 0 |
| 3 | 25.5833 | 20.5333 | 22.583 | 24.25 | 93 | 93 | 0 |
| Σ 2 | 70 | 67 | 59 | 60 | 256 | | |
| P | 70 | 67 | 59 | 60 | | | |
| Δ | 0 | 0 | 0 | 0 | | | |

It may be checked, by taking calculations performed on a simple calculator, that the value of the vertically or horizontally summated terms not only satisfies the constraints but also leads to the desired results.

Equilibration Using the Method of Linear Algebra

This method expresses directly the linear relationships between the variables Cij and Bij, and the variables $\lambda_j$ and $\mu_i$.

The conventional method for solving a linear system involves inversion of the matrix of the coefficients of the relationships between the variables and the multiplication, by this inverse matrix, of the vector expressing the second terms of the relationships.

a) There are 12 relationships between the variables resulting from the expression of the partial derivatives of the LAGRANGIAN of the form:

$Cij - \lambda_j/2 - \mu_i/2 = Bij$ b) There exist 4 constraint relationships relating to the columns and 3 constraint relationships relating to the lines, of the form:

$$\sum_{i=1}^{m} Cij = pj \quad \sum_{i=1}^{n} Cij = ci$$

The conventional method then requires the inversion of a matrix of size equal to n*m+n+m, i.e. in our case 19×19, the calculation time for which is clearly far too high.

In the simple example that has just been described, as well as in the example given by tables 4 to 6 for 31×31 terms, the initial values Bij have been estimated by a matrix enlargement method. However, such a method is not regarded as specific to the present invention, which uses a generation method starting from the constraint vectors themselves to estimate the initial values Bij, as is explained hereinafter. We give a simple example hereinbelow, which for the sake of clarity contains only 3×4 terms.

We thus have a matrix of n lines and m columns in which n=3, m=4,

| INITIAL MATRIX | | | | | | |
|---|---|---|---|---|---|---|
| | 1 | 2 | 3 | 4 | Σ lines | C |
| 1 | 21.42 | 20.90 | 19.58 | 19.75 | 81.65 | 78 |
| 2 | 22.29 | 21.80 | 20.46 | 20.63 | 85.18 | 85 |
| 3 | 23.29 | 22.80 | 21.46 | 21.63 | 89.18 | 93 |
| Σ columns | 67.00 | 65.50 | 61.50 | 62.00 | 256 | |
| P | 70 | 67 | 59 | 60 | | 256 |

In this matrix the estimated values are entered in the three lines and the four columns, and the line constraints are entered in the column C. The column constraints are entered in the last line P. The initial values Bij were generated from the line and column constraint values by using an arithmetic mean. Thus:

21.417=(78/4+72/3)/2; 20.9=(78/4+67/3)/2;

19.58=(78/4+60/3)/2; 19.75={78/4+60/3)/2;

22.292=(85/4+70/3)/2; 21.8=(85/4+67/3)2; 20.46=(85/4+59/3)/2

20.625=(85/4+60/3)/2;

23.292=(93/4+70/3)/2; 22.8=(93/4+67/3)/2; 21.46=(93/4+59/3)/2

21.625=(93/4+60/3)/2.

Next, the initial values Bij were summated by line and by column. The sums obtained are shown in the table. Thus:

21.417+20.9+19.58+19.75=81.647;

22.292+21.8+20.46+20.625=85.177, 23.292+22.8+21.46+21.625=89.177;

21.417+22.292+23.292=67, 20.9+21.8+22.8=65.5;

19.58+20.46+21.46=61.5;

19.75+20.625+21.625=62.

The application of the general adjustment formula is simplified in this case since the total of the column (or line) constraints, 256, is equal to the sum of the column (or line) terms, 256, and leads to:

| EQUILIBRIUM AFTER CALCULATIONS | | | | | | |
|---|---|---|---|---|---|---|
| | 1 | 2 | 3 | 4 | $\Sigma^2$ | C | $\Delta$ |
| 1 | 21.50 | 20.49 | 17.83 | 18.17 | 78 | 78 | 0 |
| 2 | 23.25 | 22.26 | 19.58 | 19.91 | 78 | 85 | 0 |
| 3 | 25.25 | 24.26 | 21.58 | 21.91 | 93 | 93 | 0 |
| $\Sigma^2$ | 70 | 67 | 59 | 60 | 256 | | |
| P | 70 | 67 | 59 | 60 | | | |
| $\Delta$ | 0 | 0 | 0 | 0 | | | |

Each value was adjusted in the following way:

$21.5 = 21.417 + (78-81.647)/4 + (70-67)/3;$ $23.25 = 22.292 + (85-85.177)/4 + (70-67)/3,$ $25.25 = 23.29 + (93-89.18)/4 + (70-67)/3;$ $20.5 = 20.9 + (78-81.65)/4 + (67-65.5)/3,$ $22.3 = 21.80 + (85-85.18)/4 + (67-65.5)/3;$ $24.3 = 22.8 + (93-89.18)/4 + (67-65.5)/3,$ $17.8 = 19.58 + ((78-81.65)/4 + (59-61.5)3;$ $19.6 = 20.46 + (85-85.18)/4 + (59-61.5)/3,$ $21.6 = 21.46 + (93-89.18)/4 + (59-61.5)/3;$ $18.167 = 19.75 + (78-81.65)/4 + (60-62)/3,$ $19.917 = 20.63 + (85-85.18)/4 + (60-62)/3;$ $21.917 = 21.63 + (93-89.18)/4 + (60-62)/3.$

It may be checked using calculations performed on a simple calculator that the value of the vertically or horizontally summated terms not only satisfy the constraints, but also effectively lead to the desired results.

In this simple example, an arithmetic mean was used to calculate the initial values Bij from the line and column constraint values. It is also possible to use other means, for example a geometric mean. In this case each value Bij is equal to the square root of the product of the homologous term of the line constraint vector and the homologous term of the column constraint vector. This geometric mean increases the calculation time however, which is why it is preferred to use the arithmetic mean.

In practice one tends to generate matrices the number of lines of which is equal to the number of columns, from vectors of identical size and in which the sum of the terms is, for physical reasons, equal to the same value for each of the vectors. Under these conditions the third term of the general formula is zero. The result matrix of size n may then be generated directly from two generator vectors in which the first corresponds to the vertical vector representative of the line constraints, and the second corresponds to the horizontal vector representative of the column constraints.

The direct generation vectors are such that each term of the vertical vector is equal to the line constraint divided by n, less the sum of the terms of the vector divided by $2n^2$. Symmetrically, the terms of the horizontal vector are equal to the column constraint divided by n, less the sum of the terms of the vector divided by $2n^2$. From the point of view of the calculation, the calculation time is halved.

BRIEF DESCRIPTION OF THE DRAWINGS

FIGS. 3a to 3d show images obtained respectively at 0°, 90°, 180° and 270°.

FIG. 4 is a table of the intensities detected respectively at 0°, 90°, 180° and 270°.

Figure 5:
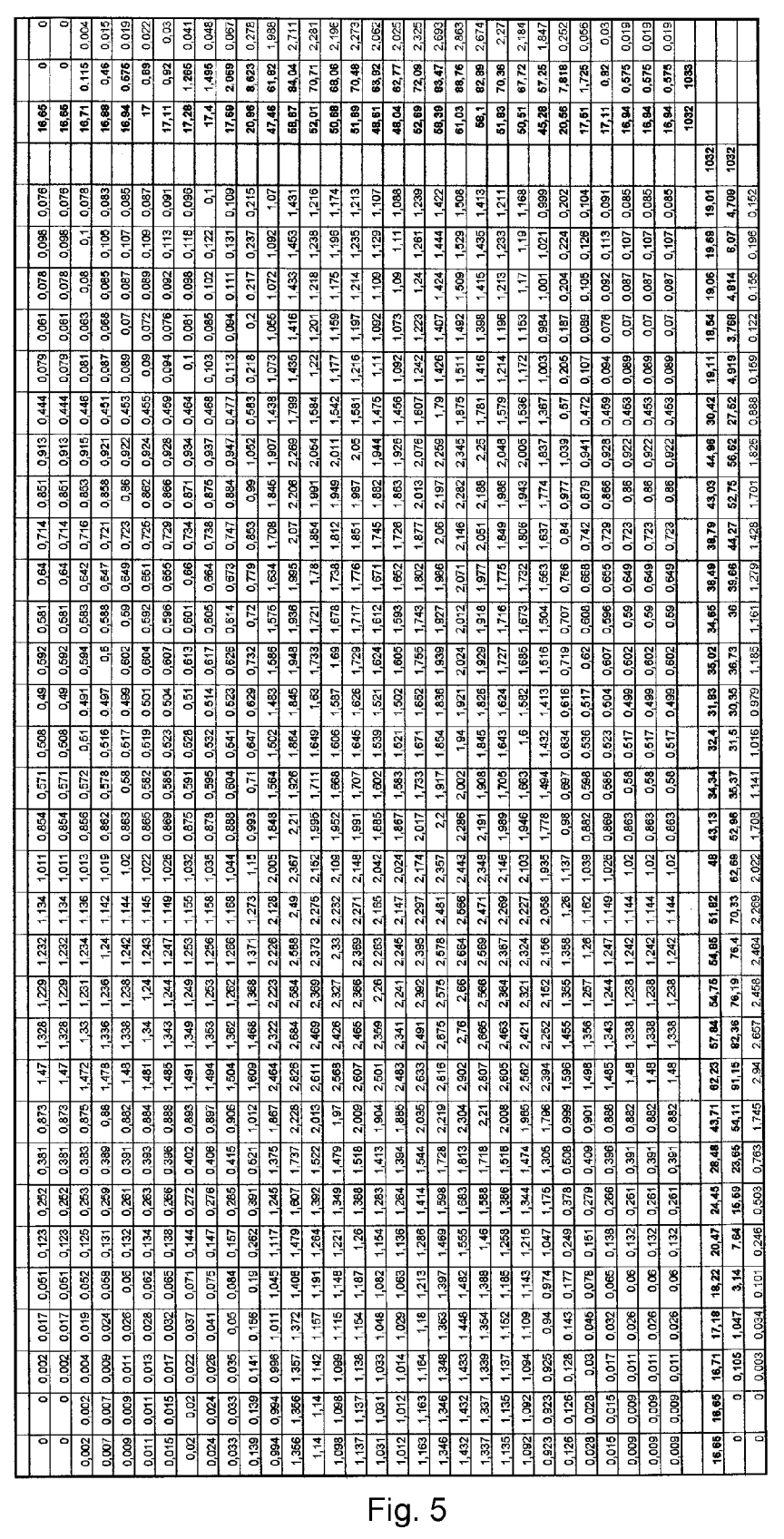

FIG. 5 is a table representing an initial matrix.

Figure 6:
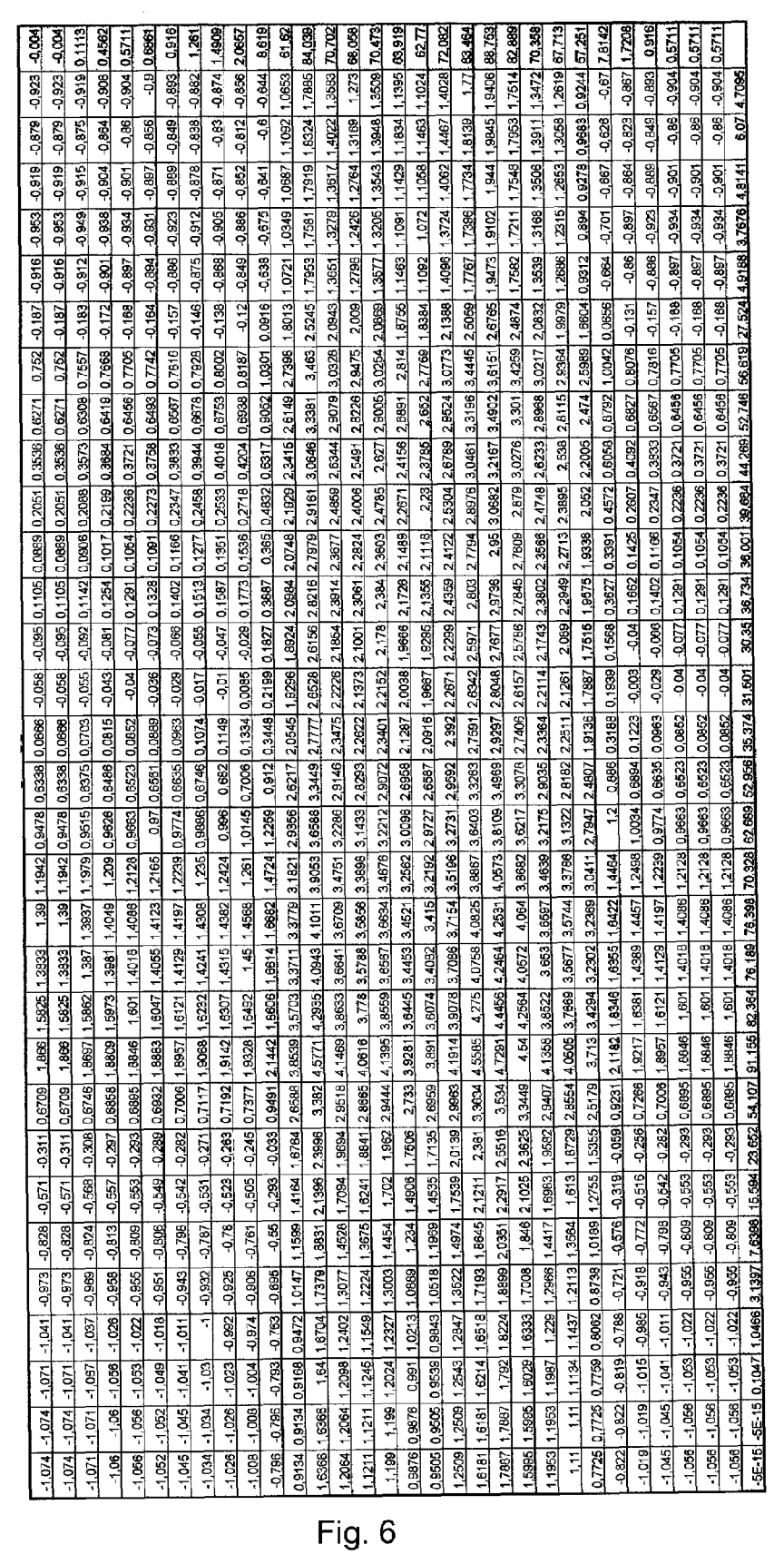

FIG. 6 is a table representing an adjusted result matrix.

FIGS. 7 and 8 show a synthesis matrix table that aggregates the result matrices adjusted for respectively the pairs 0°-90°, 90°-180°, 180°-270° and 270°-360°.

FIGS. 14a to 14d show four tables illustrating a rotation treatment of, respectively, 90°, 180°, 270° and 360°.

FIGS. 15 to 18 show respectively an initial matrix, the expansion of the initial matrix into an expanded matrix, the rotation of the expanded matrix by an angle of 30°, and the structure of a matrix expanded and turned by 30°, with a rounding-up to the whole values of the co-ordinates after the turning.

DETAILED DESCRIPTION OF THE PREFERRED EMBODIMENT

Figure 1:
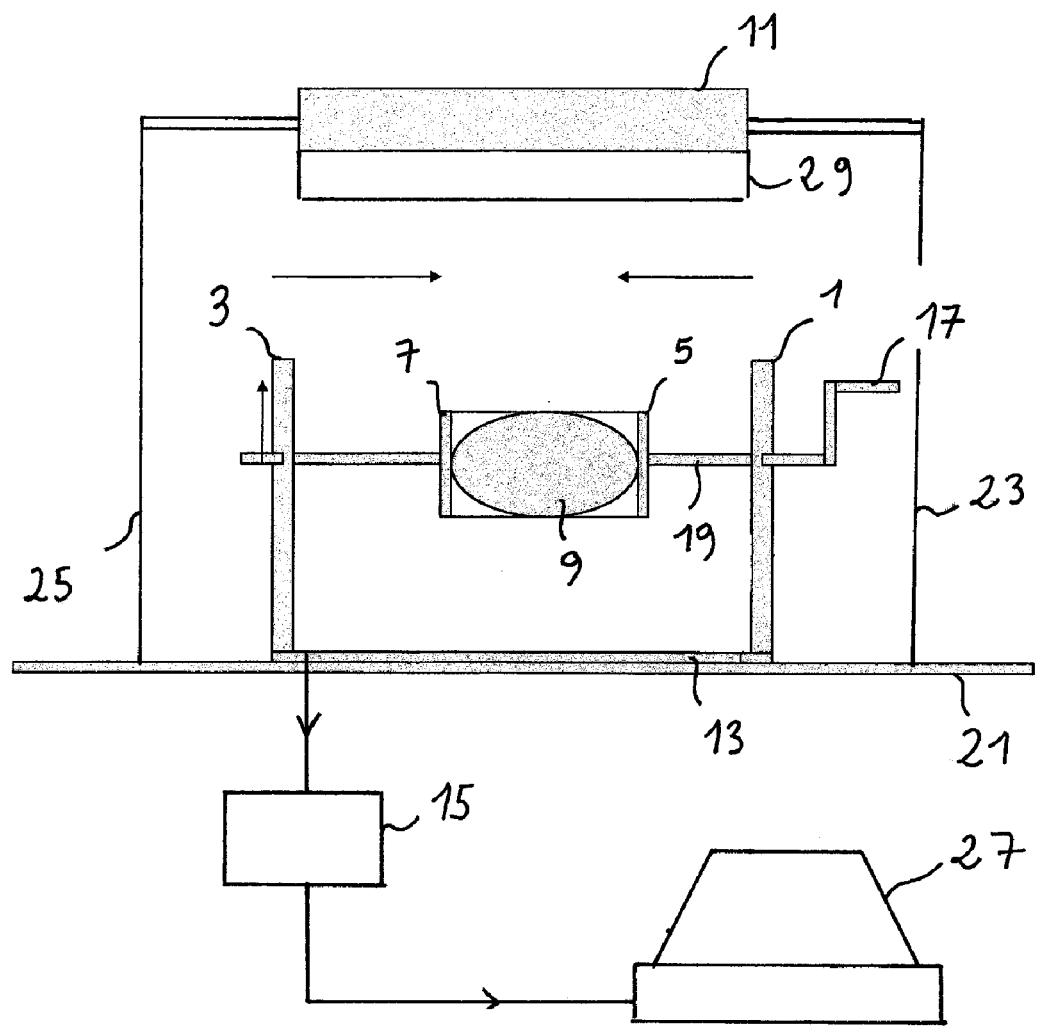
FIG. 1 shows diagrammatically a first apparatus according to the invention.
Figure 2:
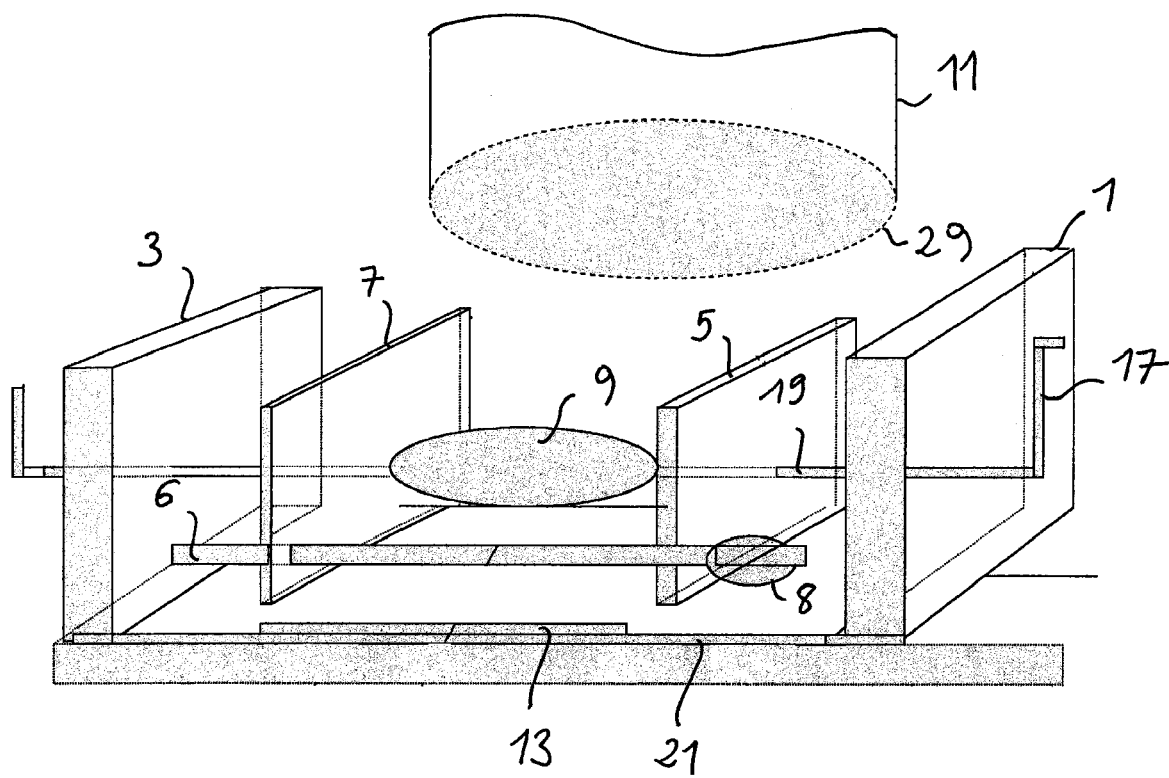
FIG. 2 shows the apparatus of FIG. 1 in a more detailed view.

In order to check the functioning of the apparatus, the inventor has made a prototype comprising the following components:

- a 70 kv X-ray beam emitted by a lead tube of a source 11, the diameter of which is 6 cm and that forms the tip 29,
- a small detector 13 of size 45×30 mm,
- a means 17 enabling an object 9 to be examined and placed between the beam and the detector 13 to be rotated, with a step of 1 (see FIGS. 1 and 2),
- a microcomputer 27 which is connected to a medical imaging software (KODAK), which enables a radiographic image to be obtained at different rotation steps of the object 9 to be examined, a) firstly, 36 images were taken in 10° steps, that is to say: 0, 10, 20, ... 90, ... 180, ... 270, ... 360

A 360° 'check' image was then taken, which is superimposed exactly on the 0° image, thereby confirming that the rotation was correctly performed. By way of example we enclose the following images in the annexe: FIGS. 3a to 3d, the images at 0°, 90°, 180°, 270° of the detected intensities.

b) Secondly, an analysis using rectangular pairs was carried out: −0-90°; 90°-180°; 180°-270°; 270°-360° (0).

c) A narrow section corresponding to a thickness of 1 mm, i.e. one-thirtieth of the thickness of each image, is cut at a certain distance from the reference plane (which can be seen in the accompanying images in the FIGS. 3a to 3d and 9, as a black spot 18 at the end of the rotation spindle 19). Four bands 75a, 75b, 75c and 75d corresponding to 0°, 90°, 180° and 270° are thus obtained.

Each band of 1 mm in thickness is in turn divided into elementary segments of 1 mm in length corresponding to an elementary square of 1 mm² size, in the useful part of the image, which is (approximately) 30 mm. The mean value of the intensity of the pixels in each of the 1 mm² squares is read using suitable software. A vector of thirty (or thirty-one) terms is then obtained, corresponding to the means of each of the elementary squares.

As can be seen on examining Table 4, the values vary between 0 and 255. For a value of 255 the elementary segment or square is completely white (blank); under these conditions it is assumed that the coefficient of attenuation along the line ending at the term corresponding to the vector is equal to 255 less the value of the luminous intensity of the homologous spot. Under these conditions, if no object is interposed, the value of the coefficient of attenuation is equal to 0. If the segment or square is completely black, the value of the coefficient of attenuation is equal to 255, and all the radiation of the beam has been absorbed.

The same treatment is repeated for the bands at 90°, 180° and 270°, as shown in Table 4 in the columns headed VAL CORR (corrected value). The corrected values appear for the four sections 0°, 90°, 180° and 270°. In this table the mean values are estimated by suitable software, as are the standard deviations, which remain within acceptable limits.

In the case where the recognised number of pixels is high, the analysis may be carried out to a definition that is substantially better than one millimeter. The values obtained are corrected so that the sum of the values of each of the columns is equal to the mean value, since under the same distance conditions the absorption of a given body is constant.

d) The preceding term is divided by 31 in order to obtain wherefrom the horizontal (90°) or vertical (0°) constraint value, these values being shown in Table 5. Table 5 (initial matrix) accordingly shows:

the sums of the lines and columns;

the constraints obtained from Table 4;

the divergences between sums and constraints;

the reduced divergences obtained by dividing the above divergences by 31.

This initial matrix is shown in Table 5, after calculating each term.

f) If it is desired to obtain quickly an image with a definition of 1 mm, the adjustment calculation is performed, which leads to the results Table 6.

The procedure that we have employed may be repeated, which consists in forming 36 images from 36 sections made in 36 elementary radiographic images and calculating, pair by pair, the estimated data as described hereinbefore for the first angle of rotation equal to 0° and the second angle of rotation equal to 90°.

The 36 images are then superimposed by rotating each of the images (except the first image) by an angle equal to the opposite of the angle of rotation starting from the point 0°.

Figure 7:
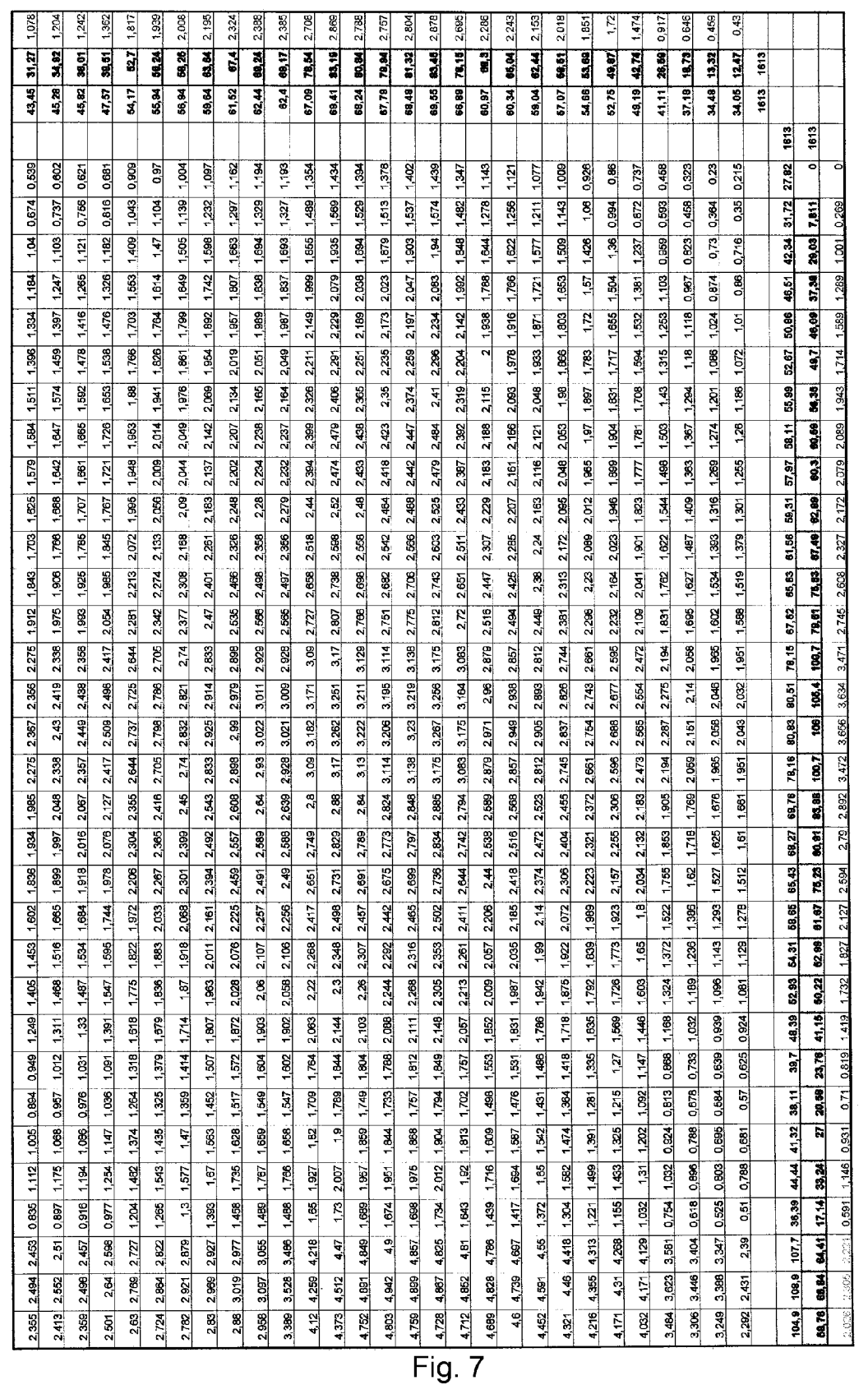
Figure 8:
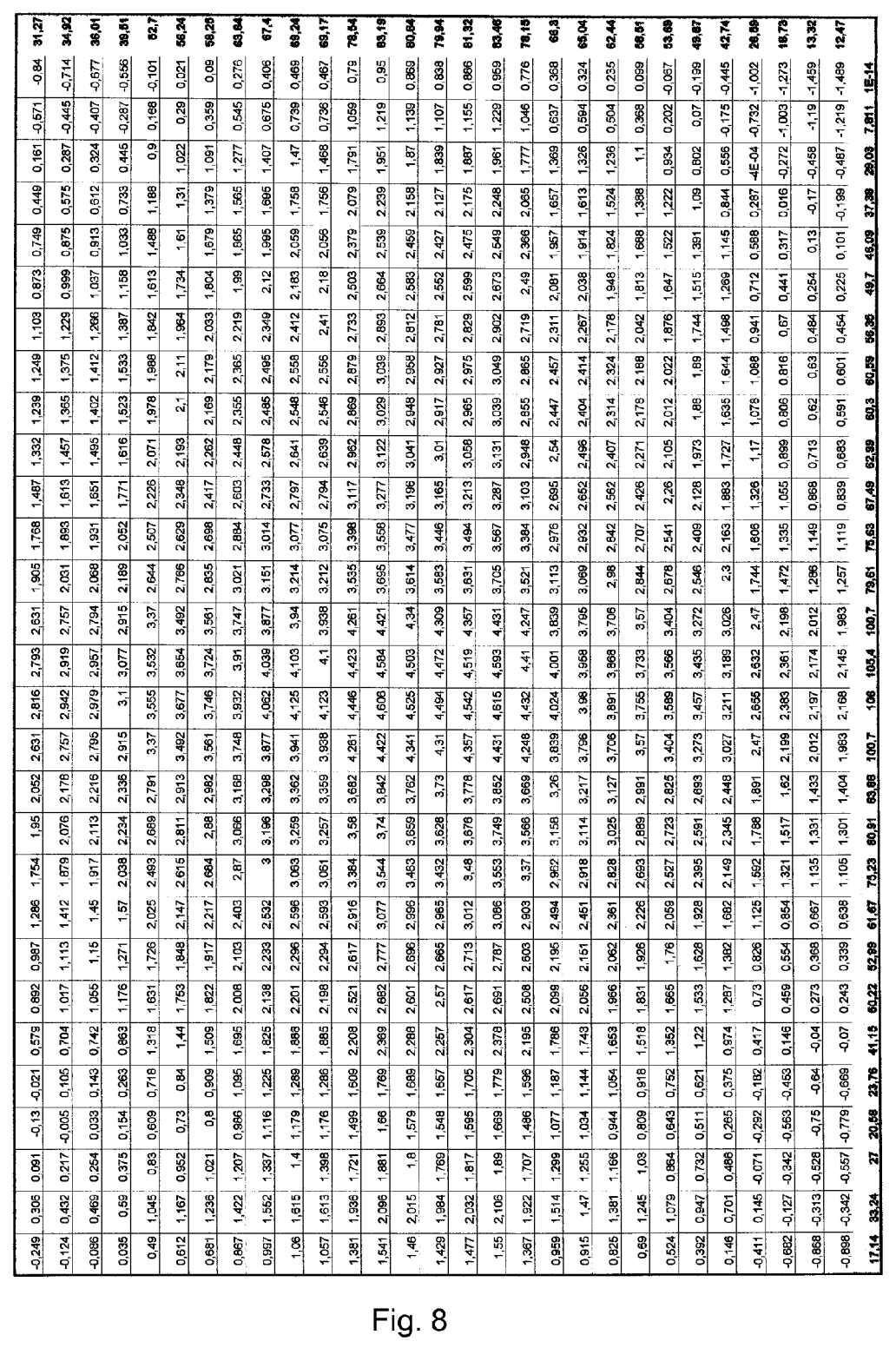

If the tables obtained for the pairs 0°-90°, 90°-180°, 180°-270° and 270°-360° are combined, this leads after rotation to the tables of FIGS. 7 and 8.

Figure 9:
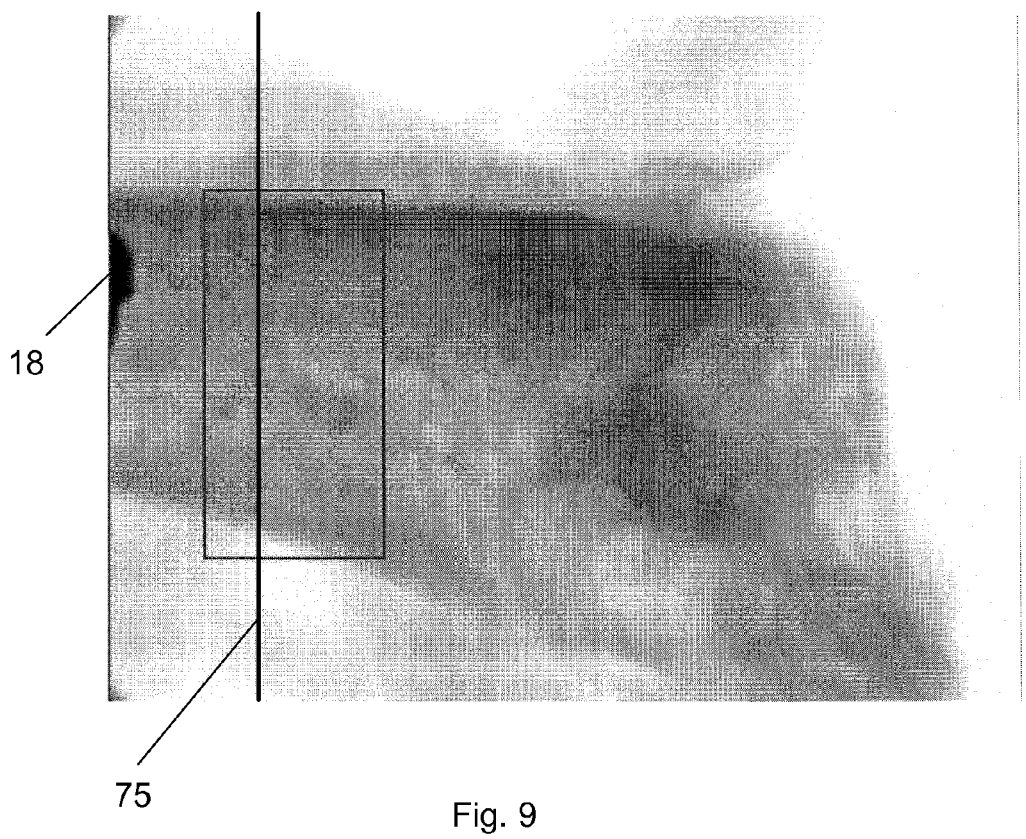
FIG. 9 refers to one of the FIGS. 3a to 3d, wherein a narrow band has been selected in a sectional plane of the irradiated or illuminated area of the object to be examined.
Figure 10:
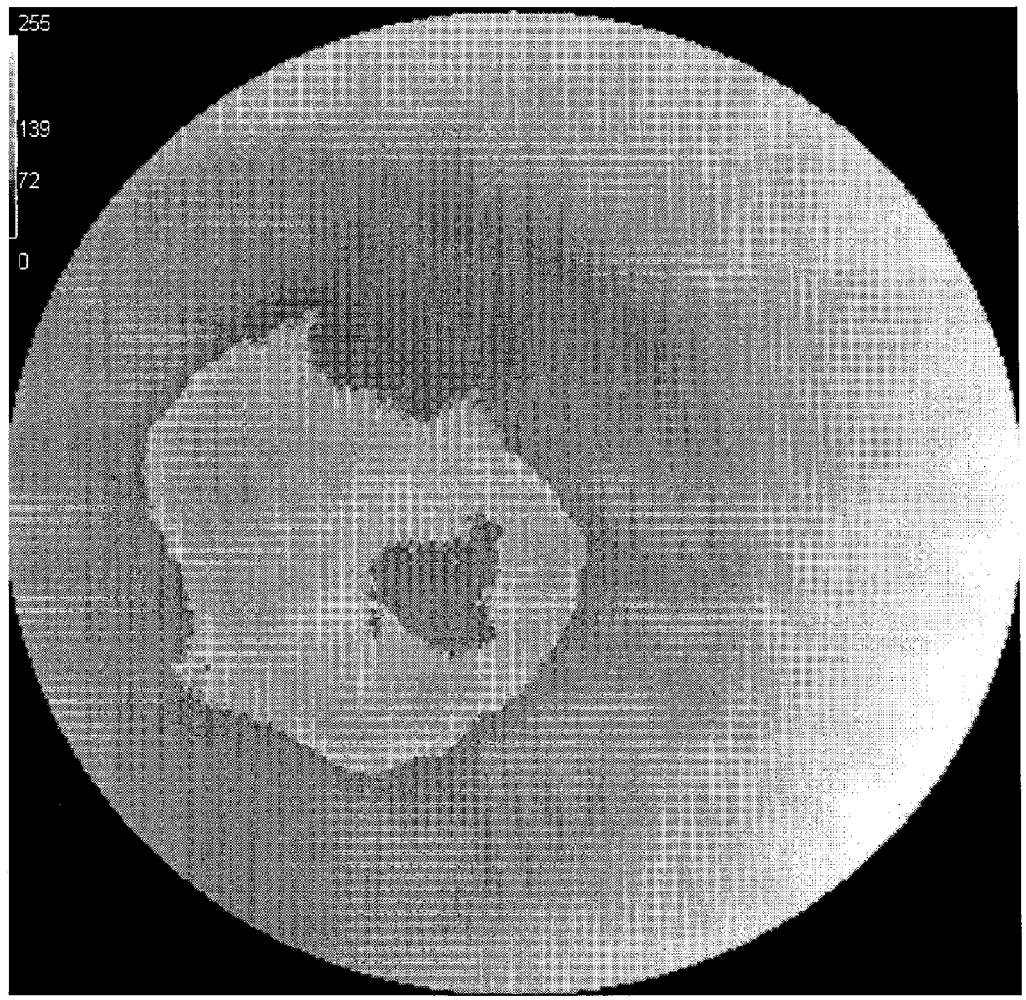
FIG. 10 is a section of a bone showing a singularity at a given resolution.
Figure 11:
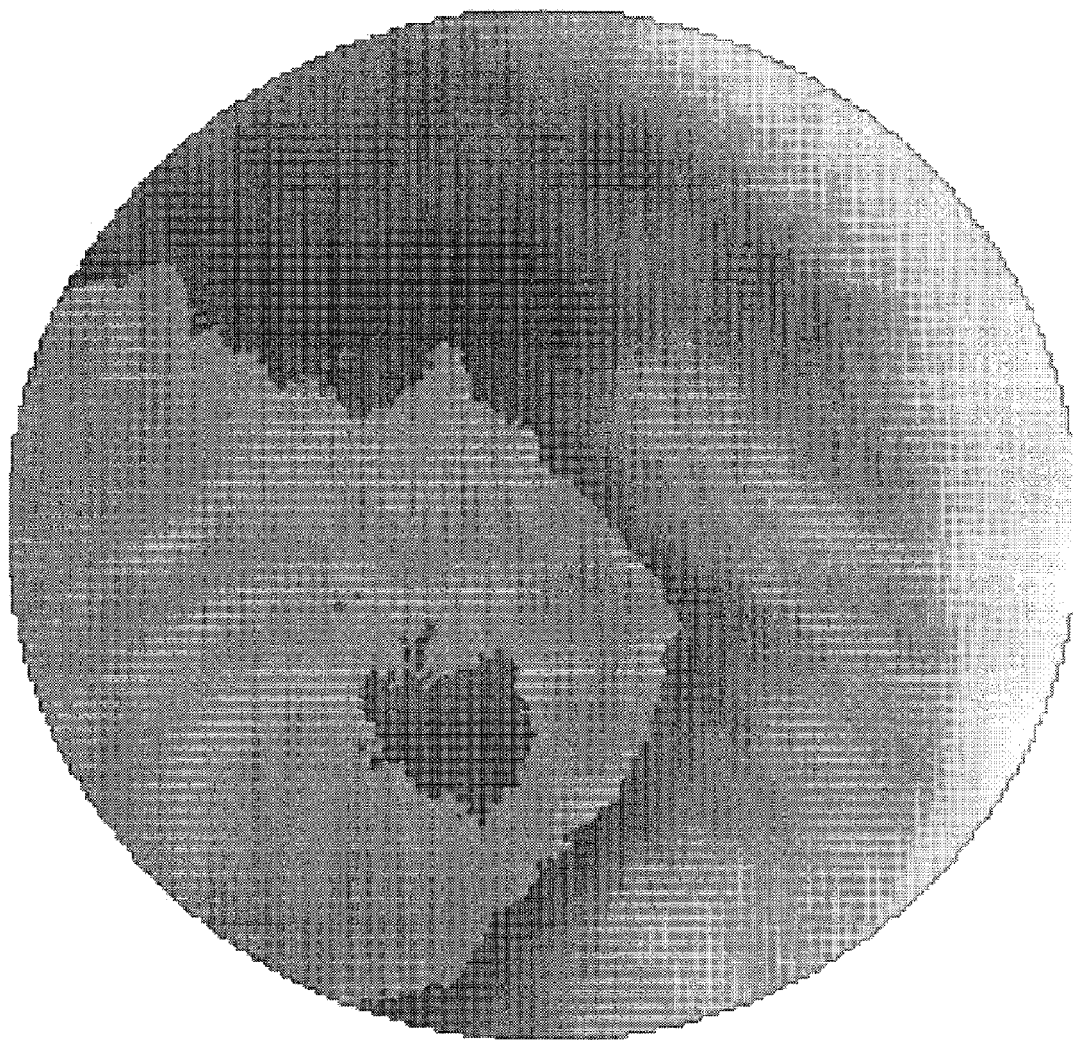
FIG. 11 is an enlargement of FIG. 10 showing the singularity at higher resolution.

In order to obtain a high definition image, it was necessary to create a software having the following functions:

acquisition and recording of the elementary images and the associated digital data, as shown in FIGS. 3a to 3d;

graphical definition of a band or section 75 of the area of the body 9 to be examined, irradiated by the beam from the X-ray source 11, perpendicular to the axis of rotation 19 of the support with respect to the source (see FIG. 9);

extracting from this section the values associated with the images located in the same plane, for example 36 slices made in 36 elementary radiographic images taken at 36 angles of rotation, from 0° to 360° in steps of 10°;

performing the calculations to generate in this case 36 images, by combining the values, two by two, for pairs of angles of rotation shifted by 90°;

rotation of the images according to the displacement, by an angle equal to the angle of rotation so as to superimpose the 36 images in a homogeneous manner;

formation of a synthesis image such as shown in FIGS. 10 and 11, which show a section of the chicken bone examined in the chosen plane, perpendicular to the axis of rotation and in which the band extends.

FIG. 10 is a section of a bone in which a slight spot can be seen that corresponds to a singularity due to the presence of a small metallic element. FIG. 11 is an enlargement that enables this metallic element to be examined more closely.

Figure 12:
FIG. 12 is another example showing a singularity at a resolution of 100 μm.
Figure 13:
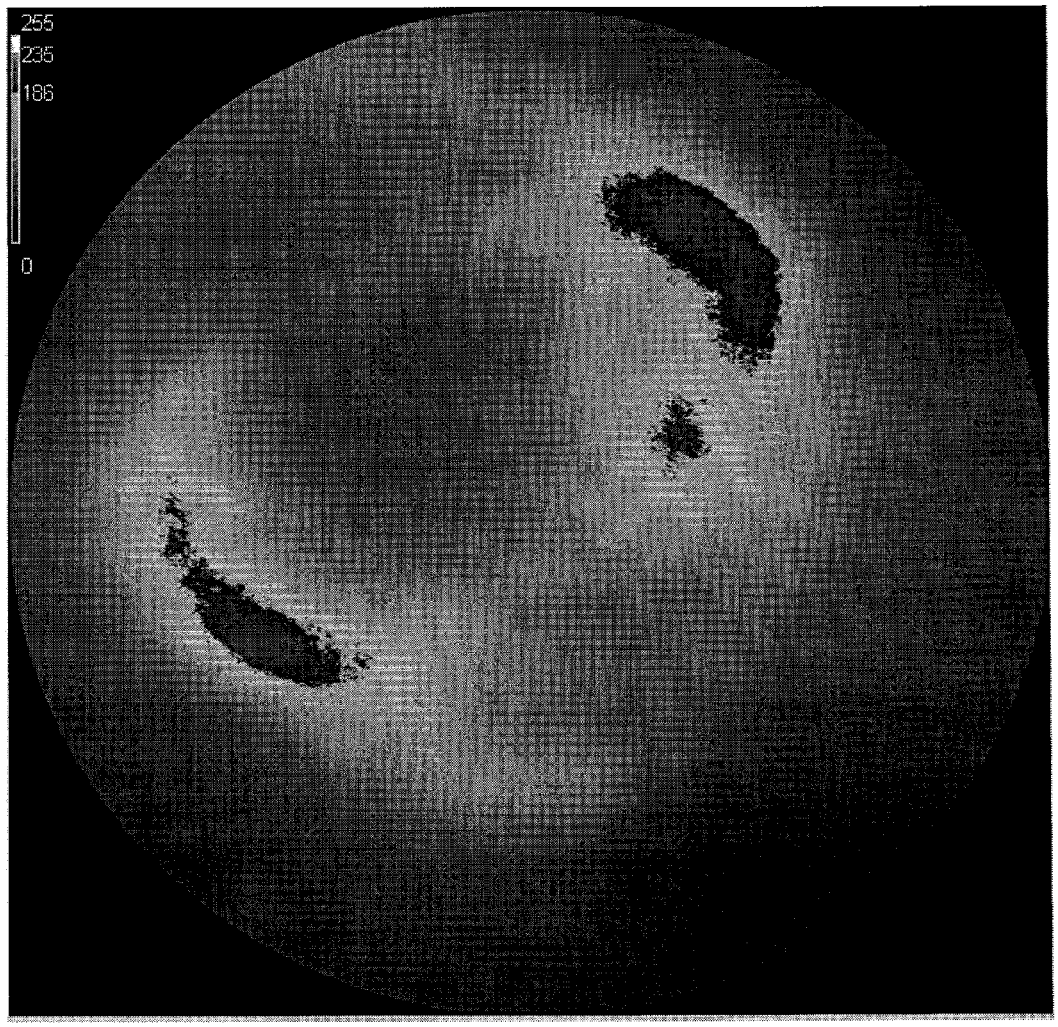
FIG. 13 is an enlargement of the singularity shown in FIG. 12, at a resolution of 25 μm.

Two synthesis images may be examined more accurately at definitions of respectively 100 μm and 25 μm for example. The first image, FIG. 12, shows the presence of metal balls in the examined bone. The second image, FIG. 13, enables the singularity to be examined in more detail.

It will be recalled that the term-by-term calculation is given by the formula:

$$Cij = Bij + \left(\frac{1}{n}\right) * \left(\rho j - \sum_{1}^{n} Bij\right) +$$
$$\left(\frac{1}{m}\right) * \left(ci - \sum_{j=1}^{m} Bij\right) - \left(\frac{1}{nm}\right) * \left(\sum_{j=1}^{m} \rho j - \sum ijBij\right)$$

For each pair of angles of rotation shifted by 90°, we have obtained a different image that can be combined by superimposing the different images after rotation in accordance with a procedure that will be explained here.

In fact, it is possible by means of a simple calculation to obtain a simple operator.

This operator is formed by the inverse matrix of the following matrix:

| COSINE A | −SINE A  | 0 |
|----------|----------|---|
| SINE A   | COSINE A | 0 |
| 0        | 0        | 1 |

We shall give an example, illustrated in the three tables hereinbelow:

Let us take for example a point having co-ordinates equal to, respectively, X=−2, Y=1, Z=0.

The following tables show the calculation procedure:

| ANGLE IN DEGREES | 270    |
|------------------|--------|
| ANGLE IN RADIANS | 4.7124 |
| SINE             | −1     |
| COSINE           | 0      |

| Initial matrix | | |
|---|---|---|
| 0  | 1 | 0 |
| −1 | 0 | 0 |
| 0  | 0 | 1 |

| Inverse matrix | | |
|---|----|---|
| 0 | −1 | 0 |
| 1 | 0  | 0 |
| 0 | 0  | 1 |

This matrix is multiplied by the vector X, Y, Z, which results in the following co-ordinates:

X'=−1; Y'=−2, Z'=0

In the case discussed above we have established a shift of the axis of rotation and effected a rotation of this axis, see the tables shown in FIGS. 14a to 14d, to obtain its co-ordinates in each table shifted by 90°, 180°, 270°, so as to re-centre the tables and obtain an ad hoc synthesis image.

By taking these displacements into account, we have generated a 29×29 initial matrix (table shown in FIG. 7) and a result matrix (table shown in FIG. 8).

The table shown in FIG. 7 is obtained after rotating the resultant matrices so as to recreate and re-centre the tables of results with the following angles of rotation.

0° for the graph 90-180,

270° for the graph 90-180,

180° for the graph 180-270,

90° or the graph 270-0.

These rotations have been simplified by using a simple matrix operator shown below:

| 0 | 0 | 0 | 1 |
|---|---|---|---|
| 0 | 0 | 1 | 0 |
| 0 | 1 | 0 | 0 |
| 1 | 0 | 0 | 0 |

The initial matrix is then multiplied by this operator and the resultant intermediate matrix is then transposed in order to obtain the initial matrix rotated by 90°.

A rotation of 270°is thus the result of three successive rotations of 90°.

In other words, in order to superimpose the result matrices obtained for two pairs of angles, for example the pair 0°-90°, and the pair 10°-10° that has turned by 10°, the result matrix obtained for 10°, 100° must be rotated by an angle of the opposite sign, in this case −10°. Preferably a pre-positioning method is employed in order to handle this rotation automatically and quickly. This method is illustrated with the aid of the tables given in the figures.

FIG. 15 shows the result matrix of the values Cij adjusted from the line and column constraint values obtained for the two perpendicular directions of propagation of the X-ray beam at respectively 100 and 100°.

In order to superimpose these values on those obtained for the two directions of propagation at respectively 0° and 90°, the matrix of the adjusted values Cij must be turned by −10°. In order to effect this rotation, one starts by expanding the matrix of size [5,5] into a matrix of size [3,25], where in FIG. 16 the three lines correspond respectively to the x co-ordinate of the point of the elementary zone of the grid consisting of 25 elementary zones, the value of which is Cij, to the y co-ordinate of the point, and to the z co-ordinate of the point. The [3,25] expanded matrix may then be multiplied by the aforementioned rotation operator, of size [3,3], FIG. 17, to arrive at the [3,25] rotated matrix. The rotated co-ordinates X', Y' and Z' have at each point non-integral values. These non-integral values are then rounded up, FIG. 18, to obtain integral values X", Y" and Z" of these rotated co-ordinates. This change of co-ordinates X, Y, Z to X", Y", Z" is carried out once for all values. In this way the pre-position of co-ordinates (X", Y", Z") corresponding to a rotation of −10° of this matrix is assigned to each adjusted value Cij of the point with co-ordinates X, Y, Z in the matrix (10°, 100°). The effect of rounding up the co-ordinates X', Y', Z' to X", Y", Z" is negligible.

The method that is the subject of the invention is preferably implemented in the following way:

stage (1) is carried out for a first group of four pairs of angles of rotation that are preferably mutually orthogonal (0°-90°; 90°-180°; 180°-270°; 270°-360°) in order to construct four column generating vectors each having as co-ordinates the n mean values obtained for the first angle of rotation (0°; 90°; 180°; 270°) and four line generating vectors each having as co-ordinates the m mean values obtained for the second angle of rotation (90°; 180°; 270°; 360°) of each of the four pairs of angles;

the four column generating vectors and the four line generating vectors are processed by a rotation operator in order to superimpose them on the same pair of angles of rotation (0°-90°), following which a reduced column generating vector and a reduced line generating vector are constructed by averaging, term by term, the homologous co-ordinates of the column generating vectors and line generating vectors superimposed on the same pair of angles of rotation (0°-90°);

stage (2) is carried out with the terms of the reduced column and line generating vectors;

stage (3) is carried out to obtain an adjusted matrix for which the line and column boundary values calculated for the adjusted values (Cij) are equal, respectively, for each line and column, to the terms of the reduced line and column generating vectors, and the stages (4) and (5) are carried out for different groups of four pairs of angles of rotation, shifted by a multiple of a reference angle (10°) with respect to the angles of rotation of the pairs of the first group.

This preferred mode of operation enables the calculation time to be reduced, as may be seen from the following example taken for 36 images.

The generator vectors of the matrices are grouped in a group I consisting of the line and column generator vectors of the unchanged 0°-90° matrix, the line and column generator vectors of the 90°-180° matrix, these vectors having been rotated by 90°, the line and column generator vectors of the 180°-270° matrix, these vectors having been rotated by 180°, and the generator vectors of the 270°-0° matrix, these vectors having been rotated by 270°.

These four line and column generator vectors are grouped respectively in a line generator vector and a column generator vector whose terms are equal to the sum of the homologous generator vectors divided by four.

An initial matrix and an adjusted matrix are generated, which correspond to the superpositioning of the 4 matrices in which the terms have been divided by 4.

The 10°, 100°, 190°, 280° vectors are grouped in a group II so as to generate the line vector of the synthesis matrix of the group 2, and the 100°, 190°, 280°, 370° (10°) vectors are grouped so as to generate the column vector of the synthesis matrix of this group 2, etc.

Nine intermediate synthesis matrices are thereby obtained, which are superimposed after rotating the whole set of matrices by appropriate angles:

matrix group I: unchanged
matrix group II: 10° rotation
matrix group III: 20° rotation
matrix group IV: 30° rotation
matrix group V: 40° rotation
matrix group VI: 50° rotation
matrix group VII: 60° rotation
matrix group VIII: 70° rotation
matrix group IX: 80° rotation Under these conditions the calculation time is divided by 4 for the rotations, without counting the simplifications introduced in the generation of the matrices. In addition the error calculation shows that much higher levels of accuracy can be achieved than in the case where 36 matrices are generated and aggregated, on account of the reduction in the number of rotations.

One may also consider using only 4 groups, the group I corresponding, starting from the point 0, to the four angular displacements 0°, 90°, 180° and 270°, grouped in a matrix displaced by 0°, the group II corresponding to the angular displacements 30°, 120°, 210°, 300°, grouped in a matrix displaced by 30°, the group III corresponding to the angular displacements 60°, 150°, 240°, 330°, grouped in a matrix displaced by 600°, and the group IV corresponding to the angular displacements 90°, 180°, 270°, 360°, grouped in a matrix displaced by 90°.

Four synthesis matrices are thereby generated, three of which undergo a rotation in order to obtain the final synthesis matrix. The final synthesis matrix is thus obtained after only 3 rotations instead of the 35 in the step-by-step case. An accuracy will then be obtained that is comparable to that obtained by using 36 matrices. The calculation time should thus be divided overall by 12, without counting the saving in calculation resulting from the new methods of generating matrices. In particular, the initial matrix may be obtained from two reduced vectors, one corresponding to the lines and the other to the columns. The terms of the first vector are derived from the terms of the constraint vector by dividing by the factor $2*n$. Likewise, the terms of the second vector are derived from the terms of the column constraint vector by dividing by the factor $2*m$. Thus, each of the terms of the matrix is only the sum of the two terms of the corresponding reduced vectors. This method is applied in a similar way to the result matrix. For very large matrices, this procedure enables the calculation time to be considerably reduced since the formation of each term only involves additions.

One may also consider using intermediate values, for example with shifts of 15°, and grouping them in groups of 4, i.e. the pole matrices 0°, 15°, 30°, 45°, 60°, 75°, or 6 groups of matrices representing 24 base matrices. The number of rotations is reduced to 5 and the accuracy is better than in the present case with 36.

Figure 19:
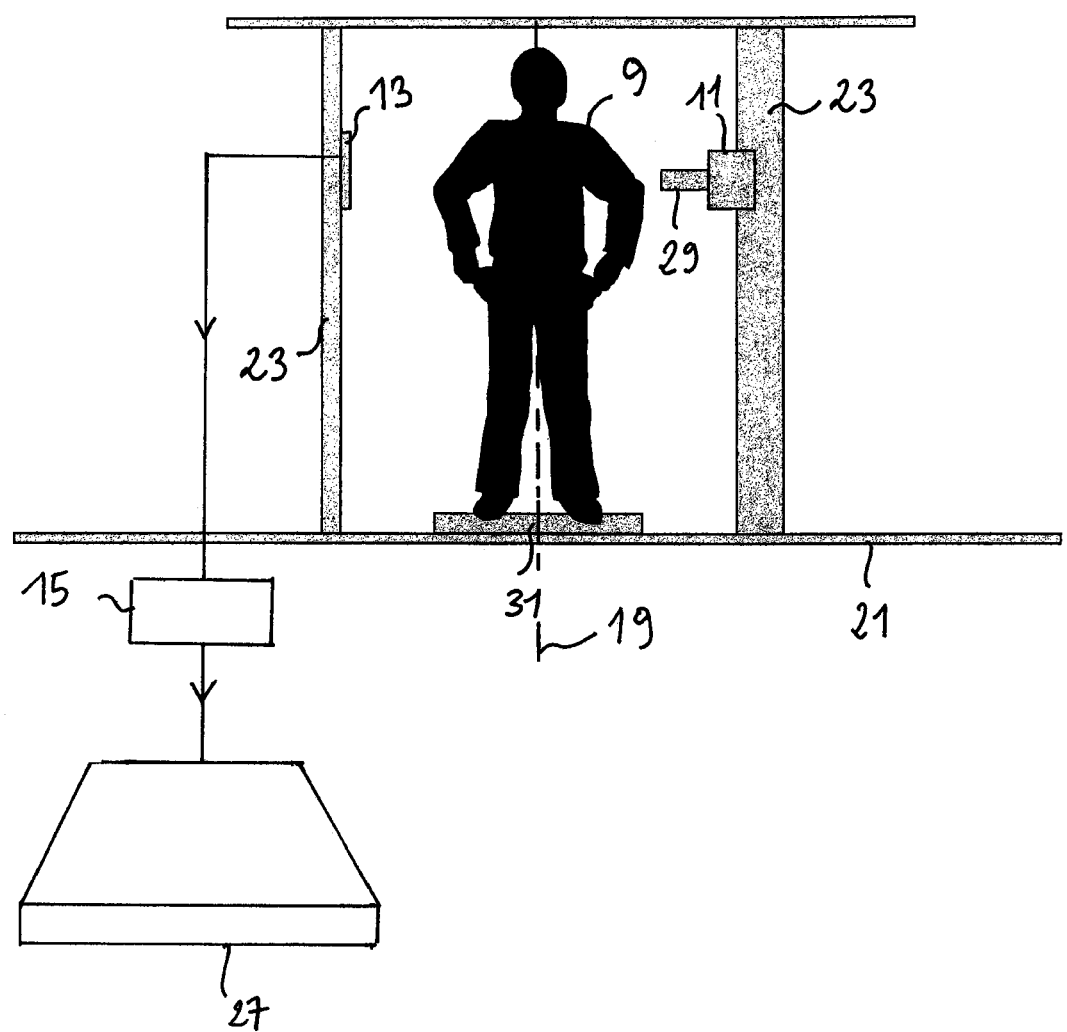
FIG. 19 shows diagrammatically a second apparatus according to the invention.
Figure 20:
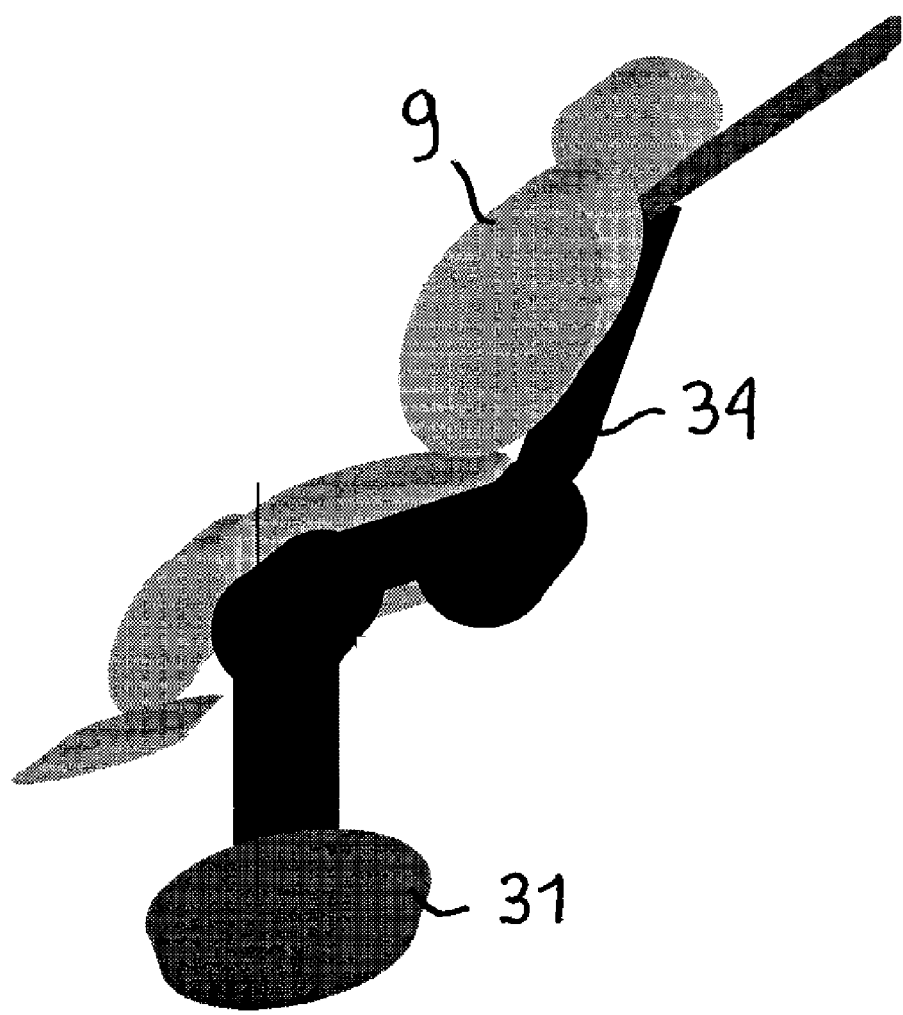
FIG. 20 shows more specifically an armchair used in the second apparatus.

The result of this work shows that a new type of X-ray or infrared imaging apparatus can be envisaged, as illustrated in FIG. 19 and consisting of the following:

a rotating base 31 on which a person (or an object) to be examined is placed. The persons normally stand on the base, but if they are unable to stand they can be placed on an articulated chair in order to enable them to sit while remaining inclined so that the region to be examined can be conveniently scanned by adjusting the chair; for some patients it is possible to sit on an articulated armchair 34 transparent to X-rays and that can turn when the images are being taken, as illustrated in FIG. 20;

a beam emitted by an X-ray source 11 along a horizontal axis that is movable on a vertical support 23;

a detector 13 that can be moved vertically or horizontally along a vertical support 25 depending on the size of the region to be examined; instead of the support a lifting device may also be used, comprising a synchronised belt means supporting two plates holding the parallelepiped-shaped junction module. The rotation of the synchronised belt enables the junction module to be moved downwardly or upwardly. The lifting device is itself movable so as to move the junction module in a horizontal plane;

a computer 27 which instantaneously receives, through an analogue-digital converter 15, the information from the detector 13 for each of the flashes of the beam at the instant when the detector 13 and the beam are aligned on an axis crossing the axis of rotation 19 of the rotating base 31.

This apparatus may be completed by a second beam-detector pair arranged at 900 to the first pair and operating in a synchronous manner.

The functioning of this system may be as follows:
the rotating base 31 rotates in a stepwise manner in such a way that the angle of rotation enables exactly matching images to be taken. If for example the distance of the axis of rotation 19 to the detector 13 is 75 cm, then the latter will execute a complete circular rotation of the order of 4.70 m; if the detector 13 is a plate of size 23 cm, one-twentieth of a step will be sufficient in a single rotation to obtain 10 elementary images from couples or pairs taken at 900 with respect to one another; if the step is only 6 cm, the circular movement will be divided up more accurately into about 80 steps, enabling 40 images of the desired definition to be obtained. Even if the beam and the detectors are not arranged in a circle of the order of 4.70 m, images 47 cm wide and 10 cm high may be obtained by a geometrical treatment of the image obtained if they are brought close.

In the case where it is desired to examine regions that are vertically small the detector 13 will be placed in the horizontal position, whereas if it is desired to examine regions that are vertically larger, the detector 13 will be placed in the vertical position, and in some cases the patient will be positioned so as to be able to target well the zone to be analysed.

It may also be envisaged that the patient is moved vertically to a suitable level, enabling any part of the patient's body to be examined. This is in practice possible if the patient is seated on the articulated armchair 34 that can be moved vertically on a telescopic arrangement 33.

Figure 21:
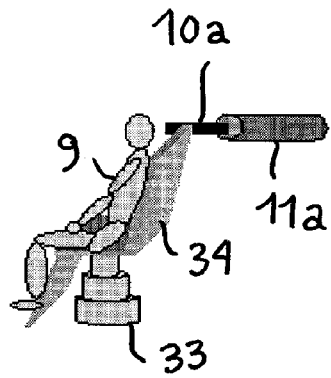
FIGS. 21 to 24 illustrate the use of the armchair mounted on a telescopic leg.
Figure 22:
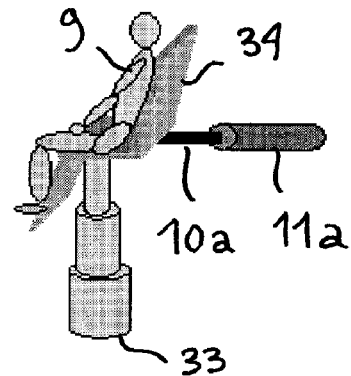
Figure 23:
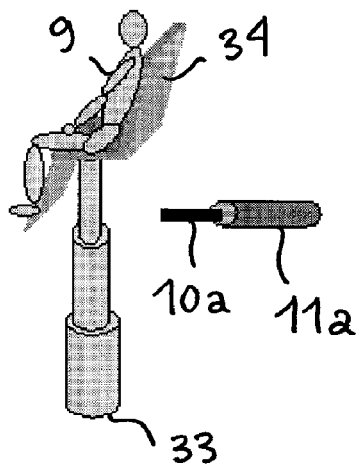
Figure 24:
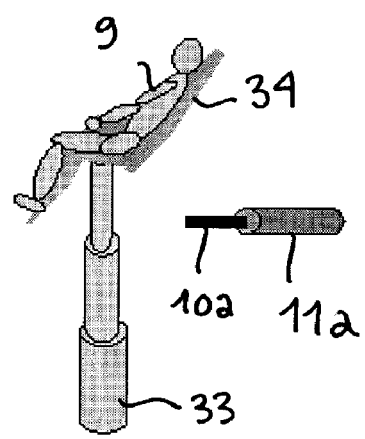

FIGS. 21 to 24 illustrate the functioning of the telescopic armchair: in FIG. 21 it is possible to scan the upper part of the patient, i.e. the head and shoulders; in FIG. 22 it is possible to scan the mid part, in particular the abdomen; in FIG. 23 it is possible to scan the lower part, in particular the legs. In the position shown in FIG. 24 the articulated armchair 34 can tilt slightly so as to limit the height of the telescopic arrangement to 2.40 m or 2.50 m.

However, other arrangements of detectors may be used for all specific applications without actually complicating the system.

The size of the detector 13 may be adjusted by using different detection plates, the cost of which is nowadays reasonable, in order to cover a whole range of possibilities.

It will be recalled that one rotation may be carried out in one minute without causing any harm, and in the considered case a volume of the order of 12 million pixels of information are collected 20 or 80 times, enabling a considerable number of densitometric sections to be obtained having the definition that the operator can specify as desired.

It is understood of course that the higher the definition, the longer will be the calculation time.

The operator will be able to choose his/her protocol once the images have been stored, so as first of all to obtain low definition or medium definition images and then refine the investigation for this or that part of the organism, by keeping the images created during the scanning, for the continuing investigation after the patient has left.

In any case, with low definition images these can be displayed on the screen a few seconds after the investigation, and if necessary the investigation can be extended to other regions of the investigated organism.

A human body generally has a maximum horizontal dimension of the order of 48 cm (in particular at the shoulders or pelvis). This presupposes that the detection plate has a size of the order of 48 cm and that the beam itself can have a horizontal dimension of 48 cm. Under these conditions the distance between the beam and detector would need to be at most of the order of 3.25 m. In fact, a circle 3.25 m in diameter has a circumference of the order of 10 m, if one wishes to obtain 20 images (the elementary angle must be of the order of 18°, i.e. an arc of about 50 cm and a chord of about 48 cm). The distance of 3.25 m between the beam and the detector is given by way of example, but images may be obtained at shorter distances by defining a dimension of the beam that is compatible, depending on the distance, with the size of the detector.

Figure 25:
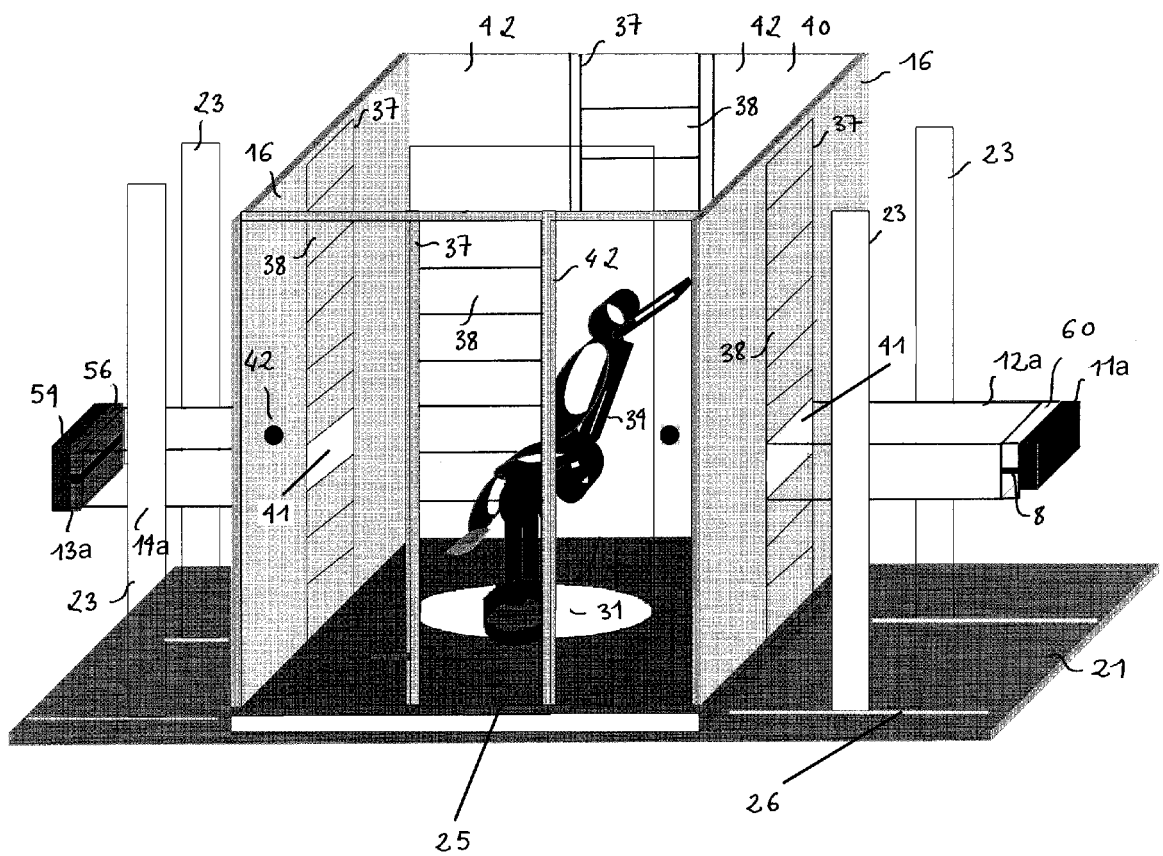
FIG. 25 shows diagrammatically a third apparatus according to the invention.
Figure 26:
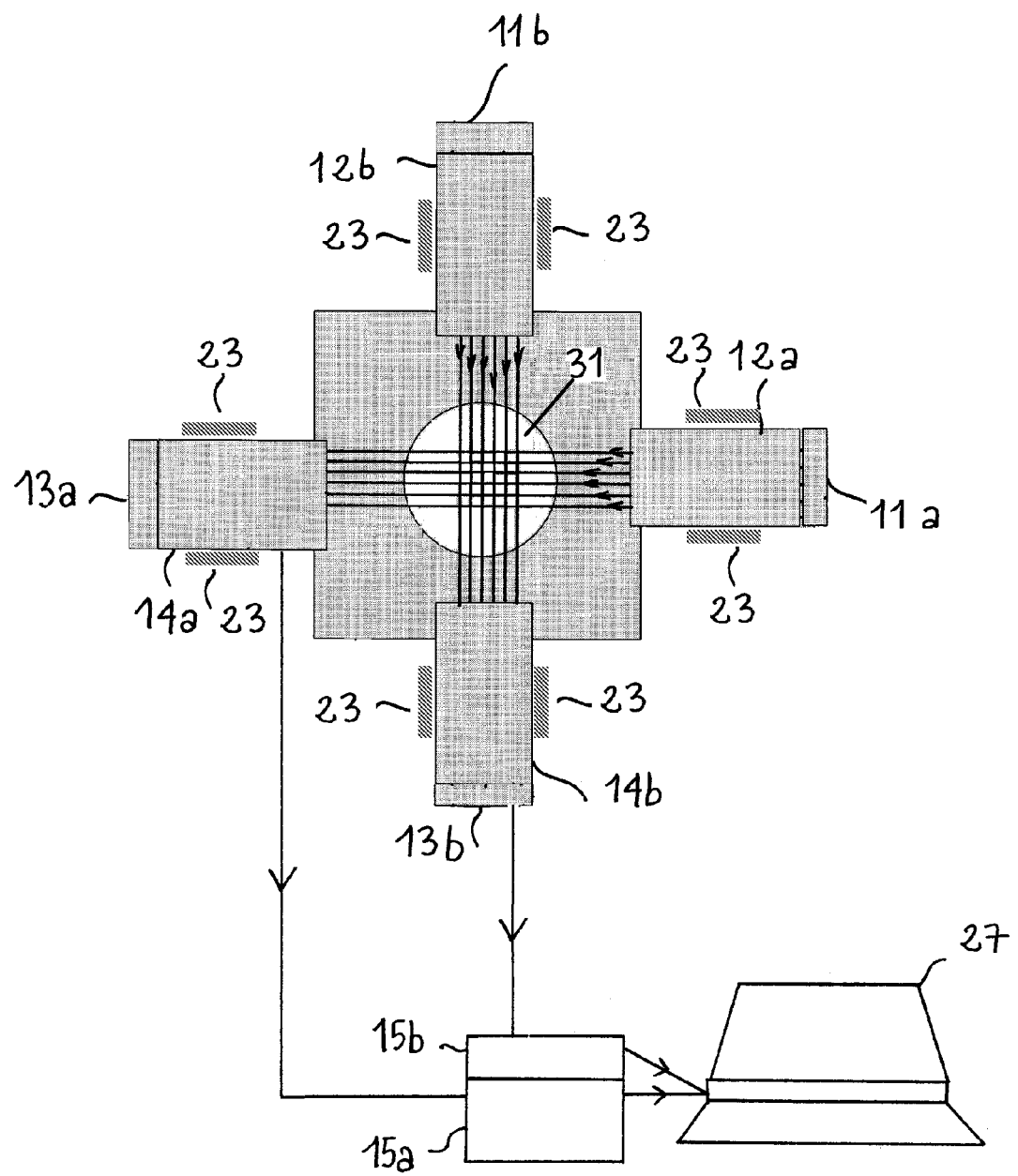
FIG. 26 is a view from above of the third apparatus.

From this first condition defining the geometry of the system for taking images, in order to obtain more than 36 shots with detection plates of size 48 cm, the choice has been extended to a geometry permitting 20 shots. The whole arrangement thus consists of a cabin of size 175×175×205 cm, or 190×190×205 cm providing an apparatus that is specially designed to implement a method according to the invention and comprising, as shown in FIGS. 25 and 26:

a cabin of size 175×175×220 cm, having a double rôle as a structure for accommodating the whole arrangement and protecting the environment against X-rays;

four junction parallelepipeds 12a, 12b, 14a, 14b for carrying the orthogonally functioning detectors and X-ray beam generators;

four double supports 23 enabling the parallelepipeds to be moved vertically and horizontally;

two detectors 13a, 13b mounted on the two parallelepipeds 14a, 14b;

two X-ray beam generators 11a, 11b mounted on two other parallelepipeds 12a, 12b;

an information processing system 27, receiving the data from the detectors so as to generate the elementary image and synthesis image;

a control panel for the whole arrangement of the kinematic functions.

The cabin is designed as a "double detection" cabin to take into account the speed of response of the detectors and unforeseen movements of the patient. The cabin is therefore provided with two identical beam generators, arranged at 900 with respect to one another and at exactly the same height at the moment the images are taken, which are synchronised. The cabin accordingly has the following design and construction:

a steel platform 21 of size 175×175 cm supporting the structure for securing the lead plates;

a lead platform 25 of size 175×175 cm placed on the steel platform at about 15 cm from the floor and capable of being dismantled so as to permit access to the electric motor for rotating an armchair 34;

a metal structure of steel corner pieces and steel tubes for supporting the lead plates;

at the front, a front wall comprising, in the centre, a gantry support 37 205 cm high, 55 cm wide, that can carry 20 panels 38 of size 52.5×10 cm that can slide vertically to prevent the presence of untreated zones between two levels; to the left and right of the gantry support is a lead glass door 42 205 cm high and 61.25 cm wide;

on the right-hand side, a wall comprising, in the centre, a gantry support 37 205 cm high and 55 cm wide that can carry twenty lead panels 38 of size 52.5×10 cm that can slide vertically upwards so as to prevent the presence of untreated zones between two levels; on the right and on the left, a lead wall 16 of size 205×61.25 cm;

on the left-hand side, a wall comprising, in the centre, a gantry support 37 205 cm high and 55 cm wide that can carry twenty lead panels 38 of size 52.5×10 cm that can slide vertically upwards so as to prevent the presence of untreated zones between two levels; on the right and on the left, a lead wall 16 of size 205×61.25 cm;

at the bottom, a wall comprising, in the centre, a gantry support 37 205 cm high, 55 cm wide, that can carry twenty panels 38 of size 52.5×10 cm that can slide upwardly vertically to prevent the presence of untreated zones between two levels; to the left and right of the gantry support is a lead glass door 42 205 cm high and 61.25 cm wide;

a lead ceiling 40 of size 175×175 cm that can support equipment for lifting the groups of sliding panels.

Figure 27:
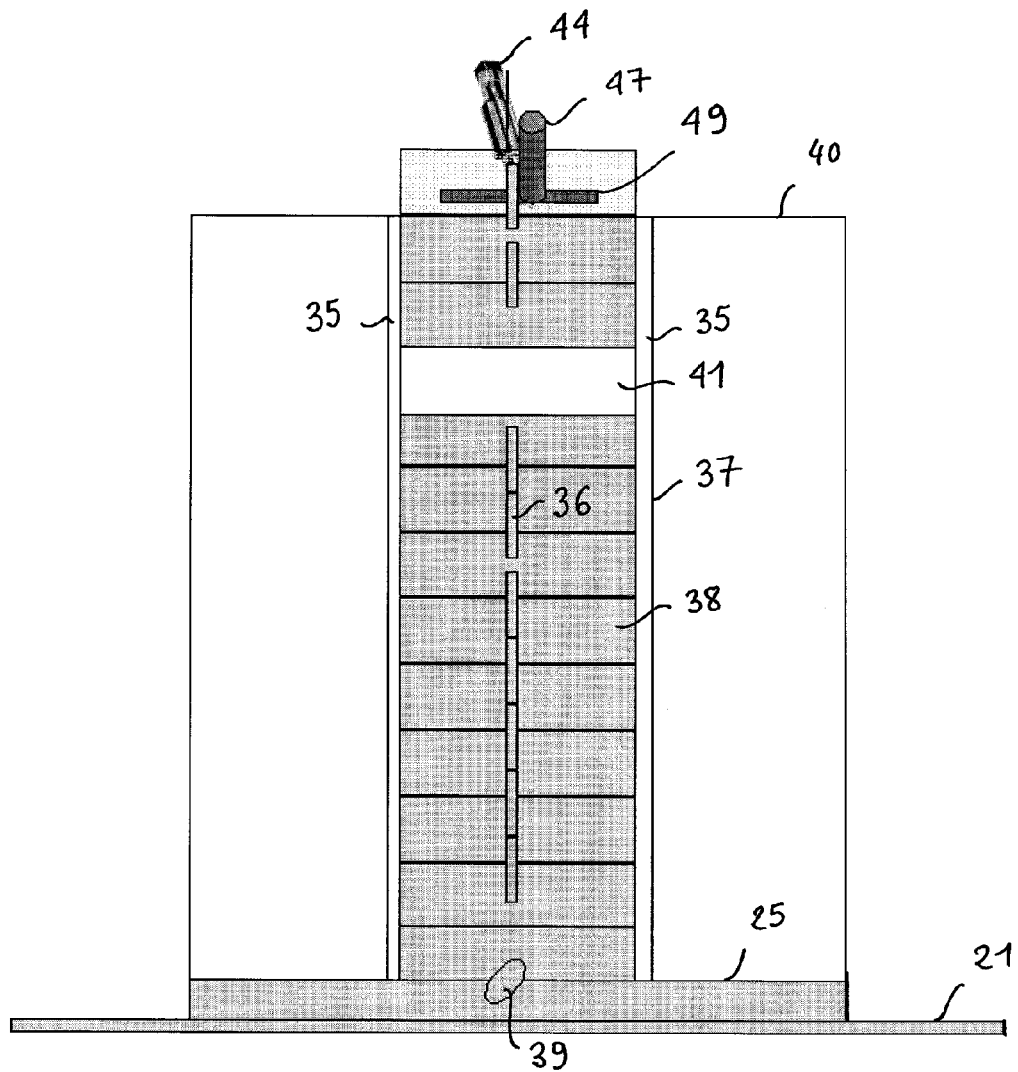
FIG. 27 shows diagrammatically the raising of the sliding panels mounted in a side wall of a cabin according to the third apparatus.

In order to take account of the problem caused by hinges that can allow X-rays to pass through, and the problem of an untreated zone located on both sides between two open zones, the panels 38 slide in vertical rails 35 protected by small L-shaped plates. In FIG. 27 they are raised as a group in order to open the specific window 41, and are joined together by securement elements 36 that can be opened and closed manually or automatically.

If for example three panels are combined, the set of three panels is raised by a height chosen by the operator in order to allow junction parallelepipeds to be inserted. The lower panels may also be raised so that the chosen zone can be any one in the system, thanks to a lifting cam 39. In this way a window 41 is simultaneously opened in the four central gantry supports of the cabin, at the same level, by synchronising the movements of the sliding panels. The mechanism enabling the group of combined panels to be raised is mounted on the roof 40 of the cabin. In order to facilitate maintenance, the lower plate 25 can be dismantled, thereby allowing access to the motor for driving the armchair on which the patient sits.

In order to allow the window 41 to be opened and the junction parallelepiped to be introduced into the cabin through the window, at least two procedures may be adopted:

a pulley mechanism driving by means of a metal wire a group of panels and comprising two winches on which metal wires are wound, each of the winches being driven by a stepping motor, for example from ORIENTAL MOTORS, the moment of which is of the order of 20 Newton-meters with a step of less than 1 degree; or a mechanism using screw jacks, such as manufactured by HOERBIGER. The screw jack is constructed as follows: on an endless screw secured at both ends is placed a metal bar connected to the endless screw by a tube having a step compatible with that of the screw. By turning the endless screw using an electric motor, a force of up to 1500 Newtons can be lifted at speeds that may be greater than several tens of centimeters a second. The screw jack 44 is accordingly arranged on a metal plate 49 integral with the roof 40 of the cabin and driven by a motor 47 of a suitable power that can operate in a pulsed manner, so as to effect the displacement in one or other direction within chosen limits or at chosen speeds.

Protection against a 200 kV X-ray beam is ensured by an excellent linkage of the doors and sliding panels.

As an example, the junction parallelepipeds have the following dimensions: internal height 10 cm, external height 10.8 cm, internal depth 52.5 cm, external depth 53.3 cm, and width 75 cm. The weight of each parallelepiped is thus of the order of 22 kg and each parallelepiped supports an additional weight that may be as high as 26 kg for the detector or the beam generator and the tunnel. It is envisaged that an arrangement of the order of 50 kg can be displaced vertically to an accuracy of ½ millimeter.

The double supports are mounted on rails 26 secured to the base plate 21 of the cabin so that they can be moved horizontally and thus allow the junction parallelepipeds to be introduced into the cabin through the openings 41 formed when the sliding panels 38 are raised. It is envisaged that a junction parallelepiped can be displaced horizontally with an accuracy of the order of 1 centimeter.

The junction parallelepipeds can move vertically along the double supports 23 so as to align the beam 11 and the detector 13 exactly opposite one another in the openings 41 of the central gantry supports formed by the raising of the sliding panels.

The horizontal dimensions of the cabin can be reduced, provided that the reduction is compensated by an increase in the lengths of the parallelepiped modules 12, 14. In the same way, in order to obtain a larger number of images it is possible to replace the parallelepiped modules by longer modules having the same shape. The choice of the length of the modules will depend on the desired accuracy, and in the case where the modules are oblong it will be necessary to provide more powerful X-ray beams and detectors of greater sensitivity. It will be understood that the parallelepiped junction modules 12, 14 enable the space occupied by the cabin to be reduced by bringing closer the front and bottom side walls of the rotating base 31.

Figure 28:
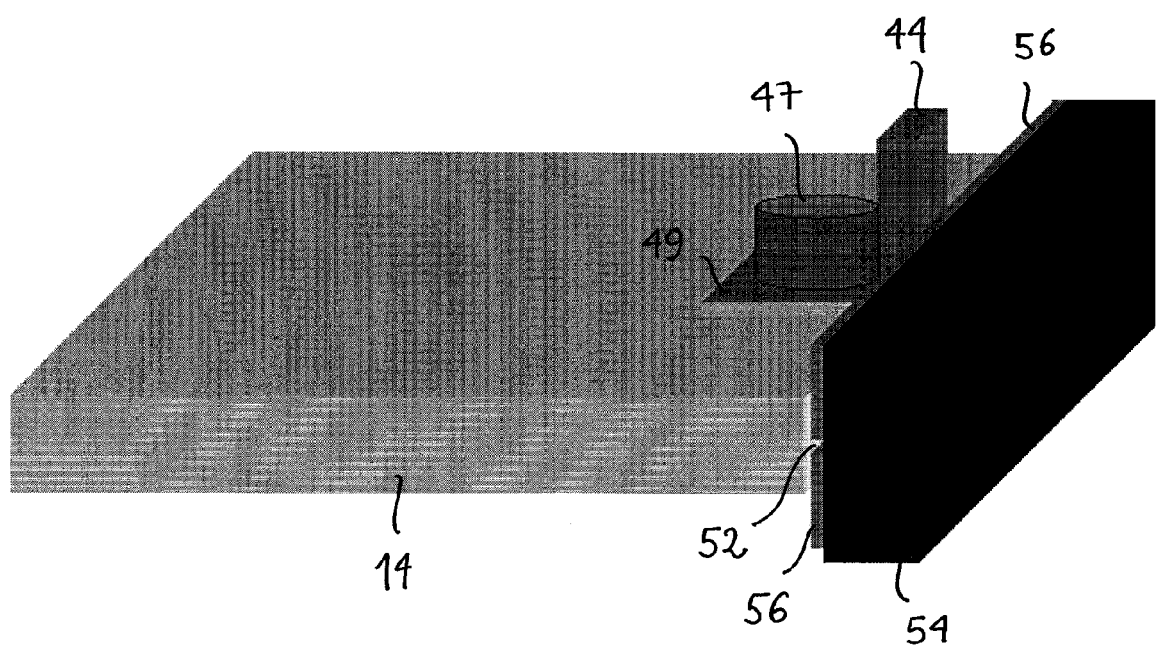
FIGS. 28, 29 and 30 show diagrammatically a detector used in the third apparatus, which can move with respect to a junction parallelepiped.
Figure 29:
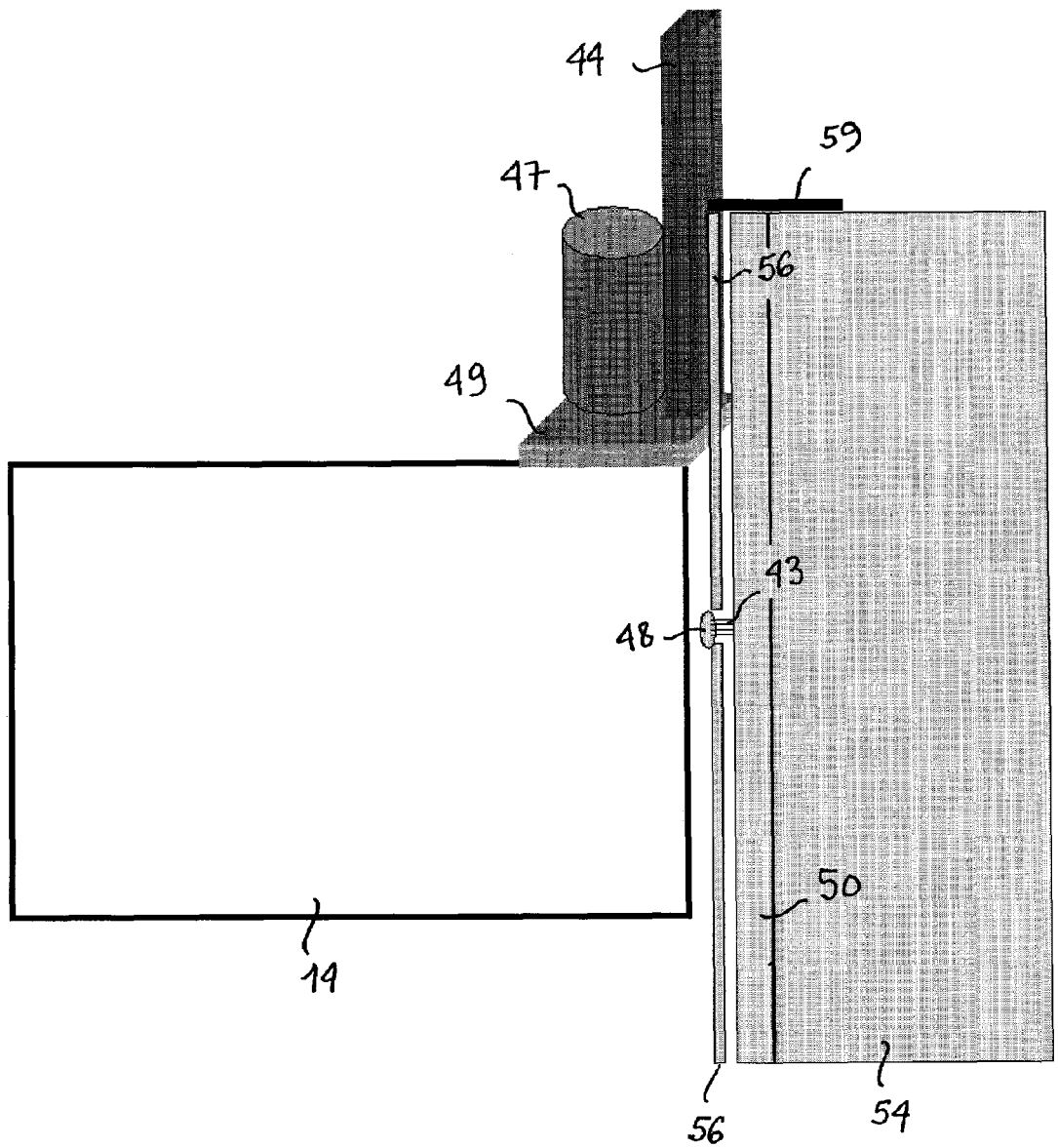
Figure 30:
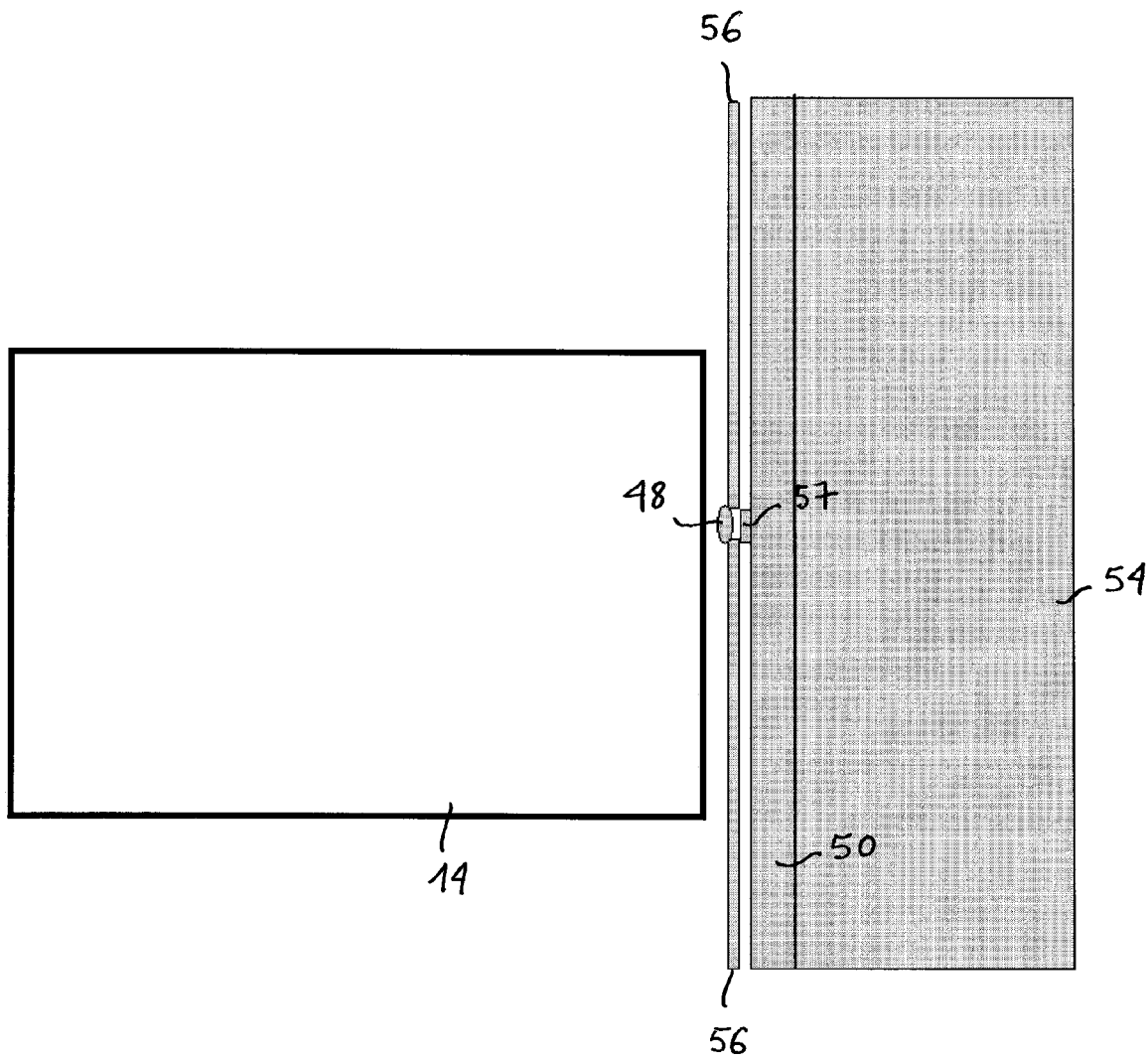

The detector 13, FIGS. 28 to 30, is secured to a plate 59, by being arranged at the external or internal end of the junction parallelepiped 14. Various types of detectors may be mounted on the plate. The detector 13 preferably comprises a double detection rod 48, for example of the ATMEL AT71957 type of size 23×0.6 cm, i.e. with a total width of 46 cm, a support 50 for the double rod joined by connections 43 to an electronics unit 54 enabling analogue data to be converted into digital data, the digital data to be stored in a buffer memory, the data to be transferred to a computer in the form of a matrix consisting of lines whose equivalent physical dimension is of the order of 46 cm, the lines being 27 microns apart, and thereby being able to generate a matrix corresponding to a geometry of the order of 10×46 cm. This electronics block has an approximate size of 50×20×5 cm.

In order to protect the electronics arrangement 54 two lead plates 56 are secured to the support 50, leaving a gap of about 1 cm between them, thereby forming an aperture 52 for the double detection rod 48. A plate 57 of small width is also arranged behind the two detection rods 48.

In order to prevent the presence of black zones between the two rods, estimated to be 1.4 cm, the patient can be moved so that the axis of rotation of the articulated armchair 34 does not coincide with the axis of intersection of the orthogonal beams. First of all the electronics unit 54 is moved 0.7 cm to the left of the central sectional axis, the unit is then moved 0.7 cm to the right of the axis, and a vertical scanning is then carried out again in order thereby to obtain two images that can be superimposed by information processing techniques so as to obtain a final image without any black zone.

The detector 13 is mounted so it can be moved with respect to the junction module 14 by means of a motor-driven screw jack mechanism 44, 47 of the type described for raising the panels 38 sliding in the central supports 37. The motor-driven screw jack is fixed to the junction module 14 by means of a force-absorbing plate 49.

Figure 31:
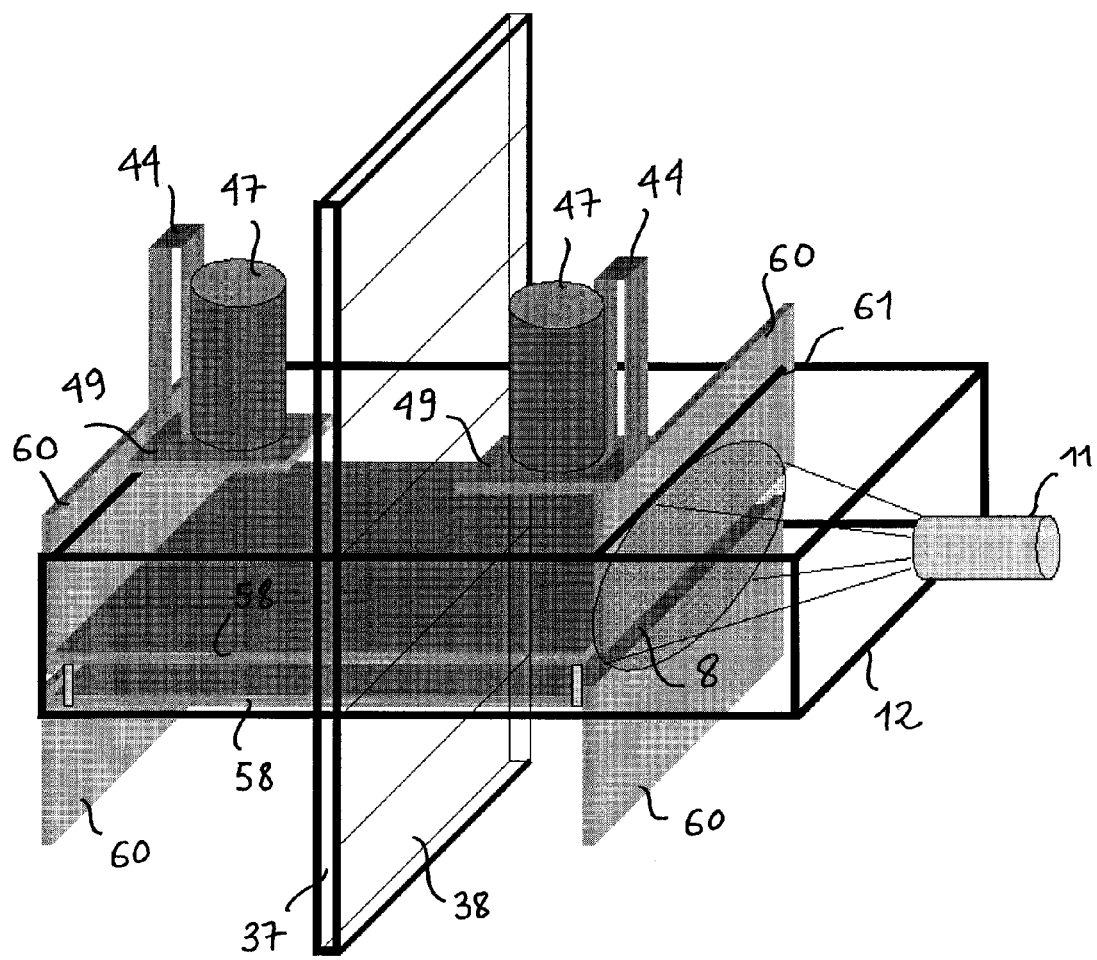
FIG. 31 shows a particular arrangement of a junction parallelepiped equipped with a collimator.

The X-ray beam generator 11, FIG. 31, is fixed to the junction parallelepiped 12 by means of two plates 60 inserted respectively through an upper window and a lower window 61 of the junction parallelepiped, a short distance from the outer end.

Several types of X-ray beam generators may be mounted on the said plate. A beam generator may thus be used having an integrated high voltage transformer fed by a voltage ranging for example from 40 to 110 kV and with an output of 3200 Watts, operating at sequences of a few seconds. A beam generator of this type may also be used, operating at a voltage of 125 kV, an output of 30,000 Watts, and at sequences of 1 millisecond to 1.6 seconds. Preferably a beam generator is used supplied with a voltage of 160 kV and with a continuous output of 4000 Watts, having an active electrode of 4 mm cooled by circulating oil, which is itself cooled by an oil/water heat exchanger.

An aperture 8 about 1 cm high and about 48 to 50 cm wide is formed between the plates 60, corresponding to the 1 cm size aperture 52 formed by the separation gap of the two protection plates 56 of the detector 13. This arrangement has the advantage that it restricts the amount of radiation received by the patient to what is just required to irradiate the detection rod 48 of the detector 13.

Preferably a means for collimating the X-ray beam within the junction module 12 is provided, in order to reduce still further exposure to X-rays. This collimating means comprises the two plates 60, two similar plates 60 arranged at the opposite end of the junction module 12, and two horizontal plates 58 extending into the interior of the junction module and each being secured, for example by welding or bolting, to the two end plates 60 so as to form a collimating tunnel. This arrangement is vertically movable with respect to the junction module 12 on which the X-ray beam generator is secured, in order to scan the height of the module. The movement of the collimating tunnel with respect to the junction module 12 is in this case effected by one or two motor-driven screw jacks 44, 47 of the type of motor-driven screw jack described for the movement of the panels 38 sliding in the central gantry supports 37. The motor-driven screw jacks are fixed to the junction module 12 by means of a force-absorbing plate 49.

The two horizontal plates 58 are of molybdenum-containing lead about 2 to 4 mm thick. They are spaced apart by a gap of the order of 1 cm, so as to form the collimating tunnel for the X-ray beam. An X-ray beam of small thickness is thus produced, so as to restrict the amount of radiation received by the patient.

In the same way a collimator may be provided in the junction module 14 of the detector 13 so that the X-ray beam exactly touches the detection rod 48 of the detector.

Inside the cabin, a rotating base 31 whose rotation is motor-driven is mounted on the horizontal plate 25. The rotational movement can be programmed in order to produce one or more complete rotations with step-by-step angles of rotation defined by the program. A device for immobilising the patient 46 or alternatively an articulated armchair 34 is provided, fixed to the base 31, of a material transparent to X-rays and on which straps may be attached for immobilising the patient.

The composite material consists of lead sheets 2 to 4 mm thick, enclosing polyethylene sheets 4 mm thick with a polyethylene coating on the inner surfaces.

The control panel is provided for carrying out the following operations:
positioning the four junction parallelepipeds at the same horizontal level;
opening an examination space of the order of 20 cm by raising the sliding panels;
introducing the junction parallelepipeds and their means for blocking the X-ray beams;
re-closing the panels accurately on the junction parallelepipeds;
controlling the simultaneous movements of the beams and detectors over a height of 10 cm in order to produce two synchronous images, which operation should take of the order of 2 to 4 seconds. If necessary the detector may operate with two repeats in the vertical direction, with a gap of 1.4 cm between the two positions; controlling the operation of the beam and specifying in particular the duration of the flash;
rotating the patient by an angle of for example 10° or more;
repeating the previous operations at a new angle;
restarting the sequence between 12 and 36 times so as to obtain the generating base images of the synthesis image.

The set of the commands is organised timewise so that they can be controlled by different protocols.

The information processing system enables data to be obtained from the detectors and processed in accordance with the following sequence:
conversion of the analogue data to digital data, which conversion can be carried out by a special chip integrated in the detector, and
storage of the digital data on a disk of sufficient size;
possibility of cloning the disk so that the information can be transmitted to different interested operators by means of a software capable of producing the various images of the scanned sections, according to the requirements of the medical investigation.

The possibility of having two beam-detector sets displaced by 90° enables images consisting of information taken at the same instant to be obtained in a few fractions of a second. In about 2 to 3 seconds, the time of a rotation, 10 or 40 images may be obtained of this or that part of the organism, and in this case there is a possibility of producing a series of images staggered by a few fractions of a second and with high scanning rates.

It is clear that the cabin may also be designed simply for the purposes of detection. In this case only a single X-ray beam and a single detector are provided.

Means for filtering and linearising the X-ray beams are provided in the junction modules.

The installation of aluminium filters intended to linearise the X-ray beams also has an effect on the amount of X-rays reaching the patient.

As regards the irradiation of the operators and patients, the cabin completely protects the operators and the double detection system enables more information to be obtained with the same amount of X-rays, or the same amount of information with fewer X-rays.

In fact, for a stepped rotation of 18°, the cabin with a double detection arrangement enables 20 synchronous images to be obtained thanks to the double detection, as well as 40 non-synchronised images, 20 per detector. In other words, 60 images are obtained with only 40 radiation doses of the patient, whereas with a simple detection cabinet 60 radiation doses are received by the patient in order to obtain 60 images. It can be seen that the double detection cabinet reduces by one-third the level of radiation for the same number of images.

The modus operandi is as follows for a given protocol:
the orthogonal beams 11*a*, 11*b* and the corresponding detectors 13*a*, 13*b* are moved to the same initial height with respect to the floor platform 21. This movement is carried out by means of the two double supports 23 so as to position the junction modules 12, 14 opposite to the sliding panels 36 of the central gantry supports 35 situated at the same height with respect to the floor platform 21;
the sliding panels 36 are displaced vertically in the central gantry supports 37 so as to open a window 41;
the junction modules 12, 14 of the beams and of the detectors are moved horizontally through the windows 41 by means of the rails 26 so that the outlet end of the X-rays from the junction module of the beams and the inlet end of the X-rays in the junction module of the detectors 13 are brought close to the patient seated in the articulated armchair 34. The position of the junction modules is adjusted through the windows 41 by means of the lifting cam 39;

the beams 11a, 11b and the detectors 13a, 13b are vertically moved with respect to their respective junction modules 12, 14, the latter remaining fixed in position with respect to the support 23 during this movement. The motor-driven screws 44, 47 are employed for this movement. These two movements are carried out synchronously with the same rate of movement so as to harmonise the aperture 8 formed between the plates 60 of the collimating tunnel arranged in front of the beams 11a, 11b, with the aperture 52 formed by the separation gap between the two lead plates 56 of the detectors 13a, 13b. During these two movements the aperture 8 of the beams 11 and the aperture 52 of the detection rod 58 traverse the whole height, amounting to 10 cm, of the junction modules 12, 14.

In the apparatus described above the junction modules 12, 14 have a height of 10 cm so as to reduce the size of the protection plates 56 of the electronics unit 54 and the weight that has to be vertically moved. Taking into account the performance of the electronics unit, the rate of movement varies for example between 1.5 and 5 cm per second during the acquisition of the data, but may be faster in order to return the whole arrangement to a low or high position without recording the data;

during the synchronous movement of the beams 11a, 11b and of the detectors 13a, 13b with respect to the junction modules 12, 14, an image of size 10×46 cm is obtained in 2 to 6 seconds;

the patient is turned in order to obtain successively 20 images staggered with respect to one another by an angle of 18°. 20 images staggered with respect to one another by an angle of 18° are also obtained symmetrically on the other beam-detector set arranged in an orthogonal manner. 60 images can then be used, divided up into 20 synchronous images, two by two, one image coming from one of the detectors 13a and the other from the other detector 13b, 20 asynchronous images on the detector 13a and 20 asynchronous images on the detector 13b, i.e. a total of 60 usable images. The whole rotation process will take of the order of 60 seconds.

These images are then processed in order to obtain images having the desired definition. It will be recalled that over a height of 10 cm with a definition of 25 microns, images may be formed with multiple definitions of 25 microns, by information technology superpositioning of the data. In such a case the images may be produced with lower definitions, with the possibility of zooming over the whole of the chosen zone or over a series of zones located in the cylinder of the zoom.

Figure 32:
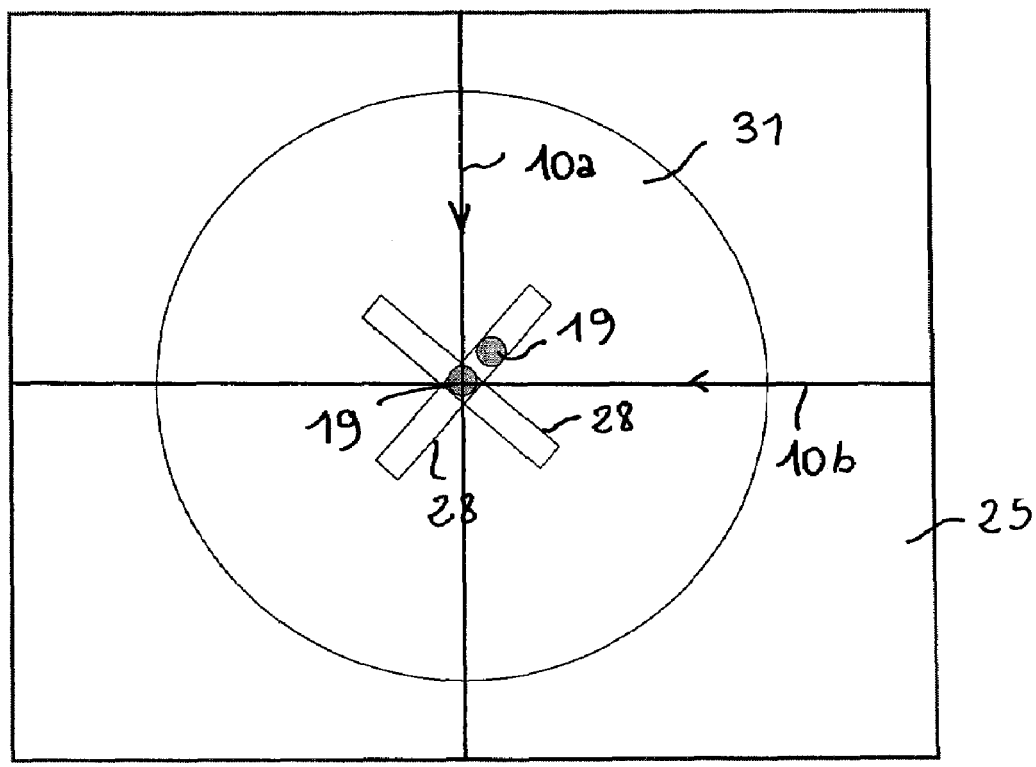
FIG. 32 shows diagrammatically an eccentric arrangement of the axis of rotation of the third apparatus.

The rotation of the patient may be effected in at least two ways:

positioning the axis of rotation 19 at the intersection of the two beams 11a, 11b, which is capable of creating a dead zone situated on this axis, and the diameter of which would be of the order of 1 cm; positioning the axis of rotation 19 eccentrically by movement along a groove 28 fixed to the platform 25, as illustrated in FIG. 32.

The armchair 34 itself may also be arranged eccentrically, provided that it is placed on a slide means attached to the pivoting tube of the articulated armchair.

Some facts and figures will be recalled here: the weight of the patient may be up to 120 kg, the weight of the armchair together with the joints could be up to 20 kg, which is why the rotation motor should drive a solid robust plate, supporting the axis of rotation, which itself supports the armchair. This solid robust plate may be situated underneath the platform and have the same dimensions as the grooves, so as to protect the motor situated underneath as well as all its control systems.

The junction modules 12, 14 are moved in the opposite direction on the rails 26 in order to retract the windows 41, which are re-closed by vertically lowering the sliding panels 36 in the central gantry supports 37 so as to close the cabin with respect to the beams 11 and the detectors 13;

the junction modules 12, 14 are moved vertically so as to align them opposite to the sliding panels 36 arranged at a second height with respect to the floor plate 21;

the junction modules 12, 14 are moved horizontally on the rails 26 through the newly-opened windows 41, so that the end of the outlet of the junction module of the beams 11 as well as the end of the inlet of the junction module of the detectors 13 are brought close to the patient. The position of the junction modules is adjusted through the windows 41 by means of the lifting cam 39;

the beams 11 and the detectors 13 are moved again with respect to the junction modules 12, 14 adjusted to a second height, and the acquisition of the 60 images is carried out again according to the procedure described hereinbefore with regard to the first exposure height.

It goes without saying that it is perfectly possible to use smaller detectors, in which case the images would be situated in a cylinder the diameter of which is a function of the width of the detector.

The sequence of the radiophotographs will be defined according to the size of the detector, the rotation step being for example 9° for a detector about 24 cm in size, which will enable 40 images to be obtained, the quality of which will be excellent but which cover only a reduced zone.

The dimensions of this cylinder may be sufficient in order to enable examination of a part of the human body.

By moving the subject on the rotating plate 31, several parts of the body can be scanned with the desired definitions.

The calculation of an elementary scanning of size 46×46 cm, which requires a knowledge of two vectors obtained respectively from each beam, can be carried out sufficiently quickly in order to obtain a high definition synthesis image in real time or in a few seconds.

The operation involving the implementation of a scanning is carried out in the following sequence:

acquisition of information for a zone 46 cm high with for example 20 double scans obtained by angular rotation, each step being 18°;

recording all the bitmaps on a hard disk;

preliminary inspection by the radiologist with a definition of 400 microns, i.e. a little less than 1200 sections taken in about a minute and a half;

additional inspection by a specialist with a higher definition for all or part of the examined region.

In the practical case where the definition is 50 microns over all the sections, which is the case when looking for metastases for example, the calculations could take a relatively long time. The calculation times could be reduced by a factor of 10 to 100 if an expensive multiprocessor system were used, in particular in the programming plan. Such a system could be installed after initial trials and depending on the results that are obtained.

A dynamic picture of the interior of an organism may thus be obtained by detecting the movements, and deducing therefrom additional information, for example about respiration, or cardiac movements.

The same apparatus can of course be used to observe objects, in order to permit:

a non-destructive examination of any object;

and even to obtain a series of images when it is desired to observe movements inside closed objects;

a physical object may in fact be caused to rotate rapidly, for example at a rate of 10 or 25 rotations per second;

by using a detector 6 cm in size, 40 images can be produced by combinable rotations so as to create a perfect synthesis image, and with 25 rotations per second a dynamic image can be obtained that is equivalent to that produced on a TV screen.

An example will now be described in connection with panoramic images of the face taken so as to map the whole dentition and check its geometry.

Figure 33:
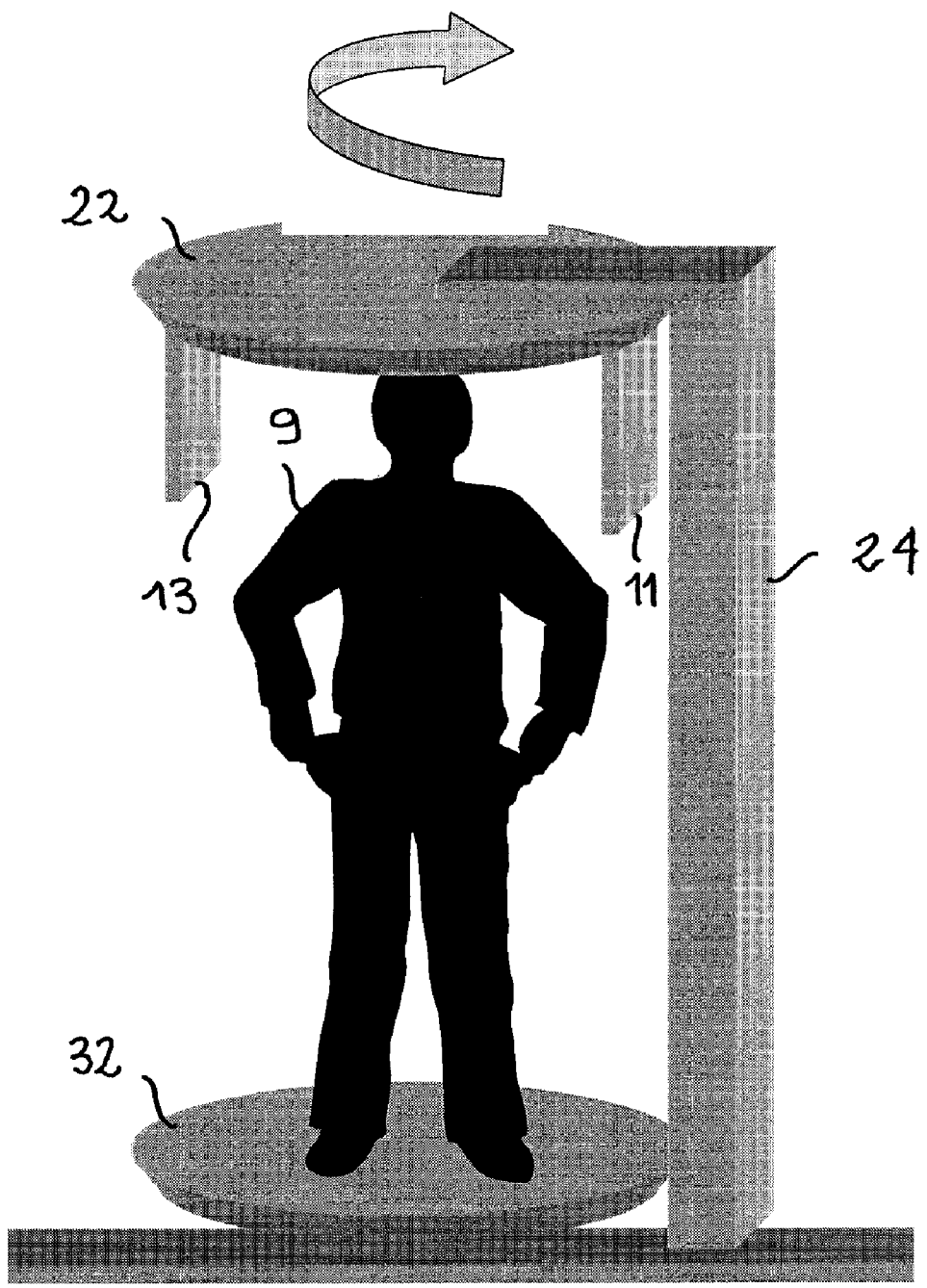
FIGS. 33 and 34 show diagrammatically a fourth apparatus according to the invention.
Figure 34:
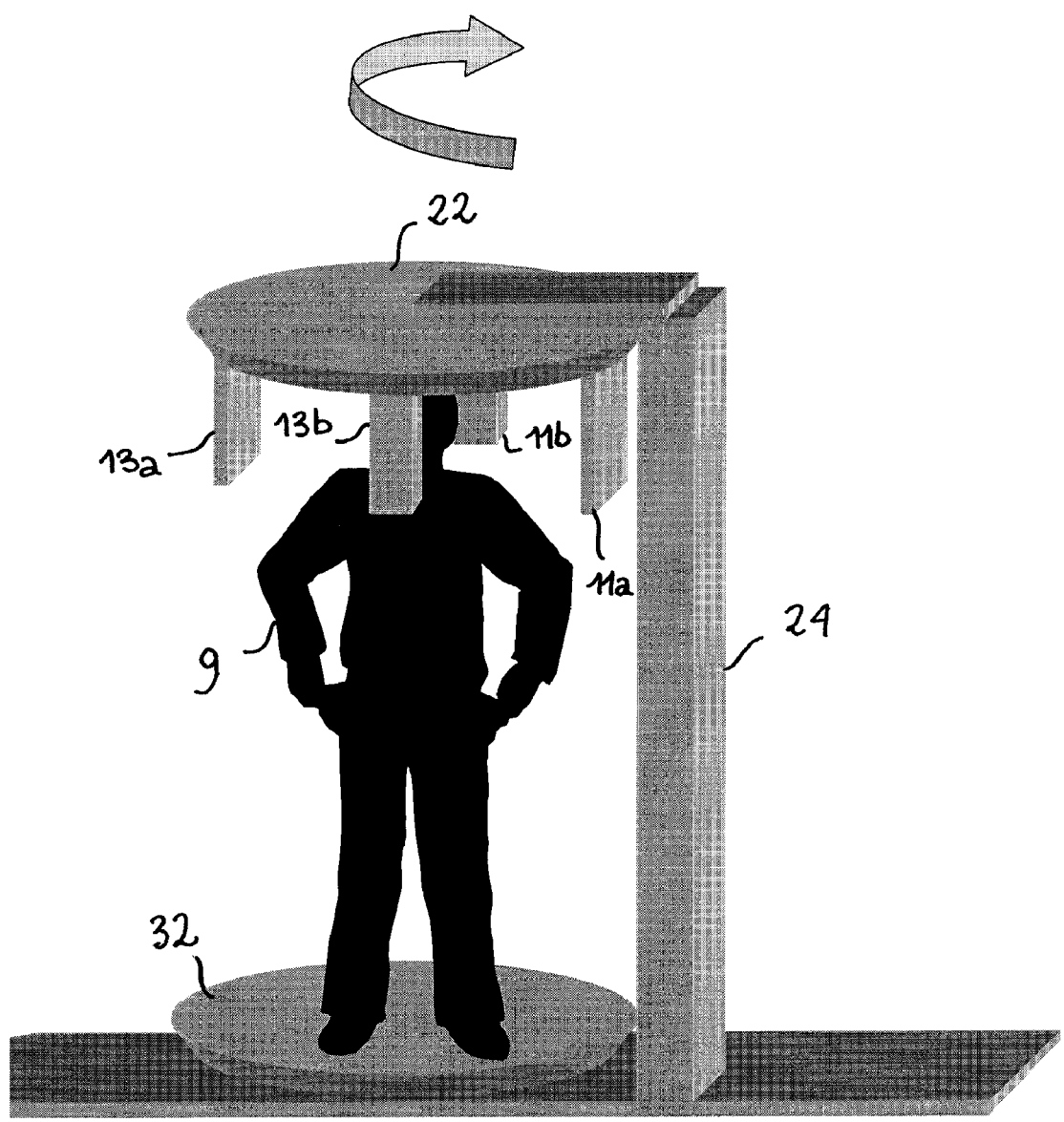

The invention in this case provides three-dimensional views and a section-by-section analysis of the jaws and possibly of the skull. FIGS. 33 and 34 show an apparatus comprising:

a rotatable or non-rotatable platform 32, extending in a horizontal plane and on which the patient stands upright;

a vertical support 24 enabling an arrangement to be supported comprising a console 22 that can rotate horizontally about a vertical axis of rotation, carrying a detector 13 about 25 cm high and 6 cm wide, and an X-ray beam device 11 enabling the image of a portion of the patient to be projected onto a detector.

The arrangement operates as follows: the upper console 22 is turned by an angle to position 0, the X-ray beam is emitted for about ½ second so as to obtain, by means of a data acquisition system, an image which will be for example of size 6×25 cm, the detector-beam arrangement is turned once more by an angle of for example 10°, a new image is taken, which is recorded in turn, and so on.

The diameter of the console is about 70 cm and the distance between the beam and the detector is of the order of 68 cm, so that the images that are obtained are contiguous.

If a double detection is employed, FIG. 34, with two orthogonal beams 11a, 11b irradiating the two detectors 13a, 13b and enabling 90° images to be obtained, while maintaining the same dimensions, 36 synchronous images and 72 asynchronous images are obtained. The quality of the information is such that the whole of the skull can easily be reconstructed in three dimensions.

Furthermore, by choosing a colour gradation or by using several different colour gradations high quality images may be obtained in which the hard tissues and parts, such as bones and teeth, will be shown in their natural white-cream colour and the highly irrigated parts such as the tongue, palate, will be shown in red, while parts such as the brain will be shown in grey.

To provide protection against X-rays, the apparatus may also be placed in a lead cabin of small dimensions, with a lead-containing glass door.

Figure 35:
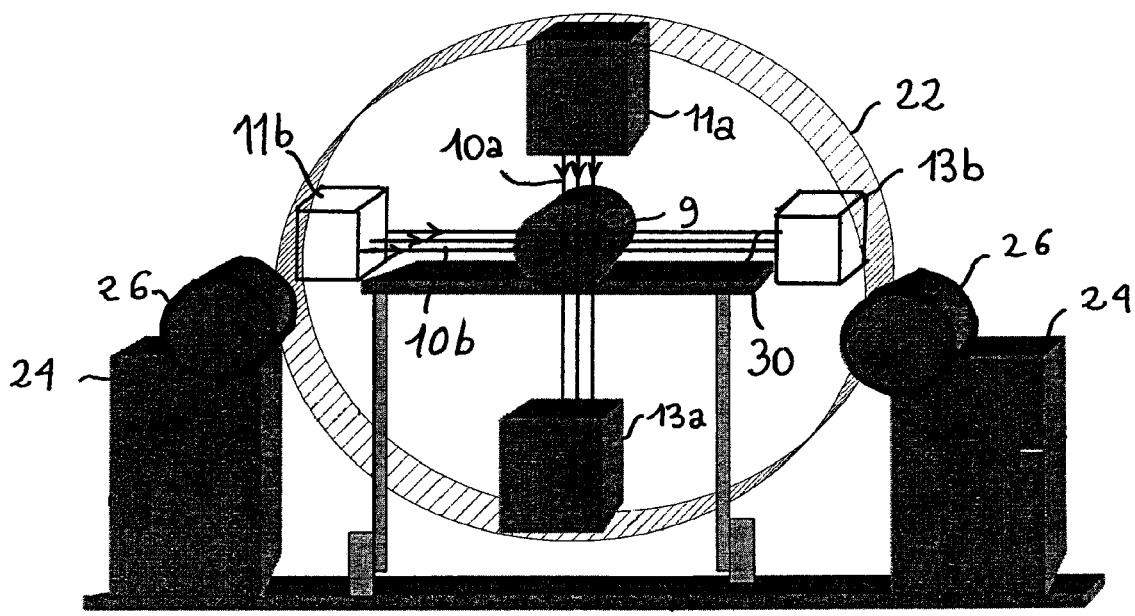
FIG. 35 shows a fifth apparatus according to the invention.

FIG. 35 shows another embodiment of the apparatus according to the invention, comprising:

a support 30 for receiving a body 9 to be examined;

a source 11a, 11b emitting a beam of X-rays or light rays in a propagation direction so as to irradiate or illuminate the body 9 to be examined;

a detector 13a, 13b irradiated or illuminated by the beam so as to detect an intensity attenuated according to the passage of the X-rays or light rays through the body 9 to be examined;

the support 30 on the one hand and the source and the detector on the other hand being movable with respect to one another about a horizontal axis of rotation 19, the source 11 and the detector 13 being split into two sources 11a, 11b and into two detectors 13a, 13b so as to form two X-ray beams or light beams preferably propagating in two orthogonal directions 10a, 10b so as to irradiate or illuminate respectively the two detectors 13a, 13b.

However, even for staff the dynamic nature of taking images can be improved by using several pairs of investigators working synchronously as couples, so as to obtain a sufficient number of synthesis images in one complete rotation lasting 1 or 2 seconds.

Such more complex apparatus arrangements will primarily be used in research.

The X-ray beams may be replaced by a light beam, for example an infrared beam with high penetrating power.

In order to check the functioning of the described apparatus, a routine has been added to the basic software. This routine enables the standard deviation relating to a point to be calculated point-by-point, and by dividing this standard deviation by the reference value the level of error relating to this point can be obtained, following which the mean of these levels of error can be obtained and thus also the accuracy of the image overall or with respect to particular regions.

Figure 36:
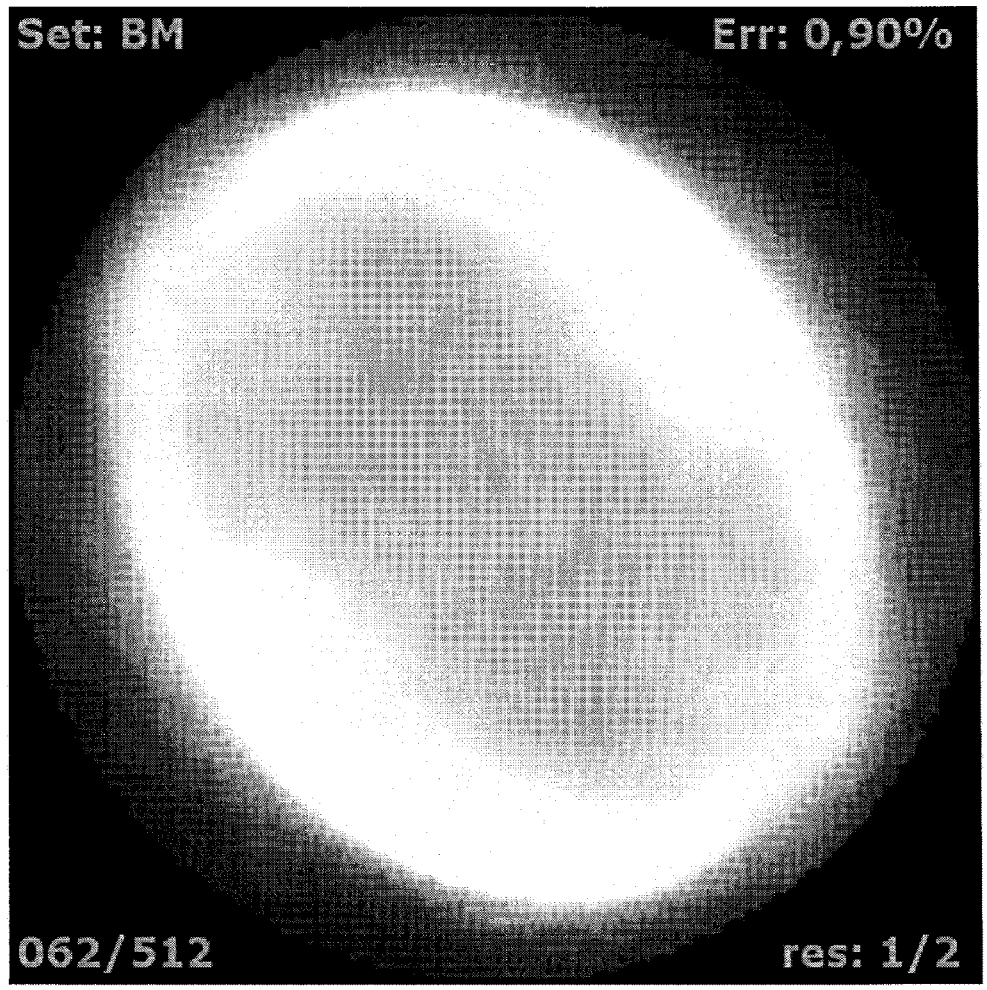
FIGS. 36 and 37 illustrate the accuracy of the calculations and images obtained, point by point.

FIG. 36 shows a tomodensitometric section corresponding to the 62-th sectional plane with respect to the fixation plane of the axis of rotation.

Figure 37:
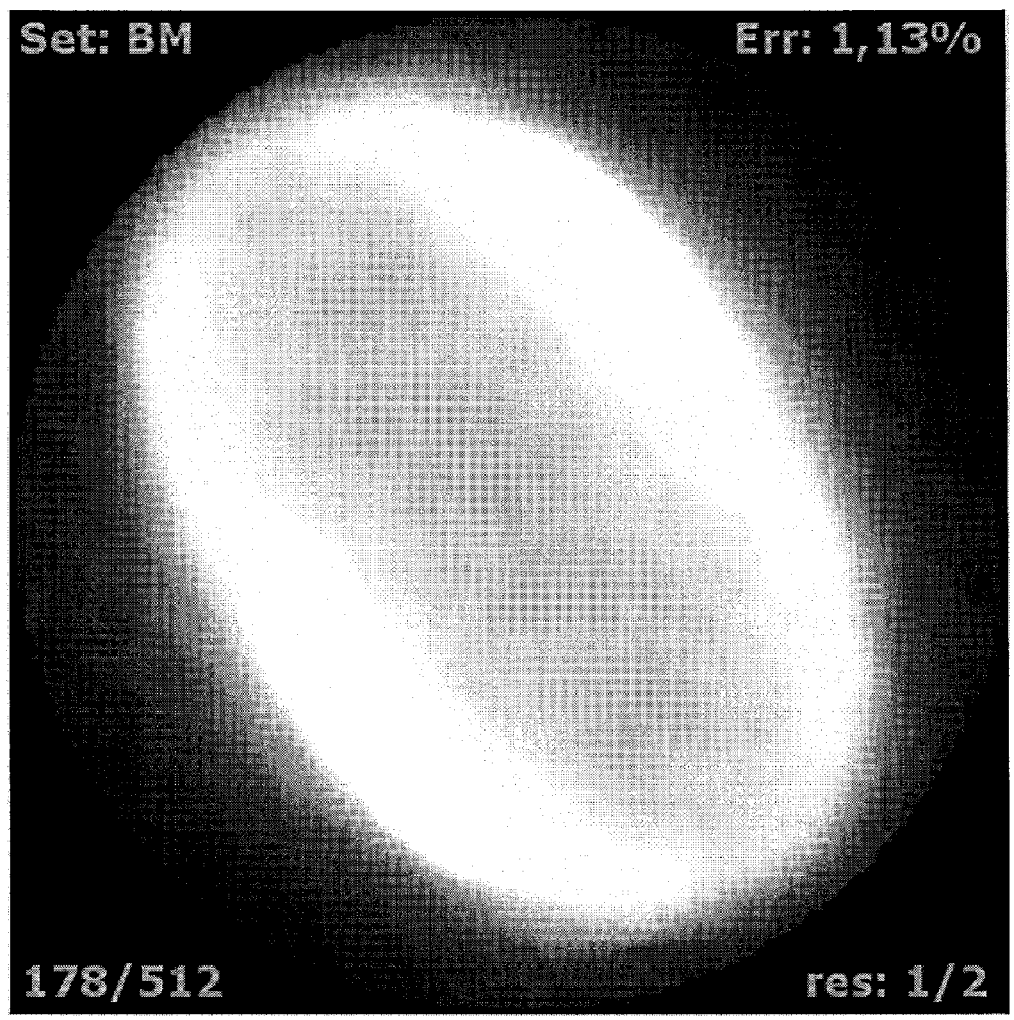
Figure 38:
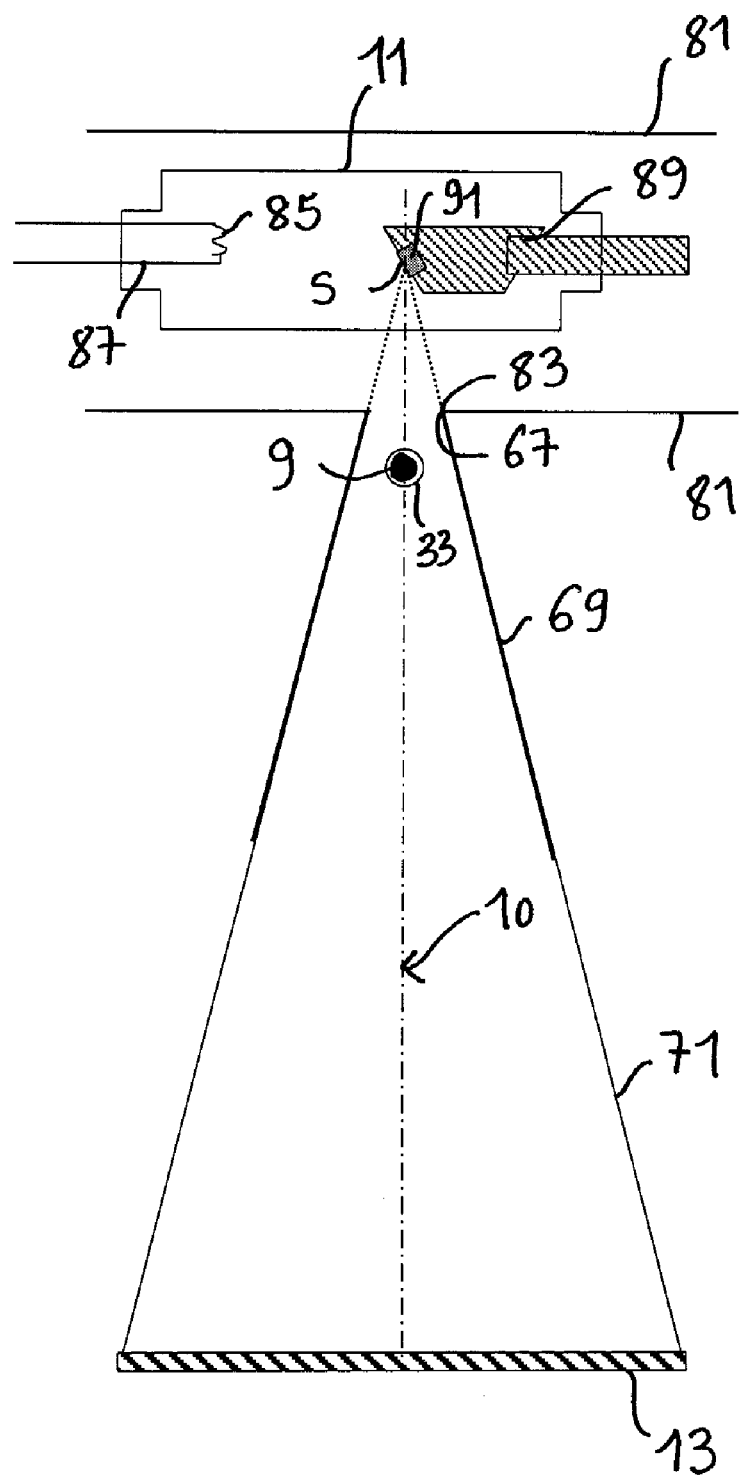
FIG. 38 shows diagrammatically a sixth embodiment of the invention, with a means for projecting the beam from the X-ray source so as to form a conical beam.

FIG. 37 shows a tomodensitometric section corresponding to the 178-th plane. The quality of the images may be evaluated: the mean error for the whole image is 1.90% for FIG. 36 and 1.13% for FIG. 37.

A sixth embodiment of the invention is described with reference to FIGS. 38 to 43. In order to obtain very high definition images, one may either use a detector having a very high definition, or perform a geometrical enlargement on the basis of the following principle:

a conical beam 71 or pyramidal beam 73 centred on the axial direction 10 passes through the object 9 to be examined;

this beam terminates at a detector 13, the definition of which is for example 25 microns.

However, at present there are no detectors available on the market whose definition is better than 25 microns.

In order to obtain a definition of 0.1 micron, the apparatus according to the invention comprises (see FIG. 38) a detector 13 of size 230 mm and having a definition of 25 microns, manufactured by ATMEL, and an X-ray source 11 manufactured by KODAK TROPHY, operating at 70,000 Volts, which produces a wavelength of the order of 0.02 nanometres.

A small body 9 to be examined, for example of millimeter or microscopic size, is introduced into an optical tube 33, the internal diameter of which is of the order of 100 microns; this optical tube 33 is caused to rotate about the axis of rotation 19 by a stepping micromotor, with steps that may be of 1°, 5°, 10°, 18°, in order to obtain 360, 72, 36, 20 angular positions.

Figure 40:
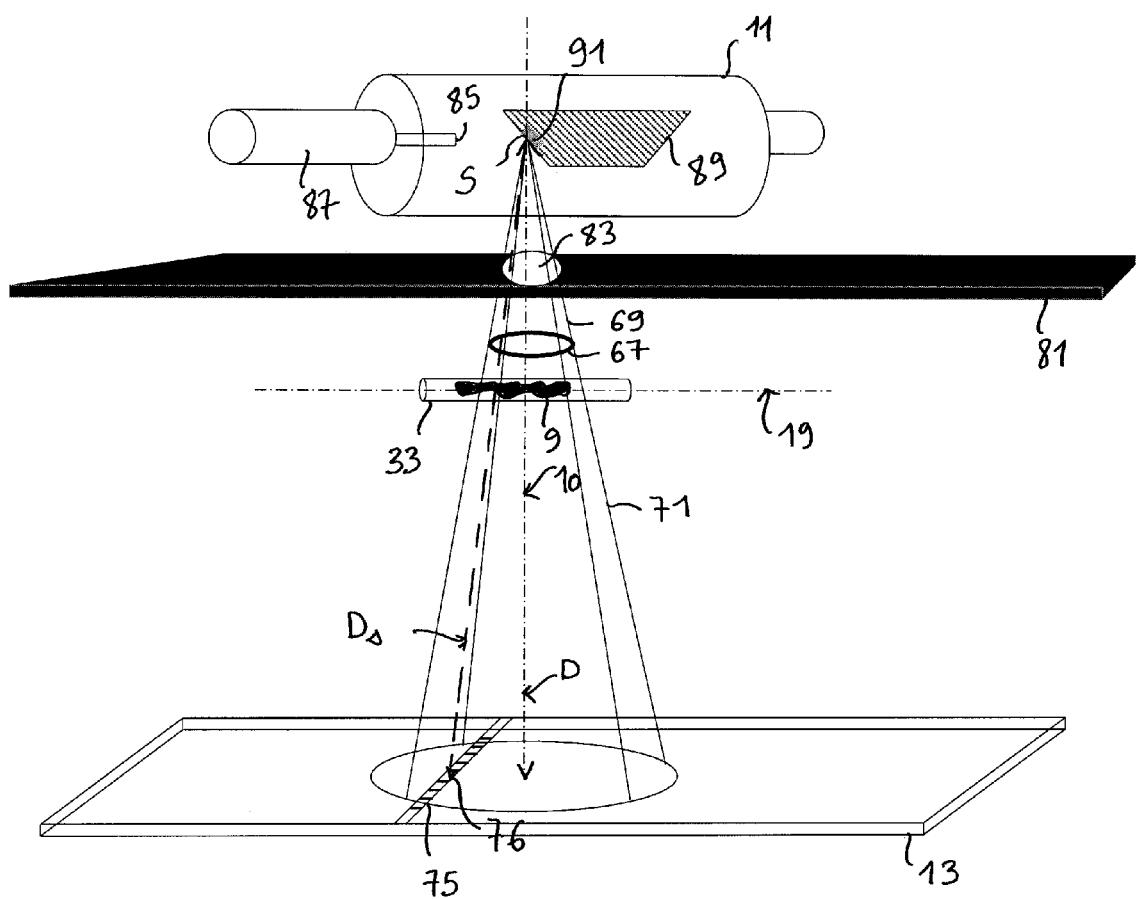
FIG. 40 is a perspective diagrammatic view of the sixth embodiment of the invention for a conical beam.
Figure 41:
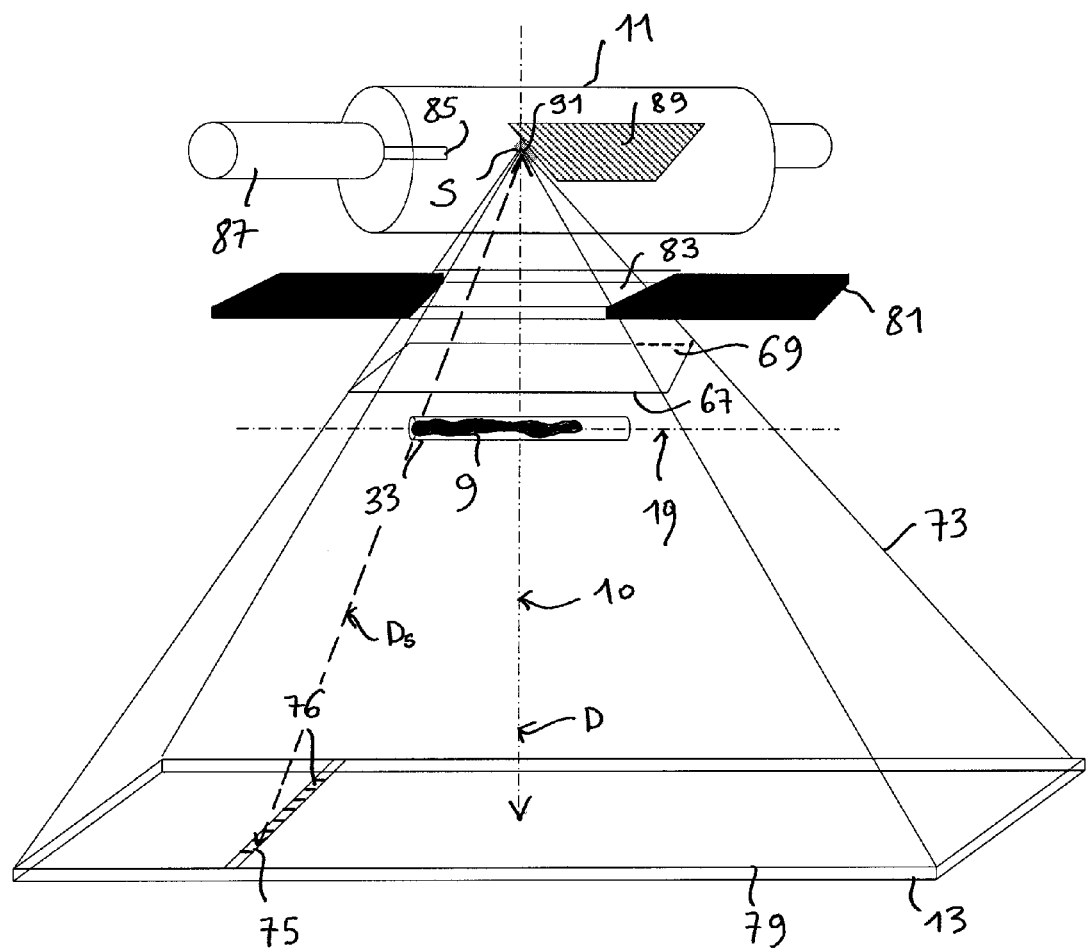
FIG. 41 is a perspective diagrammatic view of the sixth embodiment of the invention for a pyramidal beam.

The X-ray tube 11 is arranged in a casing 81. A means 69 for projecting the source 11 in the form of a conical beam 71 or pyramidal beam 73 is fixed to the casing 81. FIGS. 40 and 41 show respectively examples of conical and pyramidal projection. In FIG. 40 the projection means 69 is a truncated cone. In FIG. 41 the projection means 69 is a truncated pyramid. The casing 81, which is impermeable to X-rays, is provided with an opening 83 opposite the projection means 69. The intersection between the conical beam 71 or pyramidal beam 73 and the detector 13 describes a circle 77, an ellipse or a polygon 79.

The X-ray tube itself is made of glass or a material transparent to X-rays and contains a filament 85 connected to a cathode 87, and a solid anode 89 arranged opposite the filament. This anode is made of a material having a good thermal conductivity, for example copper. A tungsten target (focus) 91 of size of the order of 1 mm is inserted into the anode. When the beam of electrons strikes the target 91 these electrons are decelerated and part of their kinetic energy is converted into X-rays, the wavelength of which depends on the electron-volt value of the electron beam. By way of example, for a tube operating at 160,000 volts, the wavelength is equal to 0.00774 nanometres. The definition that may be obtained, i.e. the half wavelength, is far better than 0.1 micron.

The detector 13 is arranged so that at the level of the object 9 to be examined the truncated cone or truncated pyramid has a size of the order of 100 to 1000 microns, and the detector has a size of 230 mm. The geometrical enlargement then varies between 2300 and 230.

Under these conditions definitions varying between 0.1 and 1 micron may be obtained. Of course, simple adjustments enable the distance between the source and the detector to be altered so as to obtain an adequate geometrical enlargement. The coefficient of geometrical enlargement of the body to be examined is equal to the ratio between, on the one hand, the distance between the vertex of the conical or pyramidal beam and the detector and, on the other hand, the distance between the vertex of the conical or pyramidal beam and the object to be examined.

The emission of X-rays is omnidirectional, though the beam 71 emitted by the tube 11 is of conical shape if the projection means 69 has a truncated conical shape and is provided with an opening 67 having a circular base. In this case the cone has as vertex S the target 91, and as aperture angle the angle permitted by the opening 67 of the projection means, which is equal to the opening 83 of the casing 81. The projection means may be constituted by the opening 83 of the casing 81 itself.

Figure 39:
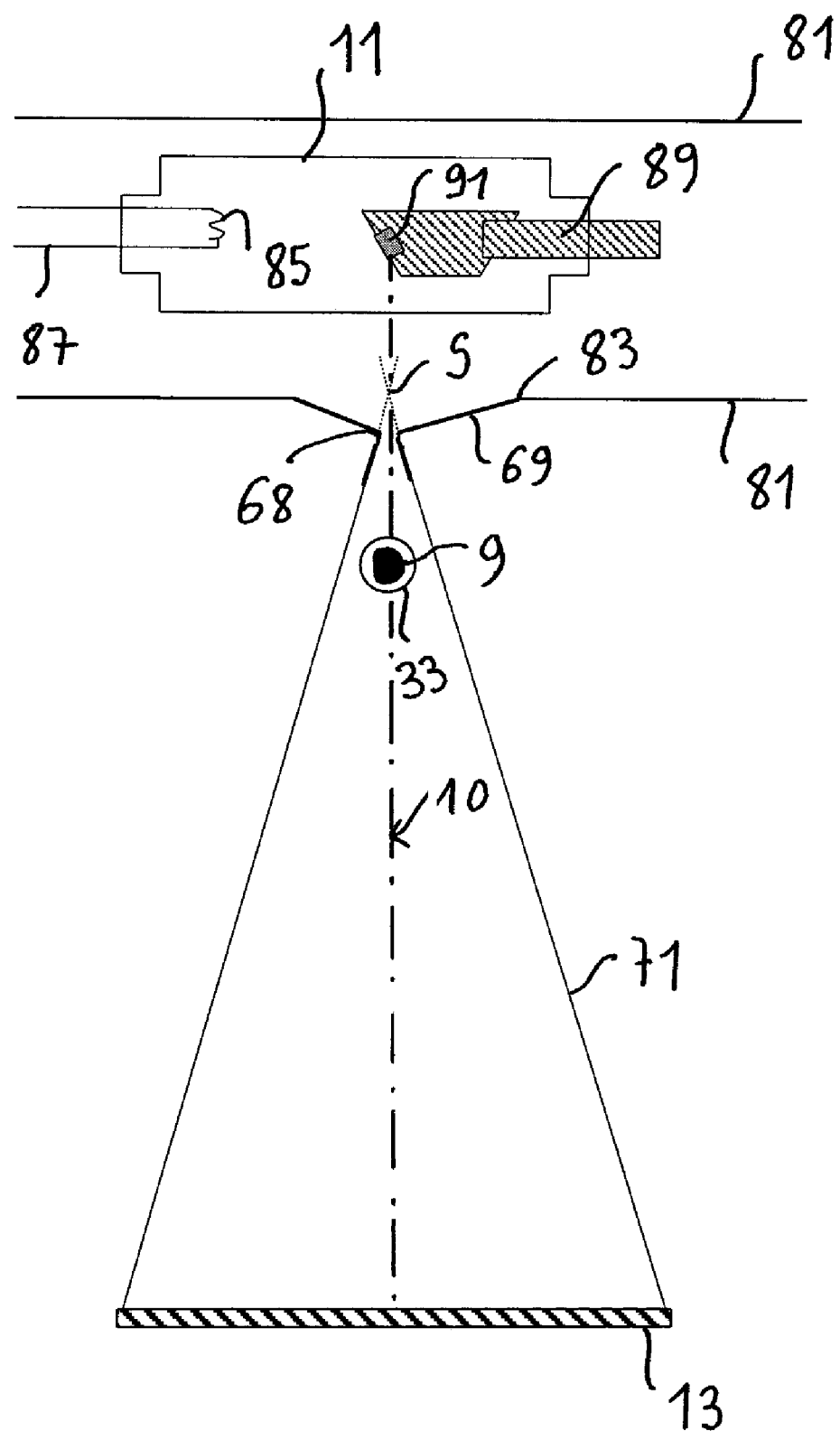
FIG. 39 shows the sixth embodiment of the invention with a projection means comprising a constriction.

When the vertex S of the cone coincides with the target 91, the coefficient of enlargement is limited by the distance between the opening 67 of the projection means 69 and the detector 13. By forming a constriction 68, the vertex S of the cone is situated outside the tube 11, as illustrated in FIGS. 39 and 42.

In order to control the X-ray source so as to emit one or more pulses, a rotating anode controlled by a motor M is advantageously provided.

Figure 42:
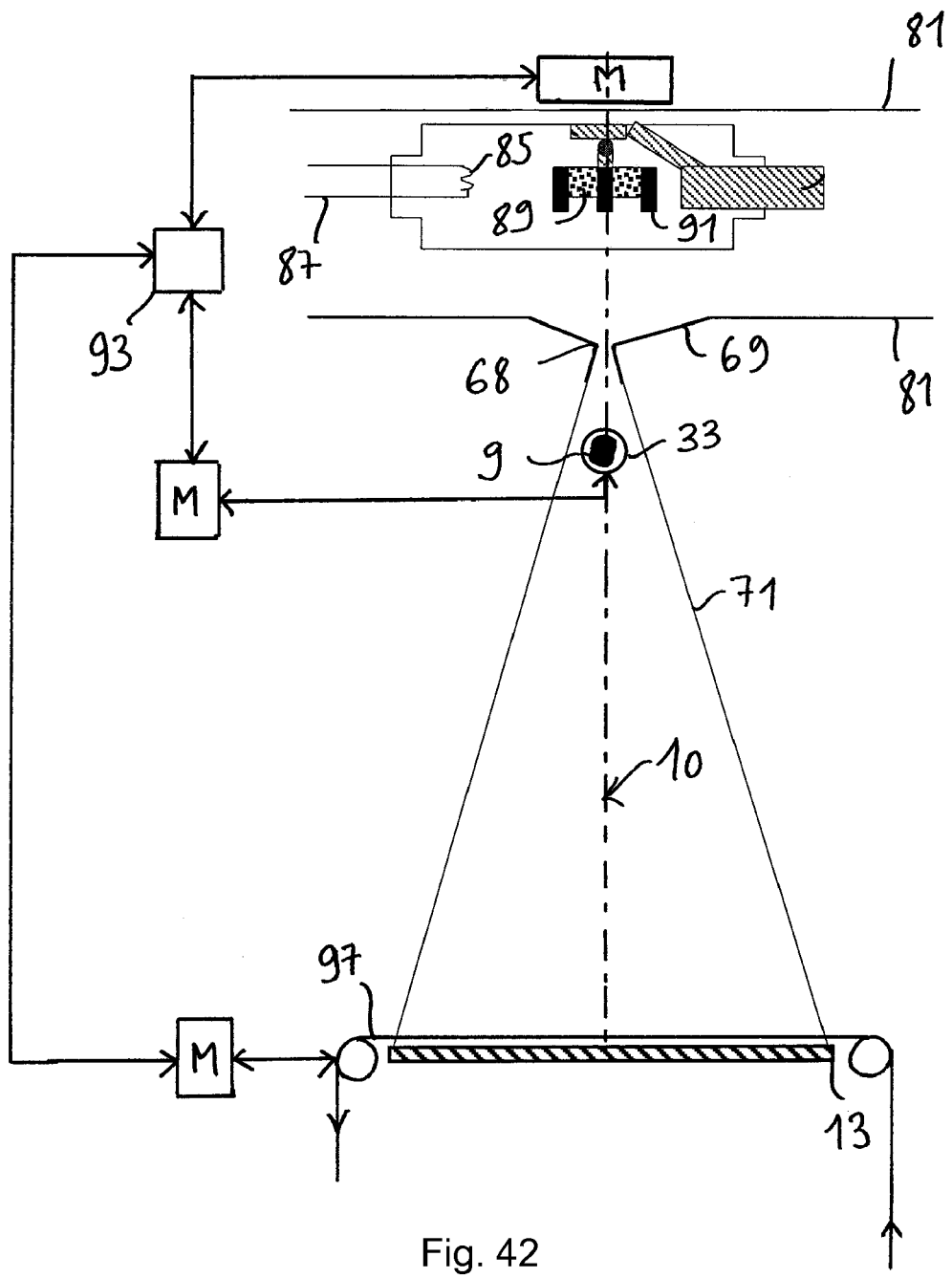
FIG. 42 shows diagrammatically the sixth embodiment of the invention with a source comprising a rotating anode.

The anode 89 shown in FIG. 42 may be used, which carries a plurality of targets 91 and rotates rapidly so as to produce a succession of flashes, the duration of which depends on the width of the target and the diameter of the anode. Thirty-six targets of 1 mm width may for example be arranged on an anode of diameter 11.4 cm, i.e. about 360 mm in circumference, each target occupying an arc of the order of 1 mm, i.e. about 1°. A complete revolution thus produces 36 flashes, which are advantageously synchronised by a synchronisation means 93 for synchronising the motors M of the support 33 and of the rotating anode 89 with the rotation of the support 33 of the object 9 so as to obtain 36 images staggered angularly by 10°. Thus, each pulse emitted by the source irradiates or illuminates the detector 13 between each rotation of the support 33.

The above scenario assumes a very high recording rate of the flashes. If this rate is from 10 to 50 rotations per second, 10 to 50 images are obtained in one second, each image resulting from the aggregation of the 36 elementary images. Of course, the calculation time is much greater than the acquisition time, but once the calculation has been made an actual film containing 50 images per second of the object to be examined may be obtained.

The rotation of the anode may be effected in several well-known ways, for example by means of a motor M fixed to the anode and controlled by a low voltage electric current, or by a rotating magnetic field acting inside the tube 11 on a rotor secured to the anode 89.

In order to operate dynamically with the aforedescribed rotating anode, if the detector 13 does not have a sufficiently rapid response, a silver oxide film 97 with fine grains having a fast reaction rate may be employed.

Such a film 97 is run with the regular emission of beams due to the rotation of the anode 89 carrying a plurality of targets 91, the film being moved in an irregular, stop-start manner by a displacement means M synchronised 93 with the rotation of the rotating anode 89, so that each pulse of the source 11 irradiates or illuminates the film 97 between each stop-start movement, thereby obtaining for example 500 shots per second. With a rotation of the optical tube 33 in steps of 18° and the movement of the film at the appropriate rate, a film is obtained containing 25 images per second, which means that a considerable number of images has to be processed, requiring the use of supercomputers. In order to convert the detected intensities, an analogue-digital converter 15 is used comprising a camera for reading the photographic film.

Figure 43:
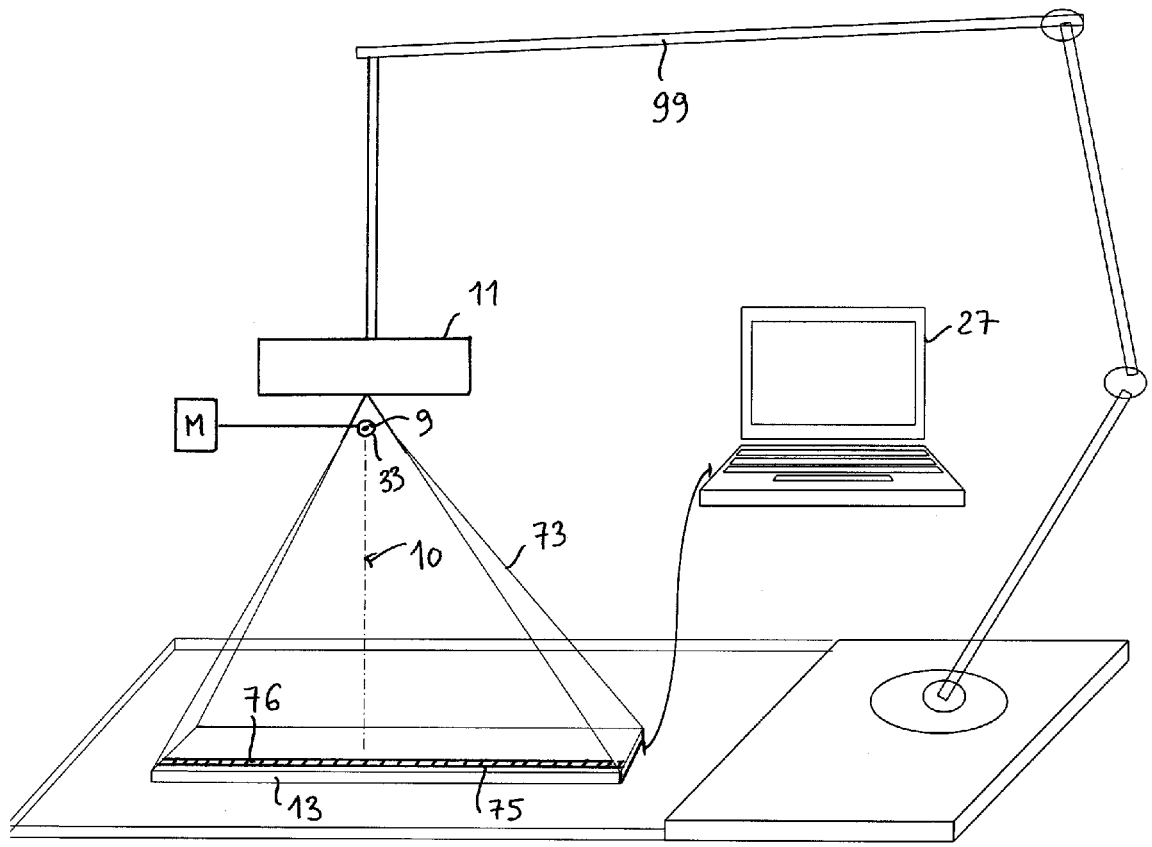
FIG. 43 shows an overall view of the sixth embodiment of the invention.

The apparatus comprises, FIG. 43:
in the upper part, the X-ray source 11, which can easily be moved by means of an articulated arm 99;
the projection means consisting of a truncated pyramid 69, projecting the source in the form of a pyramidal beam 73 with base dimensions 230 mm×60 mm, and in which the vertex is an opening of size of the order of 1 mm; the optical tube 33 serving to support the body 9 to be examined, of diameter about 1 mm; and
a stepping motor M controlling the rotation of the optical tube 33.

The functioning of this arrangement is as follows:
for a first angular position of the optical tube 33 about the axis of rotation 19, the source 11 is activated so as to excite the detector 13 for a time that may vary between 1 millisecond and 100 milliseconds, this first image being obtained in the form of a bitmap in the computer 27.

The operation is repeated 35 times, producing a rotation of the optical tube 33 of 10° between each operation. Thirty-six images are thus obtained, which are processed so as to obtain tomodensitometric sections in any arbitrary sectional plane of the irradiated area, perpendicular to the axis of rotation 19. If the process is repeated, time-staggered images are obtained, permitting a dynamic view of the examined body. Moreover, it is possible to obtain tomodensitometric sections in the area of the body to be examined along the axis of rotation 19 of the optical tube 33, enabling three-dimensional images to be generated.

The processing of the data obtained from the detected intensities is the same as that described hereinbefore. It is sufficient to recall that the following stages are carried out using the suitably programmed computer 27:
averaging the data obtained from the conversion of the detected intensities in a band 75 of the detector 13 for a first angle of rotation about the axis of rotation 19, to obtain n mean values within n elementary segments 76 of the band, and averaging the data obtained from the conversion of the detected intensities in the band 75 of the detector 13 for a second angle of rotation, preferably differing by 90 degrees from the first angle of rotation, to obtain m mean values within m elementary segments 76 of the band. The n and m elementary segments correspond to a grid of n×m elementary zones of a sectional plane of the object 9 perpendicular to the axis of rotation 19. The n and m mean values that are obtained are respectively the terms of a column generating vector and a line generating vector;

construction of an initial matrix (n,m) with the terms of the two generating vectors, by assigning to each elementary zone a line term and a column term (Bij) representing a coefficient of attenuation and defined by the half sum of the homologous term (i) of the column generating vector divided by the number (m) of terms of the line generating vector, and of the homologous term (j) of the line generating vector divided by the number (n) of terms of the line generating vector;

adjusting the coefficient of attenuation in each elementary zone by a method of least squares, taking account of the line boundary values defined by the sum of the terms (Bij) on each of the lines of the initial matrix, and the column boundary values defined by the sum of the terms (Bij) on each of the columns of the initial matrix, and also the terms of the generating vectors as line or column constraints, and by using the formula mentioned hereinbefore so as to obtain an adjusted matrix in which the line and column boundary values calculated with the aid of the adjusted values (Cij) are equal, for each line and for each column, respectively to the terms of the line and column generating vectors.

These stages are repeated for data obtained with different pairs of angles of rotation. The adjusted matrices obtained for the different pairs of angles are then processed by a rotation operator so as to superimpose all the pairs of angles on the same pair of angles (0°-90°), and the adjusted matrices are averaged term by term and superimposed so as to obtain a synthesis matrix representing an image of the coefficients of attenuation of the examined body 9 under the definition determined by the grid.

However, in the case where the beam is not cylindrical, the detected intensities obtained by the detector are a function not only of the coefficients of absorption along an X-ray beam, but also of the length of the X-ray itself. In order to process the image in the same way as in the case of a cylindrical beam, it is necessary to correct the data corresponding to a virtual cylindricalisation of the conical or pyramidal beam, taking into account:

on the one hand the distance D between the geometric vertex S of the conical beam 71 or pyramidal beam 73 and the detector 13 in the axial direction 10 of the beam; and on the other hand, the distance Ds between the geometrical vertex S and an elementary segment 76 of the band 75 of the irradiated or illuminated area of the detector 13.

This correction corresponds to a virtual enlargement of the object 9 to be examined, along the axis of rotation 19, and may be illustrated by the following table:

| I | II | III | IV | V |
|---|---|---|---|---|
| 1 | 44.4112598 | 1.0002536 | 1.00050726 | 1.00076099 |
| 2 | 44.4450222 | 1.00101401 | 1.00202906 | 1.00304513 |

-continued

| I | II | III | IV | V |
|---|---|---|---|---|
| 3 | 44.5012359 | 1.00228009 | 1.00456538 | 1.00685587 |
| 4 | 44.5798161 | 1.00404991 | 1.00811622 | 1.01219901 |
| 5 | 44.6806446 | 1.00632082 | 1.0126816 | 1.01908258 |
| 6 | 44.8035713 | 1.00908944 | 1.0182615 | 1.02751694 |
| 7 | 44.9484149 | 1.01235169 | 1.02485594 | 1.03751464 |
| 8 | 45.1149643 | 1.0161028 | 1.0324649 | 1.04909047 |
| 9 | 45.30298 | 1.02033739 | 1.04108839 | 1.0622614 |
| 10 | 45.5121962 | 1.02504946 | 1.0507264 | 1.07704653 |
| 11 | 45.7423218 | 1.03023247 | 1.06137895 | 1.09346706 |

In this table, the distance in cm of an elementary segment 76 at the point of intersection of the axial direction 10 of the beam with the detector 13 is recorded in column I. The distance Ds between the geometrical vertex S and the elementary segment 76 is calculated in column II, assuming that the distance D between the geometrical vertex S and the detector along the axial direction 10 is equal to 44.4 cm. The following three corrections are calculated:

the linear correction, column III, which is directly proportional to the ratio between the value of the distance Ds and 44.4 cm;

the squared correction, column IV, which is the square of the linear correction; and the cubed correction, column V, which is the cube of the linear correction.

A systematic correction, which in the general case will be equal to the squared correction, may thus be applied to the intensities detected by the detector. An empirical correction may also be applied, which is obtained by means of a scaling carried out on the measurements at all points of the detector, of an image or of a standard grid. Finally, a polynomial adjustment of order 3, or if necessary of higher order, may be carried out, which will be incorporated directly into the process for evaluating the correction.

Following this correction, corrected values are obtained that are very close to those that would have been detected in the case of a cylindrical beam.

Also, the computer 27 carries out a supplementary step in this case, consisting in correcting the data by multiplying them by a correction factor depending on the one hand on the distance D between the geometrical vertex S of the conical beam 71 or pyramidal beam 73 and the detector 13 in the axial direction 10 of the beam and, on the other hand, on the distance Ds between the geometrical vertex S and an elementary segment of the band 75 of the irradiated or illuminated area of the detector 13. This correction corresponds to a virtual enlargement of the object to be examined along the axis of rotation 19.

In reality the whole procedure takes place as if, due to the distance correction, an enlarged image were produced by cylindrical projection with a greatly improved definition.

The apparatus that has just been described may be provided with two sources 11a,11b and two detectors 13a,13b in a similar way to that described hereinbefore for the cabin-type apparatus. In this case each source 11a,11b is provided with a projection means 69.

Since the orthogonal beams function in a synchronous manner, for 20 elementary shots one can obtain 20 synchronised images, which are particularly useful when it is desired to obtain dynamic views.

Micro-organisms, the size of which is for example of the order of 2 to 3 microns, are placed in the optical tube 33. These micro-organisms will be able to be viewed in three dimensions if shots are taken over an area along the axis of rotation 19 of the optical tube, the irradiated or illuminated area depending on the aperture 67 of the projection means 69.

The so-called "cellular" scanner that has just been described should help in obtaining more detailed information of the internal geometry and structure of cells, humans or animals, and should also facilitate the examination of small objects, in particular those produced in the horological or microelectronics industries. In fact, with a screen of size 75 cm×48 cm, and assuming that an image of about 100×65 microns is projected, we obtain a magnification of 7500. By zooming by a factor of just 10, we can easily obtain an internal view of cells 10 microns in size, and obtain much better results for small cells or parts of cells.

The calculation rates that have been achieved enable one to envisage the following figures:

generation of an image with a definition of 0.1 micron for a field of 100 microns, i.e. one million points, in 0.2 second with a processor used for top of the range PCs;

generation of 1000 images with a multiprocessor system currently available on the market, using only ten combined processors, in 20 seconds.

The invention claimed is:

1. Method for the X-ray or infrared imaging of a body, in which a body to be examined is received by a support, the method comprising the steps of:
   a)—irradiating the body to be examined or illuminated by means of a source emitting a beam of X-rays or light rays in a propagation direction,
   b)—detecting an intensity that is attenuated according to the passage of the X-rays or light rays through the body to be examined means of a detector irradiated or illuminated by the beam,
   c)—converting the detected intensities into data enabling an attenuation of the X-rays or light rays by the body to be examined, to be determined with the aid of an analogue/digital converter,
   d)—turning the mobile mounted support by an angle of rotation about an axis of rotation with respect to the source and to the detector mounted on a stand, or turning the source and the detector mounted on a mobile stand by an angle of rotation about an axis of rotation with respect to the support, and
   e)—carrying out the following stages with the aid of a computer:
   (1) averaging the data obtained from the conversion of the detected intensities in a band of the detector for a first angle of rotation, to obtain n mean values ($c_i$) in n elementary segments of the band, and averaging the data obtained from the conversion of the detected intensities in the band of the detector for a second angle of rotation, preferably differing by 90° from the first angle of rotation, to obtain m mean values ($\rho_j$) in m elementary segments of the band, wherein the n and m elementary segments produce a grid of n×m elementary zones of a sectional plane of the object to be examined perpendicular to the axis of rotation and wherein the n and m mean values respectively are the ($c_i$) terms of a column generating vector and the ($\rho_j$) terms of a line generating vector,
   (2) building an initial matrix (n,m) with the terms of the generating vectors, by assigning to each elementary zone a line term and a column term ($B_{ij}$) representing a coefficient of attenuation defined by the half sum of the homologue term ($c_i$) of the column generating vector, divided by the number (m) of terms of the line generating vector, and of the homologous term ($\rho_j$) of the line generating vector, divided by the number (n) of terms of the column generating vector, $$B_{ij} = \frac{1}{2}\left(\frac{\rho_j}{n} + \frac{c_i}{m}\right)$$

(3) adjusting the coefficient of attenuation in each elementary zone using the following formula:

$$C_{ij} = \frac{\rho_j}{n} + \frac{c_i}{m} - \frac{1}{2nm}\left(\sum_{i=1}^{n} c_i + \sum_{j=1}^{m} \rho_j\right)$$

where,
$C_{ij}$ is the sought value of the coefficient of attenuation of the elementary zone (i,j) of the grid,
(n) is the number of lines of the initial matrix,
(m) is the number of columns of the initial matrix,
$\rho_j$ is the j-th term of the line generating vector calculated at stage (1), and
$c_i$ is the i-th term of the column generating vector calculated at stage (1),
to arrive at an image of the sectional plane of the body examined under the first and the second angles of rotation, corresponding to an adjusted matrix, for which the line and column boundary values calculated with the adjusted values ($C_{ij}$) are equal, respectively, for each line and column, to the terms of the line and column generating vectors, $$\sum_{j=1}^{m} C_{ij} = c_i \quad \sum_{i=1}^{n} C_{ij} = \rho_j$$

(4) repeating the stages (1) to (3) for data acquired with different pairs of angles of rotation to respectively arrive at different adjusted matrices corresponding to different images of the sectional plane of the body examined under the different pairs of angles of rotation,
(5) by means of a rotation operator, superimposing on a same pair of angles (0°-90°) all the properly adjusted matrices obtained for the different pairs of angles, and
(6) displaying on the computer a synthesis image of the sectional plane of the examined body, corresponding to a synthesis matrix of the coefficients of attenuation obtained, for each elementary zone (i,j) of the grid, a term-by-term averaging of all the adjusted matrices obtained at stage (4) and superimposed at stage (5).

2. X-ray or infrared imaging method according to claim 1, wherein the stage (1) is carried out for four pairs of angles of rotation, preferably mutually orthogonal (0°-90°; 90°-180°; 180°-270°; 270°-360°) so as to form four column generating vectors each having as co-ordinates the n mean values obtained for the first angle of rotation (0°; 90°; 180°; 270°) and four line generating vectors each having as co-ordinates the m mean values obtained for the second angle of rotation (90°; 180°; 270°; 360°) of each of the four pairs of angles,
wherein the four column generating vectors and the four line generating vectors are treated by a rotation operator so as to superimpose them on the same pair of angles of rotation (0°-90°), following which a reduced column generating vector and a reduced line generating vector are formed by term-by-term averaging of the homologous co-ordinates of the column vectors and line generating vectors superimposed on the same pair of angles of rotation (0°-90°), wherein stage (2) is carried out starting from the co-ordinates of the reduced column and line generating vectors wherein stage (3) is carried out to obtain an adjusted matrix for which the line and column boundary values calculated for the adjusted values (Cij) are equal, respectively, for each line and column, to the terms of the reduced line and column generating vectors, and wherein stages (4) and (5) are carried out for different groups of four pairs of angles of rotation, shifted by a multiple of a reference angle (10°), with respect to the angles of rotation of the pairs of the first group.

3. X-ray or infrared imaging method according to claim 1, wherein a stand comprises a first source and a second source emitting a first beam of X-rays or light rays and a second beam of X-rays or light rays in a first and a second propagation direction, which are preferably orthogonal, wherein the stand further comprises a first detector irradiated or illuminated by the first beam and by a second detector irradiated or illuminated by the second beam; and wherein by means of the computer, the stage (1) is carried out by averaging the data obtained from the conversion of the intensities detected in a first band of the first detector, and by averaging the data obtained from the conversion of the intensities detected in a second band of the second detector, for the sectional plane of the object, perpendicular to the axis of rotation and in which the first and second bands extend.

4. Method according to claim 1, wherein an area of the body to be examined, parallel to the axis of rotation is irradiated or illuminated in one or more control pulses of the source, and the following supplementary stages are carried out with the aid of the computer:

(7) recording the data obtained from the conversion of the detected intensities in the whole of the irradiated or illuminated area of the detector;

(8) selecting, from among the recorded data, those that are derived from the conversion of the detected intensities in the band of the irradiated or illuminated area of the detector for the first and the second angle of rotation, or in the first and the second band respectively of the first and the second detector; and carrying out the stages (1) to (5) starting from these selected data.

5. Method according to claim 4, wherein a large or the total area of the body to be examined is irradiated or illuminated by the source so as to project a conical or pyramidal beam, and the following supplementary stages are carried out with the aid of the computer:

(9) correcting the selected data by multiplying them by a correction factor depending on the one hand on the distance between the geometrical vertex of the conical beam or pyramidal beam and the detector in the axial direction of the beam, and on the other hand on the distance between the geometrical vertex and an elementary segment of the band of the irradiated or illuminated area of the detector, this correction corresponding to a virtual enlargement of the object to be examined along the axis of rotation; and carrying out the stages (1) to (6) using the selected and corrected data.

6. Apparatus specifically designed for the implementation of a method according to claim 1, in particular in the case where the body to be examined is the body of an individual, comprising:

a support to receive a body to be examined;

a source emitting a beam of X-rays or light rays in a propagation direction so as to irradiate or illuminate the body to be examined;

a detector irradiated or illuminated by the beam so as to detect an intensity that is attenuated according to the passage of the X-rays or light rays through the body to be examined;

and in which, the support on the one hand and the source and the detector on the other hand are mobile, the support being mobile with respect to the other two about a vertical axis of rotation so that the individual is accommodated in a standing or sitting position by the support.

7. Apparatus according to claim 6, in which the support comprises a plate rotating about the vertical axis of rotation and is preferably provided with means for immobilising the individual or with an armchair that is transparent to X-rays.

8. Apparatus according to claim 6 in which the source and the detector are split into two sources and two detectors so as to form two X-ray beams or light beams preferably propagating in two orthogonal directions so as to irradiate or illuminate respectively the two detectors.

9. Apparatus according to claim 7 wherein the armchair is mounted on a telescopic leg.

10. Apparatus according to claim 6, in which the support and, where appropriate, the rotating table are arranged in a cabin that is impermeable to X-rays and the source or the detector emits or receives the X-rays through a junction module that can be moved vertically with the aid of vertical displacement means so as to be displaced with respect to a window formed in a wall of the cabin, and that can be moved horizontally with the aid of horizontal displacement means so that it can be moved through the window and into the cabin.

11. Apparatus according to claim 10, in which the source and the detector can be moved vertically with respect to the junction module with the aid of vertical displacement means controlled in a synchronous manner.

12. Apparatus according to claim 10, in which sliding panels are raised as a group in gantry supports of the cabin by lifting means so as to open an aperture forming the window through which the junction modules are moved horizontally so as to enter the cabin.

13. Apparatus according to claim 6, in which the source and the detector are mounted on a bracket so that they can be rotated about the vertical axis of rotation.

14. Apparatus specifically designed for the implementation of a method according to claim 1, comprising:

a support to receive a body to be examined;

a source emitting a beam of X-rays or light rays in a propagation direction so as to irradiate or illuminate the body to be examined;

a detector irradiated or illuminated by the beam so as to detect an intensity attenuated according to the passage of the X-rays or light rays through the body to be examined;

the support on the one hand and the source and the detector on the other hand are mobile, the support being mobile with respect to the other two about a horizontal axis of rotation;

and in which, the source and the detector are split into two sources and two detectors so as to form two X-ray beams or light beams that preferably propagate in two orthogonal directions so as to irradiate or illuminate respectively the two detectors.

15. Apparatus specifically designed for the implementation of a method according to claim 5, in particular in the case where the body to be examined is of a millimeter or microscopic size, comprising:
- a support for receiving the body to be examined;
- a source emitting a beam of X-rays or light rays in a propagation direction so as to irradiate or illuminate the body to be examined;
- a detector irradiated or illuminated by the beam so as to detect an intensity attenuated on account of the passage of the X-rays or light rays through the body to be examined;
- the support on the one hand, and the source and the detector on the other hand are mobile, the support with respect to both the source and the detector, about an axis of rotation;

and in which,
- a projection means is provided so that the source irradiates or illuminates the detector with a conical beam or pyramidal beam centred on the axial direction of the beam, and
- a ratio between, on the one hand, the distance between the vertex of the conical or pyramidal beam and the detector and, on the other hand, the distance between the vertex of the conical or pyramidal beam and the object to be examined controls a coefficient of geometrical enlargement of the object.

16. Apparatus according to claim 15, in which the source comprises a rotating anode provided with a plurality of targets and is rotatably controlled by a displacement means synchronised with the rotation of the support with respect to the source so that each pulse of the source irradiates or illuminates the detector between each rotation of the support.

17. Apparatus according to claim 6, in which the detector comprises a photographic film and the analogue-digital converter comprises a camera for reading the intensities detected on the photographic film and for converting them into digital data.

18. Apparatus according to claim 17, in which the photographic film is moved in an irregular, stop-start manner by a displacement means synchronised with the rotation of the rotating anode so that each pulse of the source irradiates or illuminates the photographic film between each stop-start movement.

19. Computer-readable medium encoded with the following stages of a computer program:
(1) averaging a first set of data to obtain n mean values ($c_i$) and averaging a second set of data to obtain m mean values ($\rho_j$), wherein the n and m mean values respectively are the ($c_i$) terms of a column generating vector and the ($\rho_j$) terms of a line generating vector,
(2) building an initial matrix (n,m) with the terms of the generating vectors, by assigning a line term and a column term ($B_{ij}$) defined by the half sum of the homoloque term ($c_i$ of the column generating vector, divided by the number (m) of terms of the line generating vector, and of the homologous term ($\rho_j$) of the line generating vector, divided by the number (n) of terms of the column generating vector, $$B_{ij} = \frac{1}{2}\left(\frac{\rho_j}{n} + \frac{c_i}{m}\right)$$

(3) adjusting the initial matrix using the following formula:

$$C_{ij} = \frac{\rho_j}{n} + \frac{c_i}{m} - \frac{1}{2nm}\left(\sum_{i=1}^{n} c_i + \sum_{j=1}^{m} \rho_j\right)$$

wherein,
- $C_{ij}$ is the term of the adjusted matrix,
- (n) is the number of lines of the initial matrix,
- (m) is the number of columns of the initial matrix,
- $\rho_j$ is the j-th term of the line generating vector calculated at stage (1), and
- $c_i$ is the i-th term of the column generating vector calculated at stage (1)

to arrive at an image corresponding to the adjusted matrix, for which the line and column boundary values calculated with the adjusted term ($C_{ij}$) are equal, respectively, for each line and column, to the terms of the line and column generating vectors, $$\sum_{j=1}^{m} C_{ij} = c_i \quad \sum_{i=1}^{n} C_{ij} = \rho_j$$

(4) repeating the stages (1) to (3) for different pairs of sets of data to respectively arrive at different adjusted matrices corresponding to different images of the sectional plane of a body,
(5) by means of a rotation operator, superimposing on a same pair of sets all the adjusted matrices obtained for the different pairs of sets of data, and
(6) displaying on a computer a synthesis image of the sectional plane of the body, corresponding to a synthesis matrix obtained by a term-by-term averaging of all the adjusted matrices obtained at stage (4) and superimposed at stage (5).

20. Computer-readable medium according to claim 19, further encoded with the following stages of the computer program:
(7) recording data obtained for different sectional planes of the body,
(8) selecting from among the recorded data, those of a particular sectional plane of the body, and
carrying out the stages (1) to (5) starting from these selected data.

21. Computer-readable medium according to claim 20, further encoded with the following stages of the computer program:
(9) correcting the selected data by multiplying them by a correction factor, and carrying out stages (1) to (5) using the selected and corrected data.

* * * * *